(12) United States Patent
Park et al.

(10) Patent No.: US 11,118,191 B2
(45) Date of Patent: Sep. 14, 2021

(54) PORCINE THY1 GENE PROMOTER SPECIFICALLY EXPRESSED IN NEURONS

(71) Applicant: Jeju National University Industry-Academic Cooperation Foundation, Jeju-si (KR)

(72) Inventors: Se Pill Park, Jeju-si (KR); Young Sok Choi, Seongnam-si (KR); Ok Hee Lee, Seongnam-si (KR); Mi Seon Park, Seoul (KR); Young Ho Kim, Yongin-si (KR); Eun Young Kim, Seoul (KR); Seung Eun Lee, Jeju-si (KR)

(73) Assignee: Jeju National University Industry-Academic Cooperation Foundation, Jejn-si (KR)

( * ) Notice: Subject to any disclaimer, the term of this patent is extended or adjusted under 35 U.S.C. 154(b) by 285 days.

(21) Appl. No.: 15/735,185

(22) PCT Filed: Apr. 6, 2017

(86) PCT No.: PCT/KR2017/003750
§ 371 (c)(1),
(2) Date: Dec. 10, 2017

(87) PCT Pub. No.: WO2017/209389
PCT Pub. Date: Dec. 7, 2017

(65) Prior Publication Data
US 2018/0258446 A1    Sep. 13, 2018

(30) Foreign Application Priority Data

May 31, 2016 (KR) ........................ 10-2016-0067517

(51) Int. Cl.
*C12N 15/85* (2006.01)
*C12N 15/86* (2006.01)
*A01K 67/027* (2006.01)

(52) U.S. Cl.
CPC ...... *C12N 15/8509* (2013.01); *A01K 67/0275* (2013.01); *C12N 15/85* (2013.01); *C12N 15/86* (2013.01); *A01K 2227/108* (2013.01); *C12N 2015/8545* (2013.01); *C12N 2740/13043* (2013.01); *C12N 2830/008* (2013.01)

(58) Field of Classification Search
CPC ................... C12N 15/8509; C12N 2015/8545
See application file for complete search history.

(56) References Cited

U.S. PATENT DOCUMENTS

| | | |
|---|---|---|
| 2001/0016951 A1 | 8/2001 | Sommer et al. |
| 2003/0056231 A1 | 3/2003 | Masliah et al. |

FOREIGN PATENT DOCUMENTS

| | | |
|---|---|---|
| KR | 10-2002-0028904 | 3/2007 |
| KR | 10-2007-0024069 | 1/2008 |
| KR | 10-2010-0003223 | 1/2010 |
| KR | 10-2010-0003224 | 1/2010 |
| KR | 10-2014-0020651 | 2/2014 |
| KR | 10-2015-0145201 | 12/2015 |

OTHER PUBLICATIONS

Naito et al. J Reprod Fert 113:137-143, 1998 (Year: 1998).*
Raina et al. Gene 96-100, 2015 (Year: 2015).*
Dolatshad et al. Mammalian Genome 26:598-608, 2015. (Year: 2015).*
Translation of International Search Report and the Written Opinion dated Jul. 10, 2017 From the Korean Intellectual Property Office Re. Application No. PCT/KR2017/003750. (8 Pages).

* cited by examiner

*Primary Examiner* — Marcia S Noble

(57) ABSTRACT

A Thy1 gene promoter specifically expressed in neurons and a recombinant vector including the Thy1 gene promoter are provided. The Thy1 gene promoter may be utilized to regulate an expression of a target gene in preparation of an animal model similar to a human.

2 Claims, 22 Drawing Sheets

Specification includes a Sequence Listing.

FIG. 5

-Preparation of -4858/-2279_Luc Primer

F : 5' -(Sac I) GAGCTC TCTAGATGGGGCAAACTGGAG - 3'  SEQ ID NO: 15
R : 5' -(Nhe I) GCTAGC GGCCAATCAGAGGCTGAG - 3'  SEQ ID NO: 16

-Preparation of -2578/-40_Luc Primer

F : 5' - (KpnI) GGTACC AACCTCCATCCTCCATTCCT - 3'  SEQ ID NO: 17
R : 5' - (XhoI) CTCGAG GGTGGGAATCAGCCAAGAG - 3'  SEQ ID NO: 18

-4858/-2279-Luc

-2578/-40-Luc

PC12

NIH3T3

293T

PORCINE THY1 GENE PROMOTER SPECIFICALLY EXPRESSED IN NEURONS

RELATED APPLICATIONS

This application is a National Phase of PCT Patent Application No. PCT/KR2017/003750 having International filing date of Apr. 6, 2017, which claims the benefit of priority of Korean Patent Application No. 10-2016-0067517 filed on May 31, 2016. The contents of the above applications are all incorporated by reference as if fully set forth herein in their entirety.

SEQUENCE LISTING STATEMENT

The ASCII file, entitled 71968US_Sequence Lising.txt, created on Dec. 10, 2017, comprising 47,569 bytes, submitted concurrently with the filing of this application is incorporated herein by reference. The sequence listing submitted herewith is identical to the sequence listing forming part of the international application.

FIELD AND BACKGROUND OF THE INVENTION

The following description relates to a neuronal-specific expression porcine Thy1 gene promotor.

Using animal models to find new therapies for brain diseases is an essential element in finding new therapeutic targets and performing drug testing at preclinical stages.

Studies of these animal models may play an important role in accurately detecting abnormal brain cell spatiotemporal change processes and brain dysfunction mechanisms, and verifying the effectiveness of various new therapeutic targets and new therapies. Until now, most of the disease models for drug therapy or mechanism studies of degenerative brain diseases have been mostly using rodents, but the pathological patterns and symptoms of animal disease models are much different from those observed in humans. Thus, there have been many problems in a case where clinical trials are performed based on results from rodent disease models. Accordingly, it has become very important to make disease models that may be used in research for pathological mechanism and treatment of various diseases using animals having high similarity to humans. However, since primates are so scarce that it is difficult and costly to manage the breeding, they may be used for disease research only in extremely limited fields. Therefore, attempts have been continuously made to utilize pigs that may conduct more accurate disease research as new model animals at relatively low cost and facilities.

When it is intended to produce pigs as brain disease models, it is very important that the gene related to brain diseases is specifically expressed in the pig brain or nerve. It is a promoter that regulates such tissue-specific expression. The promoter is a genomic region linked to the upper side of a structural gene, and plays a role of regulating transcription of the structural gene linked to mRNA. Promoters are activated by the binding of several common transcription factors, and they have a base sequence such as TATA box and CAT box, etc. that regulate gene expression in general. Since the proteins required for basic metabolism in a living body must maintain a constant concentration in the cells, the promoter linked to these genes is always activated by the action of common transcription factors alone. On the contrary, proteins that do not have a role in normal times and function only under specific circumstances are linked to an inducible promoter which induces the expression of the corresponding structural gene. Inducible promoters are activated by the binding of specific transcription factors activated by external stimuli that come from environmental factors from the surroundings during the development of an organism. That is, when a model pig for a brain disease is prepared, a gene expression system may work well if a disease-related gene is introduced together with a promoter capable of inducing specific expression in a porcine brain or nerve cell.

SUMMARY OF INVENTION

Example embodiments provide a Thy1 gene promoter specifically expressed in neurons and a recombinant vector including the same.

Example embodiments provide a transformed cell line using a Thy1 gene promoter specifically expressed in neurons and a recombinant vector including the same.

However, the subject matters to be solved by the disclosure are not limited to the above-mentioned subject matters, and the other subject matters that are not mentioned may be clearly understood by those skilled in the art from the following descriptions.

According to an example embodiment, there is provided a Thy1 gene promoter specifically expressed in neurons, including the base sequence of SEQ ID NO: 1.

According to an example embodiment, there is provided a Thy1 gene promoter specifically expressed in neurons, including the base sequence of SEQ ID NO: 4.

According to one aspect, the promoter may include a binding site of a PBX and a CREB transcription factor.

According to an example embodiment, there is provided a primer set including the sequence of SEQ ID NO: 2 and SEQ ID NO: 3 and for amplifying the promoter of claim 1.

According to an example embodiment, there is provided a primer set including the sequence of SEQ ID NO: 5 and SEQ ID NO: 6 and for amplifying the promoter of claim 2.

According to an example embodiment, there is provided a recombinant expression vector including a Thy1 gene promoter having the base sequence of SEQ ID NO: 1 or SEQ ID NO: 4 and a gene related to Alzheimer's disease.

According to one aspect, the Alzheimer's disease-related gene may be an APP mutant gene, a Tau mutant gene, or a PS1 mutant gene.

According to an example embodiment, there is provided a somatic cell of a mammal transformed by introducing the recombinant expression vector.

According to an example embodiment, there is provided a mammalian embryo in which the recombinant expression vector is injected.

According to an example embodiment, there is provided a transgenic mammal obtained by implanting the embryo in a uterus of a surrogate mother.

According to an example embodiment, there is provided a method of preparing a recombinant expression vector, in which the method includes: constructing a first vector including a restriction enzyme site and removing the promoter and gene cluster; preparing a recombinant second vector by inserting the promoter. APP gene. PS1 gene, Tau gene and the promoter of claim 1 into a second vector, respectively; inducing a mutation in each of APP gene, PS1 gene and Tau gene on the recombinant second vector; and inserting the recombinant second vector into the first vector.

According to an example embodiment, there is provided a method of preparing a transgenic pig, in which the method includes: preparing the recombinant expression vector;

separating somatic cells from the pig; introducing the expression vector into the somatic cells; selecting and culturing clone somatic cells into which the expression vector is introduced; removing the nucleus of the oocyte harvested from a surrogate mother and fusing the cloned somatic cells; and transplanting the fused clone into a surrogate mother.

According to example embodiments, a promoter specifically expressed in neurons is derived from a pig, and has high activity in brain cells or neurons, and thus may be used for controlling the expression of a target gene. In particular, as compared with rodent mice, pigs are highly similar to human genes and have many similarities in terms of metabolism. Therefore, pigs may be transformed into recombinant vectors and used as disease models, so that the promoter may also be utilized in the preparation of such disease models.

BRIEF DESCRIPTION OF THE SEVERAL VIEWS OF THE DRAWINGS

FIG. 5 illustrates a primer for preparing a luciferase reporter vector.

DESCRIPTION OF SPECIFIC EMBODIMENTS OF THE INVENTION

Figure 1:
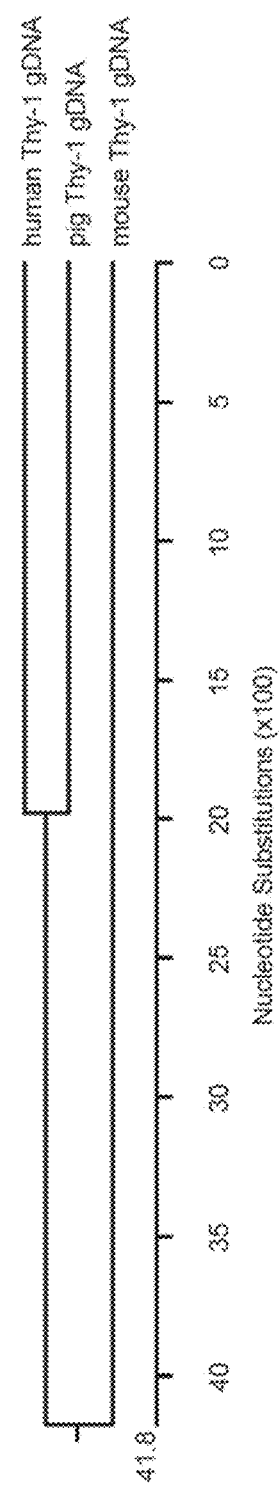
FIG. 1 illustrates the phylogenetic similarity of the Thy-1 gene through the ClustalV method.

The following detailed description is provided in order to explain the example embodiments by referring to the figures.

Various modifications may be made to example embodiments. However, it should be understood that these embodiments are not construed as limited to the illustrated forms and include all changes, equivalents or alternatives within the idea and the technical scope of this disclosure.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in describing of example embodiments, detailed description of well-known related structures or functions will be omitted when it is deemed that such description will cause ambiguous interpretation of the present disclosure.

The term "recombinant" refers to a cell in which a cell replicates a heterologous nucleic acid, expresses the nucleic acid, or expresses a protein encoded by a peptide, a heterologous peptide or a heterologous nucleic acid. Recombinant cells may express genes or gene segments that are not found in the native form of the cells, either in sense or antisense form. In addition, recombinant cells may express a gene found in a cell in a natural state, but the gene has been reintroduced intracellularly by artificial means as modified.

The term "vector" is used to refer to a DNA fragment (s), nucleic acid molecule, which is delivered into a cell. The vector replicates the DNA and may be independently regenerated in the host cell. The term "carrier" is often used interchangeably with "vector." The term "expression vector" means a recombinant DNA molecule including a desired coding sequence and a suitable nucleic acid sequence necessary for expressing a coding sequence operably linked in a particular host organism. Promoters, enhancers, termination signals and polyadenylation signals available in eukaryotic cells are known.

The mouse Thy1 promoter, which has been conventionally used mainly, has a remarkably low similarity of the Thy1 promoter of the pigs or humans, whereas the Thy1 promoter of the pig and the human Thy1 promoter are very similar to each other (see Example 1). For example, in producing a pig model of a brain disease or neurological disease, it is very important to produce a promoter capable of ensuring specific expression of brain cells or neurons, and in particular, a promoter fragment with high activity having the size that may be used for a recombinant expression vector is essential.

According to an example embodiment, there is provided a Thy1 gene promoter that specifically expresses in a neuron, including the base sequence of SEQ ID NO: 1. The base sequence of SEQ ID NO: 1 has a size of 500 bp, but any base sequence including the same may be used without limitation. Preferably, a promoter having a base sequence of a size of 500 bp to 2579 bp may be used. In an example embodiment, SEQ ID NO: 4 exhibits the base sequence of a promoter having a size of 2579 bp at positions −4858 to −2279. With reference to SEQ ID NO: 1 and SEQ ID NO: 4, a promoter having a base sequence ranging from 500 bp to 2579 bp may be used.

Also, the variome of the promoter sequence is included within the scope of the disclosure. The variome is a base sequence having a functional characteristic similar to that of the base sequence of SEQ ID NO: 1 although the base sequence thereof is changed. Specifically, the promoter may include a base sequence having 70% or more, 80% or more, 90% or more, or 95% or more of sequence homology with the base sequence of SEQ ID NO: 1, respectively. "% of sequence homology" to polynucleotides is determined by comparing the comparison region with two optimally aligned sequences, and a portion of the polynucleotide sequence in the comparison region may be added or deleted (i.e., gap), as compared to the reference sequence (which does not include an addition or deletion).

According to one aspect, the promoter may include a binding site of a PBX and a CREB transcription factor. The PBX and CREB transcription factors are transcription factors known to be associated with brain diseases.

According to an example embodiment, there is provided a primer set consisting of the sequences of SEQ ID NO: 2 and SEQ ID NO: 3 and for amplifying the promoter of claim 1.

In addition, according to one aspect, there is provided a primer set consisting of the sequences of SEQ ID NO: 5 and SEQ ID NO: 6 and for amplifying the promoter of SEQ ID NO: 4.

According to an example embodiment, there is provided a recombinant expression vector including a Thy1 gene promoter having a base sequence of SEQ ID NO: 1 and an Alzheimer-related gene.

According to one aspect of the disclosure, the expression vector may be used without limitation as long as it may be used to efficiently induce the expression of the Alzheimer-related protein specifically in the neuron. Preferably, however, the retroviral vector may be used. For example, pTet-CKOS may be used. In addition, the expression vector may further include an enhancer to further improve the expression of the gene, for example, a CMV (cytomegalo virus) enhancer.

According to one aspect, the Alzheimer's disease-related gene may be an APP mutant gene, a Tau mutant gene, or a PS1 mutant gene. It is known that APP, Tau, and PS1, which are known to be typical genes causing Alzheimer's disease, contribute to overexpression of β-amyloid, which is a pathogenesis of Alzheimer's disease, and aggregation of Tau protein. β-amyloid is produced from amyloid precursor protein (APP) through a proteolysis process. APP, which is a precursor protein, is a protein with a transmembrane domain and is expressed in several isotypes by alternative splicing and is known to undergo two metabolic pathways within the cell. Mutations in this APP protein are found in patients with familial Alzheimer's disease. The mutations discovered so far include APP670/671 (Swedish). APP672 (Flemish), APP716 (Florida), APP717 (London), and these mutations have been shown to increase the formation of β-amyloid. Another gene that shows a mutation that causes familial Alzheimer's disease is presenilin 1 (PS1). PS1 is a protein with eight transmembrane domains and plays an important role in a process of generation and is known to act as a member of γ-secretase itself or a complex. PS1 has been reported to have 45 mutations or more that cause familial Alzheimer's disease throughout the protein, and these mutations have also been shown to increase the amount of β-amyloid formation. It is known that the onset of Alzheimer's disease caused by the generated β-amyloid is accompanied by a process of neuronal damage by hyperphosphorylation of Tau protein, and several phosphorylases are involved in hyperphosphorylation of such Tau protein. In addition to hyperphosphorylation of Tau, tangle formation of Tau has also been shown to play a role in neuronal damage and a mutation of Tau in which the tangle is well formed has been found.

The recombinant expression vector may further include a 2A sequence between the APP mutant gene, the Tau mutant gene and the PS1 mutant gene, respectively. In an example embodiment, a 2A sequence is further included between the APP mutant gene and the tau mutant gene, and a 2A gene may be further included between the tau mutant gene and the PS1 mutant gene.

The 2A gene sequence encodes 18 to 22 amino acids, and among them, the four amino acids Asparagine (N), Proline (P), Glycine (G) and Proline (P) located at the terminal are important amino acids conserved between the species. Such sequences tend to self-cleavage when synthesized into peptides. Due to this property, when a ribosome reaches a genetic code that encodes N, P. G located at the 2A sequence terminal when protein transcription proceeds. NPG is sequentially recognized to make a peptide bond, and then instead of bringing a prolyl-tRNA with Proline linked to the amino acid proline encoding code, it brings a releasing factor (RF). After the binding of the RF factors, the previously formed peptides are no longer able to bind peptide and are released from ribosomes. After the 2A sequence, the encoded code works normally and the next protein transcription proceeds. In conclusion, by inserting the 2A sequence, many genes may be expressed using one promoter. The recombinant expression vector of the disclosure may simultaneously express these genes by inserting these 2A sequences into each of the three genes.

The APP mutant gene may be one in which amino acid 595, amino acid 596, or both of them are mutated. In an example embodiment of the mutated amino acids, the APP mutant gene may be a gene in which the 595 amino acid Lys of APP595 is mutated to Asn and the 596 amino acid Met is mutated to Lys. In one embodiment, APP mutant 595 is encoded by the nucleic acid sequence of SEQ ID NO: 19, wherein N1785 is T, N1786 is A, N1923 is A and N1924 is G, APP mutant 596 is encoded by the nucleic acid sequence of SEQ ID NO: 19, wherein N1785 is G, N1786 is C, N1923 is A, N1924 is G, and APP mutant 595/596 is encoded by the nucleic acid sequence of SEQ ID NO: 19, wherein N1785 is T, N1786 is C, N1923 is A and N1924 is G. In another embodiment, APP mutant 641 is encoded by the nucleic acid sequence of SEQ ID NO: 19, wherein N1785 is G, N1786 is A, N1923 is G and N1924 is G, APP mutant 642 is encoded by the nucleic acid sequence of SEQ ID NO: 19, wherein N1785 is G, N1786 is A, N1923 is A and N1924 is A, and APP mutant 641/642 is encoded by the nucleic acid sequence of SEQ ID NO: 19, wherein N1785 is G, N1786 is A, N1923 is G and N1924 is A The TAU mutant gene may be one in which amino acid 243 is mutated. In one embodiment, the TAU mutant gene may be a gene in which the 243 amino acid Phe is mutated to Lys. In one embodiment, TAU mutant 243 is encoded by the nucleic acid sequence of SEQ ID NO: 20, wherein N728 is T. In addition, the PS1 mutant gene may be one in which amino acid 146, amino acid 286, or both of them are mutated. The PS1 mutant gene may also be a gene in which the 146 amino acid Met is mutated to Leu and the 286 amino acid Pro is mutated to Leu. In one embodiment, PS1 mutant 146 is encoded by the nucleic acid sequence of SEQ ID NO: 21, wherein N436 is C and N856 is C, PS1 mutant 286 is encoded by the nucleic acid sequence of SEQ ID NO: 21, wherein N436 is A and N856 is G, and PS1 mutant 146/286 is encoded by the nucleic acid sequence of SEQ ID NO: 21, wherein N436 is C and N856 is G.

According to an example embodiment, there is provided a somatic cell of a mammal transformed by introducing the recombinant expression vector. The cell may be used without limitation except for humans if it originates from a mammal. However, in the case of a mouse, which is mainly used conventionally, metabolism is very fast, and since the lifetime change is very different from that of the humans, it is difficult to use it as an accurate disease model. Therefore, an animal having a size similar to a human body and having a similar shape in terms of metabolism is preferable, and a pig is most preferable among them. According to an example embodiment, there is provided a mammalian embryo in which the recombinant expression vector is injected. According to an example embodiment, there is provided a transgenic mammal obtained by implanting the embryo in a uterus of a surrogate mother.

According to an example embodiment, there is provided a method of preparing a recombinant expression vector, in which the method includes: constructing a first vector including a restriction enzyme site and removing a promoter and gene cluster; preparing a recombinant second vector by inserting the promoter, APP gene, PS1 gene and Tau gene of claim 1 into a second vector, respectively; inducing a mutation in each of APP gene, PS1 gene and Tau gene on the recombinant second vector; and inserting the recombinant second vector into the first vector.

According to an example embodiment, there is provided a method of preparing a transgenic pig, in which the method includes: preparing the recombinant expression vector; separating somatic cells from the pig; introducing the expression vector into the somatic cells; selecting and culturing clone somatic cells into which the expression vector is introduced; removing the nucleus of the oocyte harvested from a surrogate mother and fusing the cloned somatic cells; and transplanting the fused clone into a surrogate mother.

Hereinafter, the disclosure will be described in more detail with reference to examples. The following examples are given for the purpose of illustrating the disclosure, and the scope of the present disclosure is not limited thereto.

Example 1: Investigation of Thy1 Gene Similarity Between Humans, Mice and Pigs Using Phylogenetic Analysis and zPicture Analysis In order to analyze the sequences of Thy1 genes, the global genes of the humans (GeneID: 7070), mouse (GeneID: 21838), pigs (GeneID: 100109488) and the promoter (about 2.2 to 2.6 kb forward from the first exon) DNA sequence were downloaded from National Center for Biotechnology Information (NCBI). The phylogenetic similarity of each DNA sequence was investigated using DNASTAR Lasergene Megalign software. The Align method was used as the Clustal V method.

FIG. 1 illustrates the phylogenetic similarity of the Thy-1 gene through the ClustalV method.

Referring to FIG. 1, it may be understood that the Thy1 gene of humans and pigs is located very close compared to the Thy 1 gene of a mouse.

The similarity of the Thy1 gene in human-to-pig or pig-to-mouse was compared with each other in order to investigate the similarity of the interspecific genes of Thy1 and determine the promoter range and the candidate sequence of porcine Thy1 by locating promoters with high similarity. The comparison tool was a zPicture analysis tool based on a pairwise sequence aligner. The Thy1 gene in humans, pigs, and mice consists of four exons, and the ATG codon that initiates protein expression is located in the second exon. A of ATG is named as +1 position. The nucleotide located at the front is named as "−number" and the back of A is named as "+number". In humans, the gene sequence that regulates the expression of Thy1 gene specifically in brain tissue is important from the front of the first exon to the front of the second exon (−3463 to −1).

Figure 2:
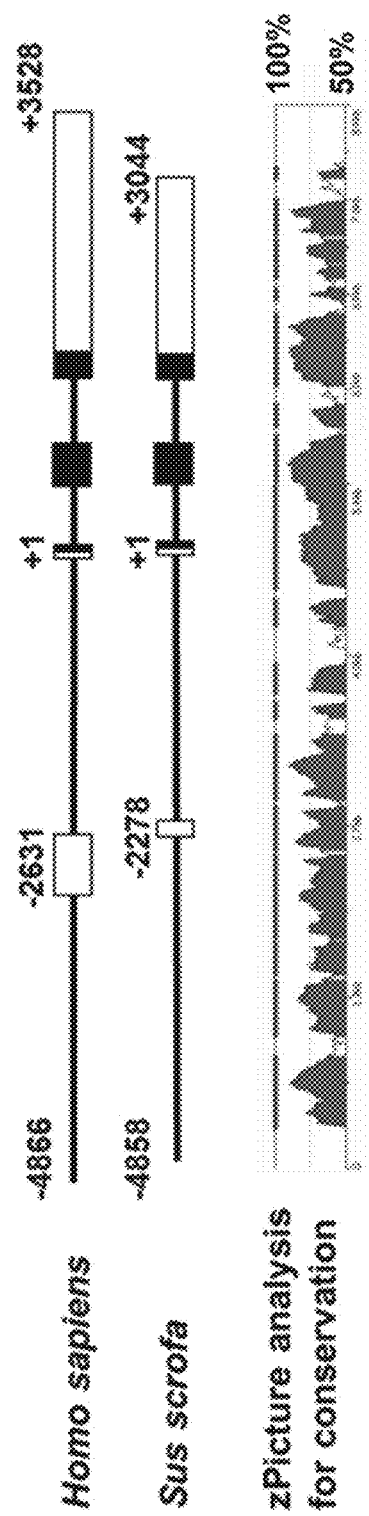
FIG. 2 is an analysis of the Thy-1 gene similarity between humans and pigs using zPicture.
Figure 3:
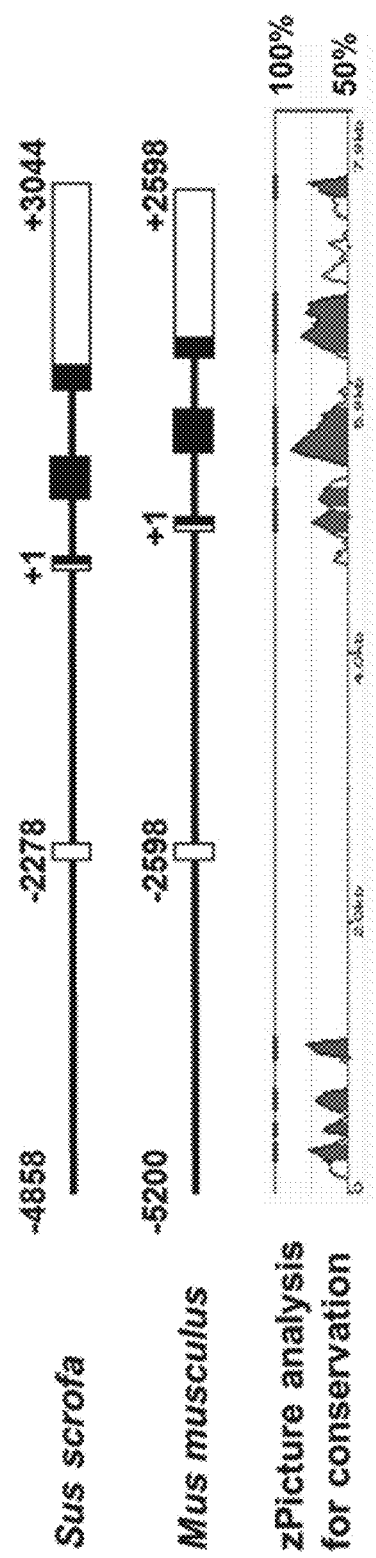
FIG. 3 is an analysis of the Thy-1 gene similarity between pigs and mice using zPicture.

FIG. 2 is an analysis of the Thy-1 gene similarity between humans and pigs using zPicture. FIG. 3 is an analysis of Thy-1 gene similarity between pigs and mice using zPicture.

Referring to FIG. 2, when the Thy1 gene similarity between pigs and humans is analyzed, the DNA sequence similarity is high in front of the first exon and the first intro sequence is less similar. On the other hand, referring to FIG. 3, when DNA sequences of pigs and mice are compared, except for the coding sequence expressing the protein and the front of the first exon, the overall DNA sequence similarity is poor. That is, the similarity of the Thy1 gene in pigs and humans is very high. Among them, the gene sequence located at −4858 to −2278 of Thy1 is highly likely to be involved in the regulation of Thy1 expression.

Example 2: List of Predicted Transcriptional Regulatory Factors Binding to a Human and Porcine Thy1 Gene Promoter rVista 2.0 was used as an analytical tool to investigate the predicted transcriptional regulatory factors binding to the human and porcine Thy1 gene promoters.

Table 1 below shows the transcriptional regulatory factors binding to the Thy1 gene promoter.

TABLE 1

| −4858 to −3858 | −3858 to −2858 | −2858 to −1858 |
|---|---|---|
| SMAD4 | NKX25B | EGR2 |
| MAZR | TBX5 | EGR3 |
| SP1 | ARP1 | SRF |
| MAZ | CDP | LRF |
| RORA | CLOX | NFY |

TABLE 1-continued

| −4858 to −3858 | −3858 to −2858 | −2858 to −1858 |
|---|---|---|
| HTF | PBX | CAAT |
| ER | NFY | ZIC3 |
| XBP1 | AREB6 | CHCH |
| RUSH1 | AP2A | MTF |
| LFA1 | AP2G | ETF |
| ELK1 | CREB | |
| TEF1 | HNF4 | |
| RBPJK | SZF11 | |
| | STAF | |
| | E2F1 | |
| | HSF1 | |
| | HSF2 | |
| | SMAD4 | |
| | EGR1 | |

Figure 4:
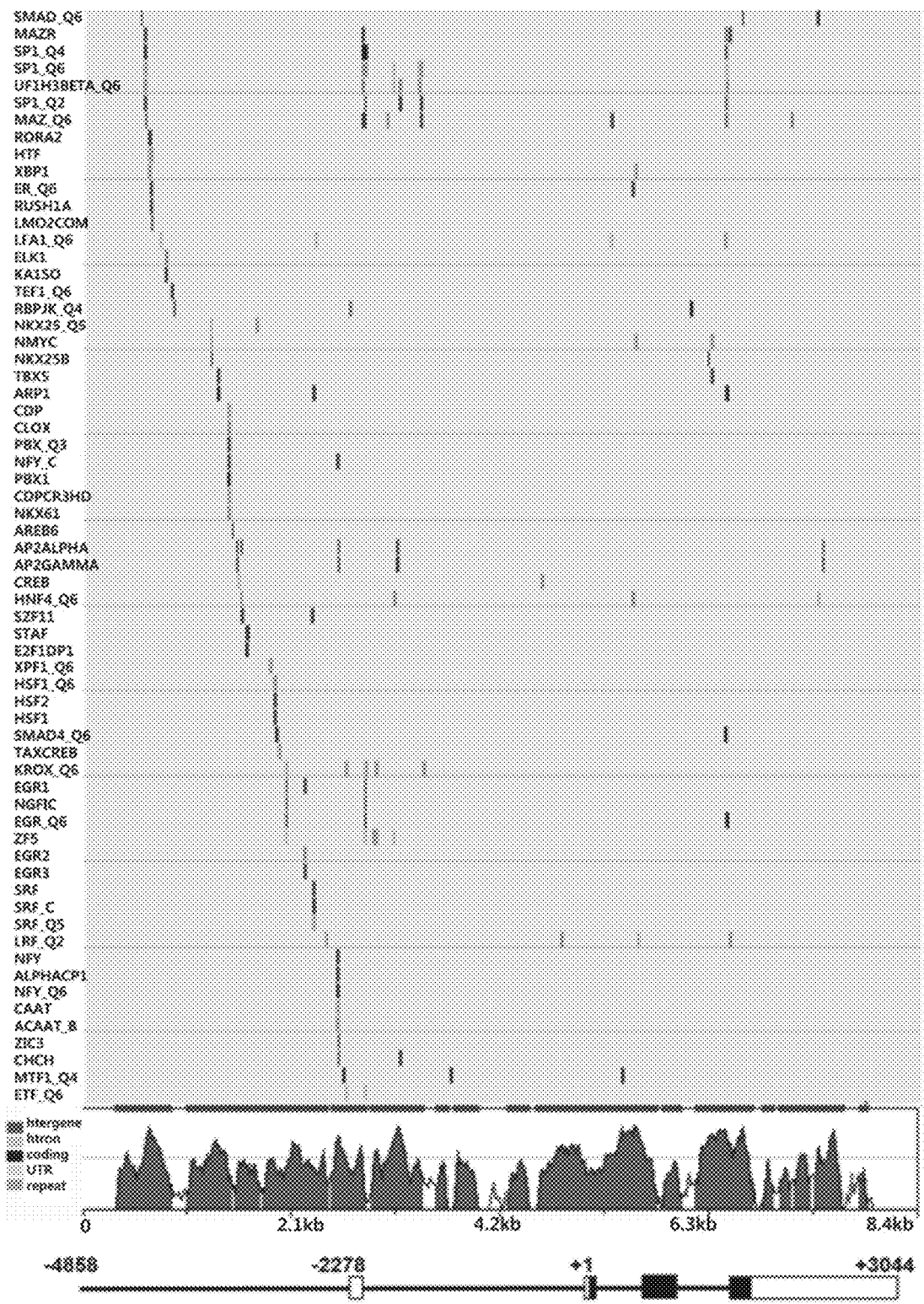
FIG. 4 illustrates the location of a transcriptional regulator binding to the Thy1 gene promoter.

FIG. 4 illustrates the location of the transcriptional regulatory factors binding to the Thy1 gene promoter.

Referring to Table 1 and FIG. 4, there exists a DNA sequence capable of binding transcriptional regulator factors such as TBX5, PBX, CREB, AREB6, AP2, E2F1, HSF1, SMAD4, EGR1, EGR2, EGR3, etc. in about 1 kb upstream toward the front of the first exon of the porcine Thy1 gene. Among them, in particular. PBX and CREB transcriptional regulatory factors are known to be related to brain diseases. Therefore, the promoter region of the porcine Thy1 of −3858 to −2858, particularly −3380 to −2880, is important for the expression of brain tissue-specific Thy1.

Example 3: Analysis of Luciferase Reporter Vector and Luciferase for Measuring the Activity of Porcine Thy1 Promoter Based on the analysis of Examples 1 and 2, a luciferase reporter vector was produced to find the Thy1 promoter DNA sequence of a pig inducing tissue-specific expression in actual cells. The primers were designed to make the −4858/−2279_Luc vector in which the Thy1 gene −4858 to −2279 was inserted in front of the luciferase cDNA and the −2578/−40_Luc vector in which −2578 to −40 was inserted.

SEQ ID NO: 7 exhibits the base sequence (2579 bp) of the Thy1 promoter −4858 to −2279 location and SEQ ID NO: 8 exhibits the base sequence (0.2538 bp) of the Thy1 promoter −2578 to −40 location.

FIG. 5 illustrates a primer for producing a luciferase reporter vector.

After isolating the chromosomes from the pigs, a Thy promoter DNA having a base sequence of −4858 to −2279 and a base sequence of −2578 to −40 was synthesized by PCR using a pig chromosome as a template using the above primer, and TA was cloned in a pTOP TA V2 vector. The synthesized DNA sequence was confirmed to be accurately synthesized by sequencing.

Figure 6A:
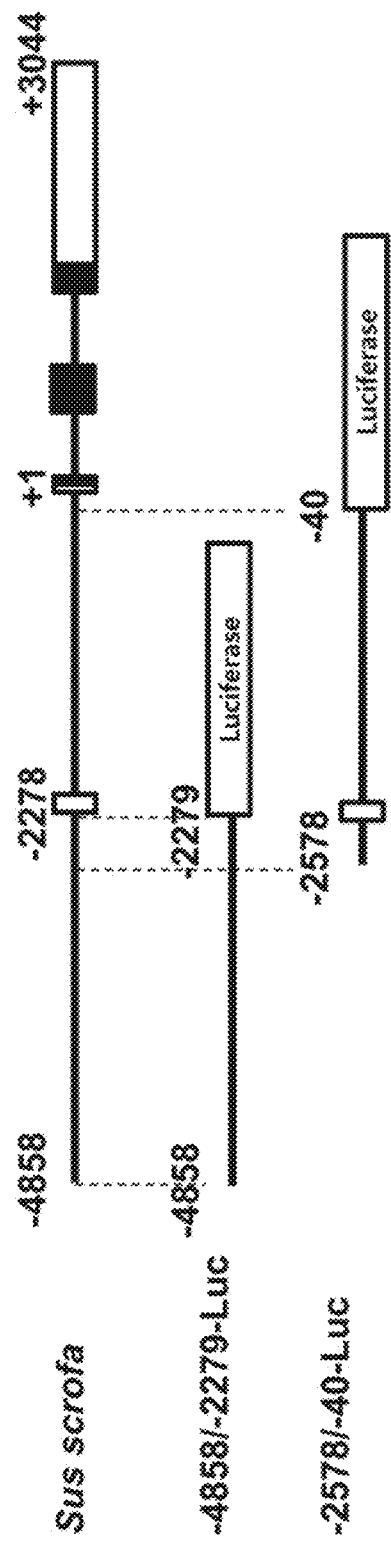
FIG. 6A illustrates a location of a Thy1 promoter DNA inserted into the luciferase reporter vector.

Referring to FIG. 6A, the location of the Thy1 promoter DNA inserted into the luciferase reporter vector may be roughly known. Each Thy1 promoter was cut from pTOP and inserted into the pGL4.10 [luc2] vector using the SacI/NheI restriction enzyme to clone the −4858/−2279_Luc vector and the KpnI/XhoI restriction enzyme to the −2578/−40_Luc vector. SEQ ID NO: 9 exhibits the base sequence (4242 bp) of the pGL4.10 [luc2] vector.

Figure 6B:
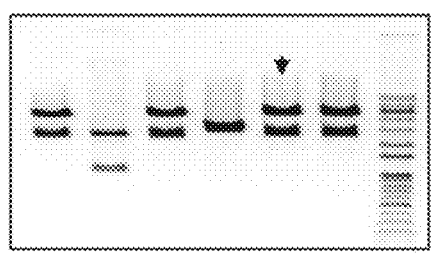
FIG. 6B is a schematic diagram of a luciferase reporter vector for measuring the activity of the Thy1 promoter.
Figure 6B:
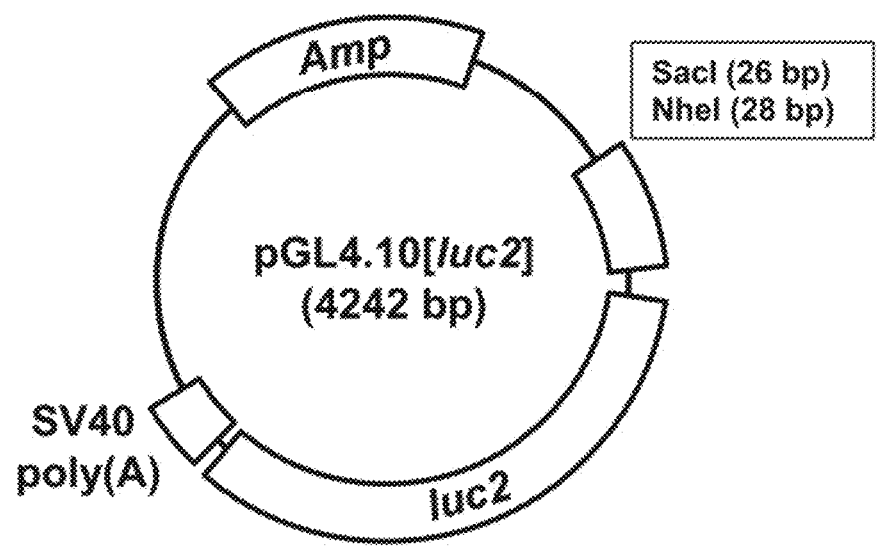
Figure 6C:
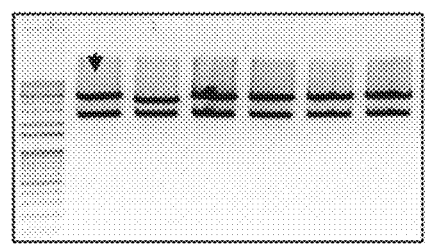
FIG. 6C is a schematic diagram of a luciferase reporter vector for measuring the activity of the Thy1 promoter.
Figure 6C:
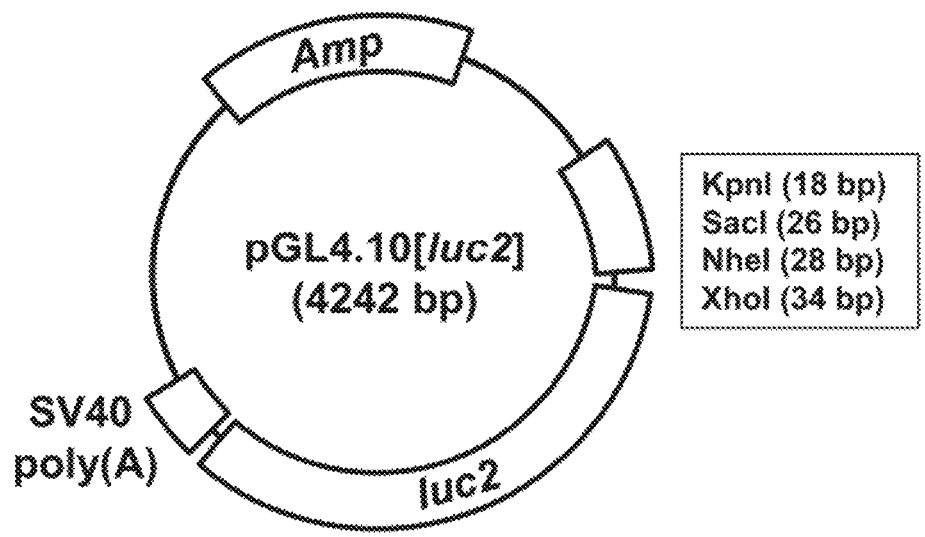

FIGS. 6B and 6C are schematic diagrams illustrating each respective vector and used restriction enzymes.

A luciferase assay was performed to investigate whether the two synthesized Thy1 promoters exhibited actual neuronal-specific expression patterns. 500 ng of −4858/−2279_Luc or −2578/−40_Luc vectors were transfected with 50 ng of pRL-TK vector using Lipofectamine 2000 in representative neuronal cell lines SH-SY5Y and PC12. As a control group, 500 ng of the basic pGL4.10 [luc2] was transfected. In addition, 293T cells were used as a negative control group cell line for neurons to investigate the activity of the promoter.

Figure 7:
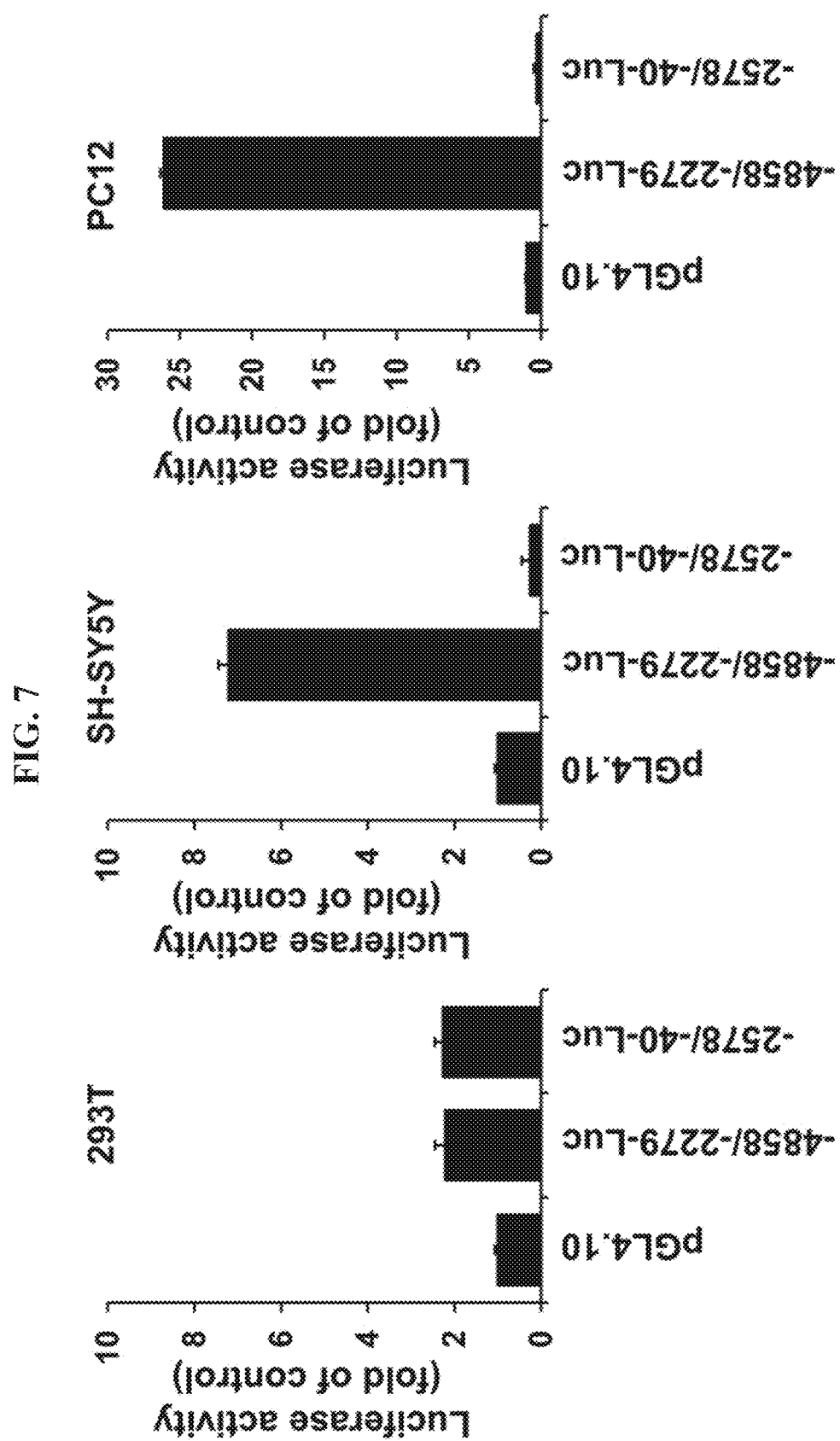
FIG. 7 is a graph illustrating brain cell-specific activity of the Thy1 promoter of pigs measured by luciferase assay.

FIG. 7 is a graph illustrating brain cell-specific activity of the Thy1 promoter of pigs measured by luciferase assay.

Referring to FIG. 7, the activity of the two Thy1 promoters was low in the non-neuronal 293T cell, whereas the promoter activity of −4858/−2279_Luc in the SH-SY5Y and PC12 neuronal cell lines was very high. In the case of −2578/−40_Luc, the promoter activity is not specifically observed in the neuronal cell line. Therefore, the DNA sequence present in the −4858 to −2279 site of the Thy1 promoter is important for neuron-specific Thy1 expression.

Example 4: Fluorescence Reporter Vector and Fluorescence Analysis for Measuring the Activity of Thy1 Promoter of Intracellular Porcine In order to measure the activity of Thy1 promoter through image analysis. EGFP expression vector and DsRed2 expression vector under transcriptional regulation of Thy1 promoter −4858/−2279 were prepared.

Figure 8A:
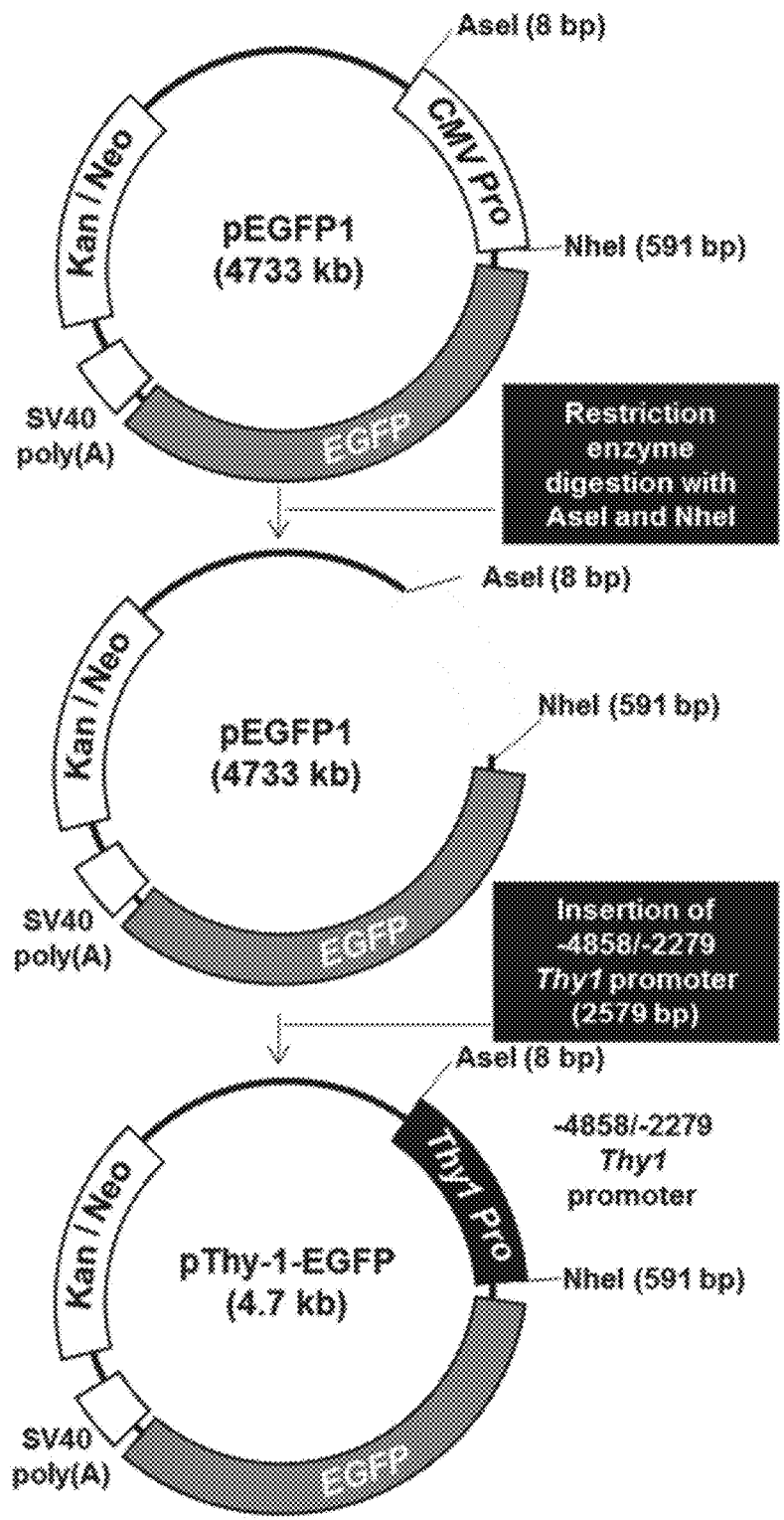
FIG. 8A is a schematic diagram of a reporter vector (pThy1-EGFP vector) for measuring the activity of the Thy1 promoter.
Figure 8B:
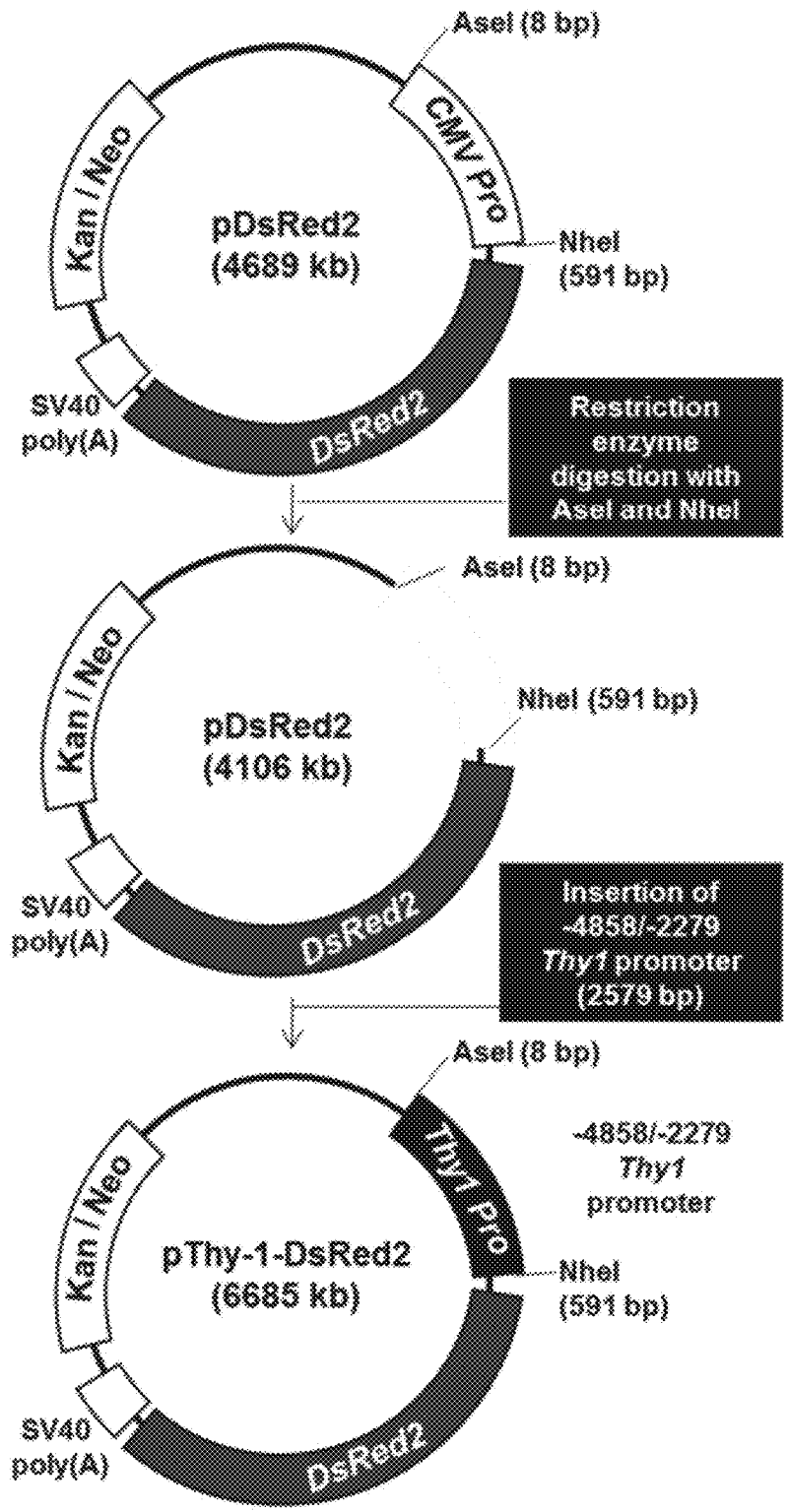
FIG. 8B is a schematic diagram of a reporter vector (pThy1-EGFP vector) for measuring the activity of the Thy1 promoter.

FIGS. 8A and 8B are schematic diagrams of a reporter vector for measuring the activity of the Thy1 promoter.

Referring to FIG. 8, a Thy1 promoter of −4858 to −2279 was synthesized by plasmid PCR using −4858/−2279_Luc as a template. The CMV promoter of pEGFP1 and pDsRed2 was removed with AseI and NheI restriction enzyme, and then the pThy1-EGFP vector (FIG. 8A) and the pThy1-DsRed2 vector (FIG. 8B) were prepared by inserting the Thy1 promoter of −4858 to −2279.

SEQ ID NO: 10 exhibits the base sequence (4733 bp) of the pThy1-EGFP vector and SEQ ID NO: 11 exhibits the base sequence (4689 bp) of the pThy1-DsRed2 vector.

The primers used for preparing the EGFP expression vector and the DsRed2 expression vector are as follows.

```
F:
                                    (SEQ ID NO: 13)
5'-(Ase I) ATTAAT TCTAGATGGGGCAACTGGAG-3'

R:
                                    (SEQ ID NO: 14)
5'-(Nhe I) GCTAGC GGCCAATCAGAGGCTGAG-3'
```

In 293T cells, each vector was transfected with pEGFP1, pThy1-EGFP, pDsRed2, and pThy1-DsRed2, respectively, using Lipofectamin 2000 and observed with fluorescence microscope two days later.

Figure 9:
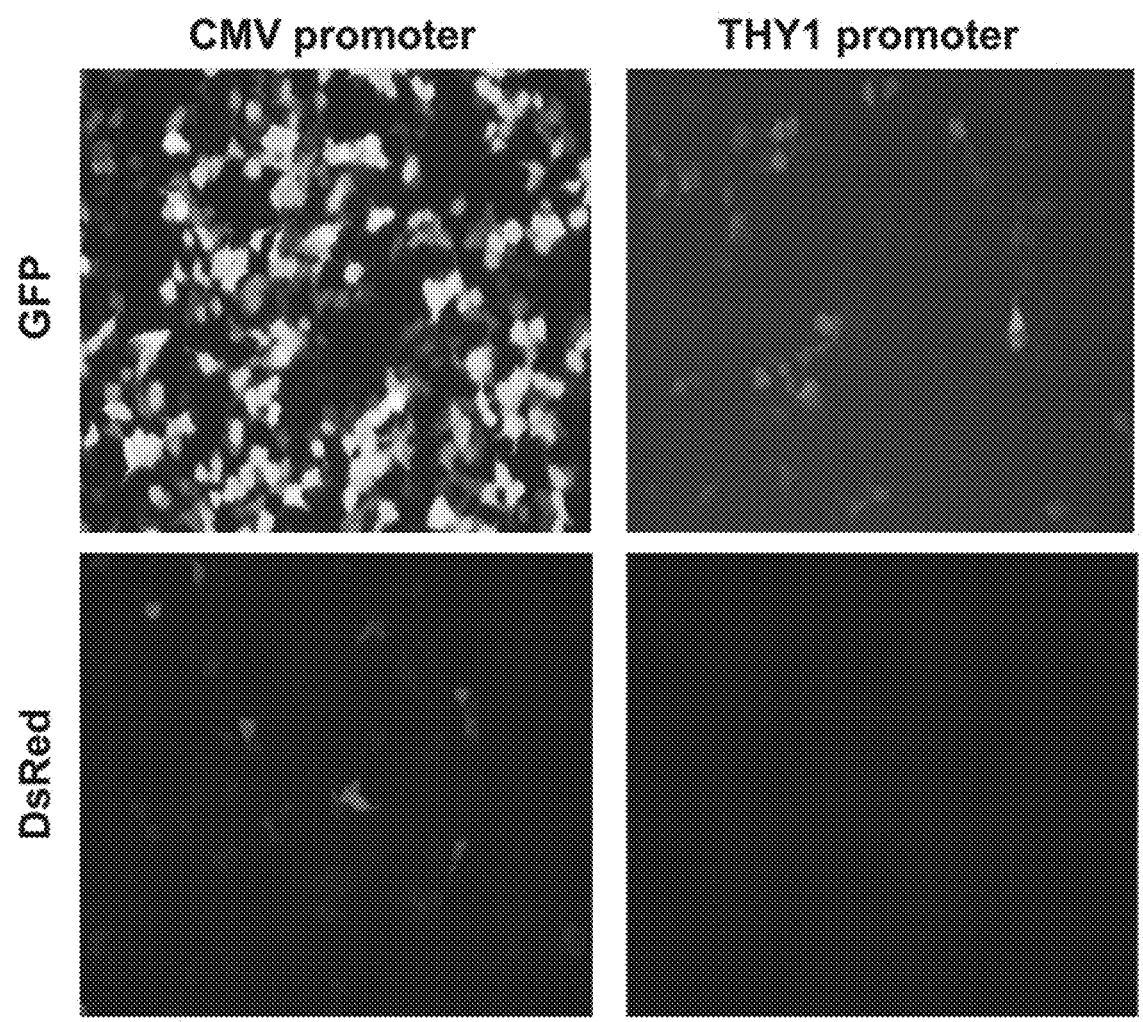
FIG. 9 is a fluorescence microscope photograph illustrating the intracellular Thy1 promoter and CMV promoter activity.

FIG. 9 is a fluorescence microscope photograph illustrating the intracellular Thy1 promoter and CM V promoter activity.

Referring to FIG. 9, the expression of GFP and DsRed proteins under the control of the CMV promoter was very high in 293T cells, whereas the expression of GFP and DsRed proteins under the influence of the Thy1 promoter was relatively low. This is because 293T cells, which are a lack of Thy1 expression, lack a transcriptional regulatory factor to activate the Thy1 promoter.

Example 5: FACS Analysis of the Degree of Thy1 Expression Existing in Various Cells In order to observe the degree of the Thy1 protein basically expressing in 293T embryonic kidney cells, NIH3T3 fibroblasts, and PC12 neuronal cell lines, the cultured cells were treated with 0.25% trypsin-EDTA and removed with a single cell. Then, the primary antibody against Thy1 (produced in mice) was reacted in the cells. FITC-conjugated anti-mouse antibody was reacted and flow cytometry analysis was performed.

Figure 10A:
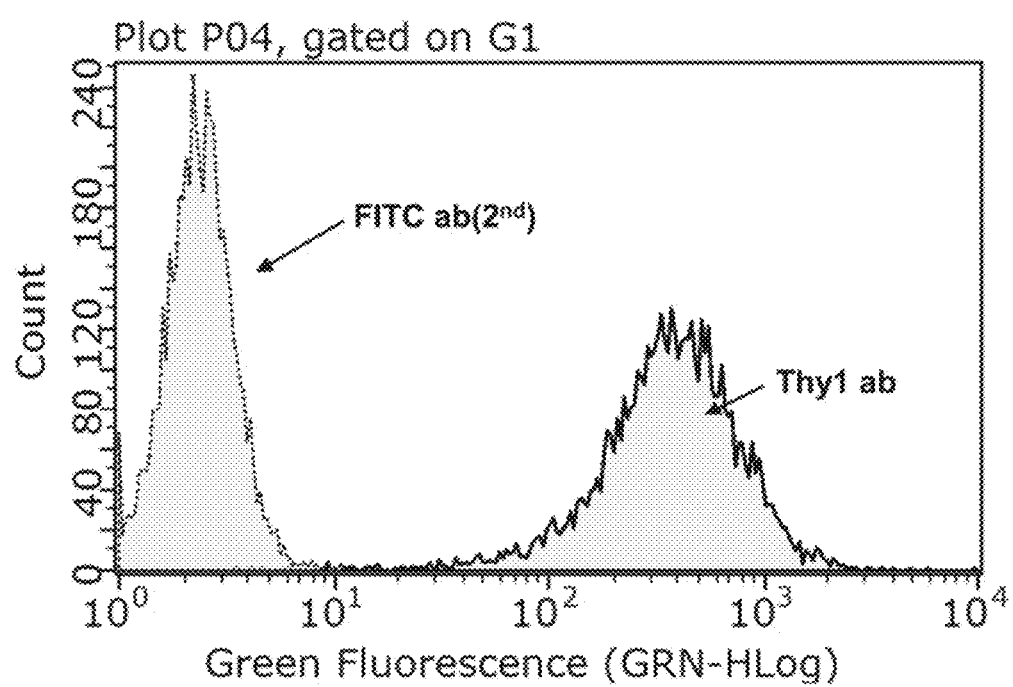
FIG. 10A is a graph illustrating the degree of Thy1 expression in the PC12 neuron cell line.
Figure 10B:
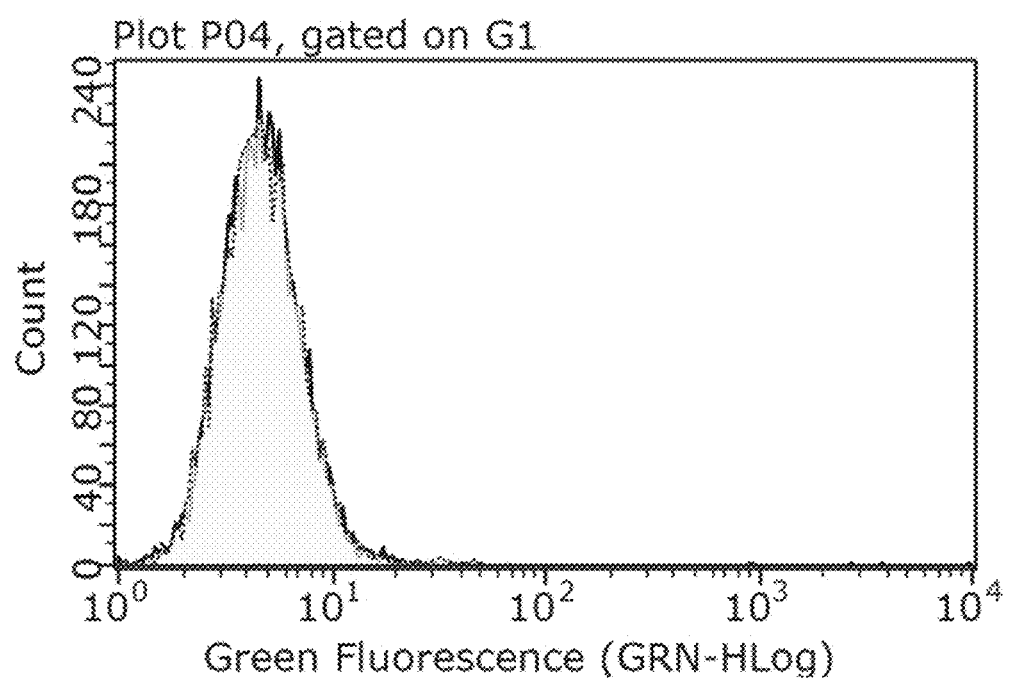
FIG. 10B is a graph illustrating the degree of Thy1 expression in NIH3T3 fibroblast.
Figure 10C:
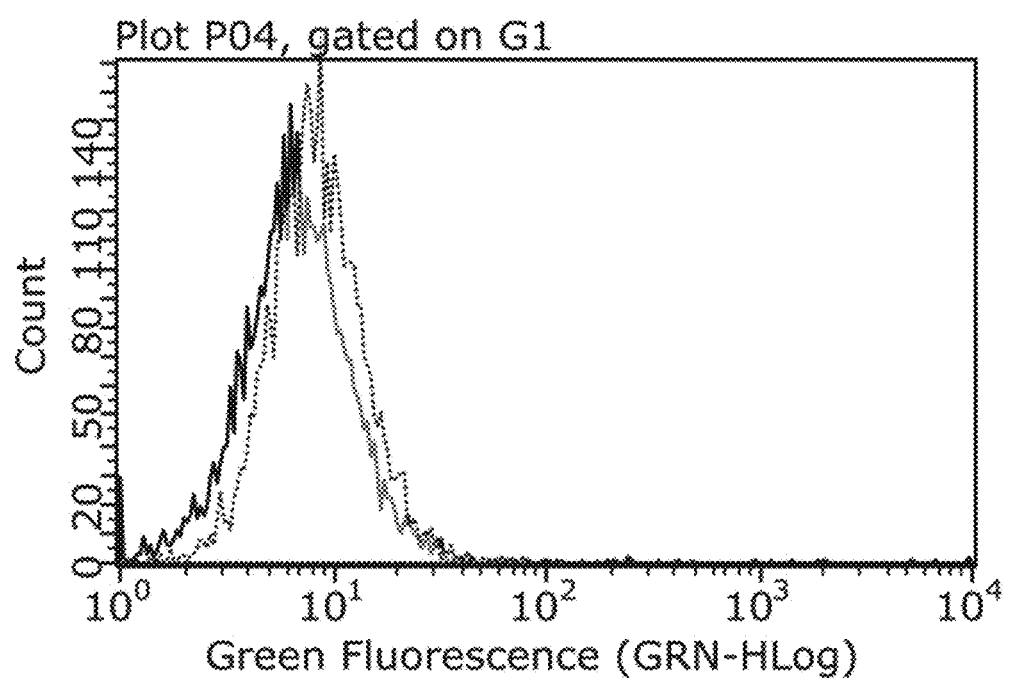
FIG. 10C is a graph illustrating the degree of Thy1 expression in 293T embryonic kidney cells.

FIG. 10A is a graph illustrating the degree of Thy1 expression in the PC12 neuronal cell lines, FIG. 10B is a graph illustrating the degree of Thy1 expression in NIH3T3 fibroblast, and FIG. 10C is a graph illustrating the degree of Thy1 expression in 293T embryonic kidney cells.

Referring to FIGS. 10B and 10C, there was almost no expression of Thy1 protein in NIH3T3 and 293T, but the expression of Thy1 in PC12 neurons of FIG. 10A was very high. That is, it is considered that the activity of the transcriptional regulatory factors for Thy1 expression is high in PC12 cells, indicating that the promoter of the disclosure plays a very large role in neuronal-specific expression.

Example 6: Expression Analysis after Transfection of a Vector Binding Thy1 Promoter and EGFP to PC12 Cells Stable cells were prepared by transfection of pEGFP1 (cmv promoter) and pThy1-EGFP (Thy1 promoter) into PC12 cells rich in transcriptional regulatory factors for Thy1 protein expression and treatment with 400 µg/ml of G418 for about 3 weeks. The expression of GFP in PC12 cells was investigated by flow cytometry and fluorescence microscopy.

Figure 11A:
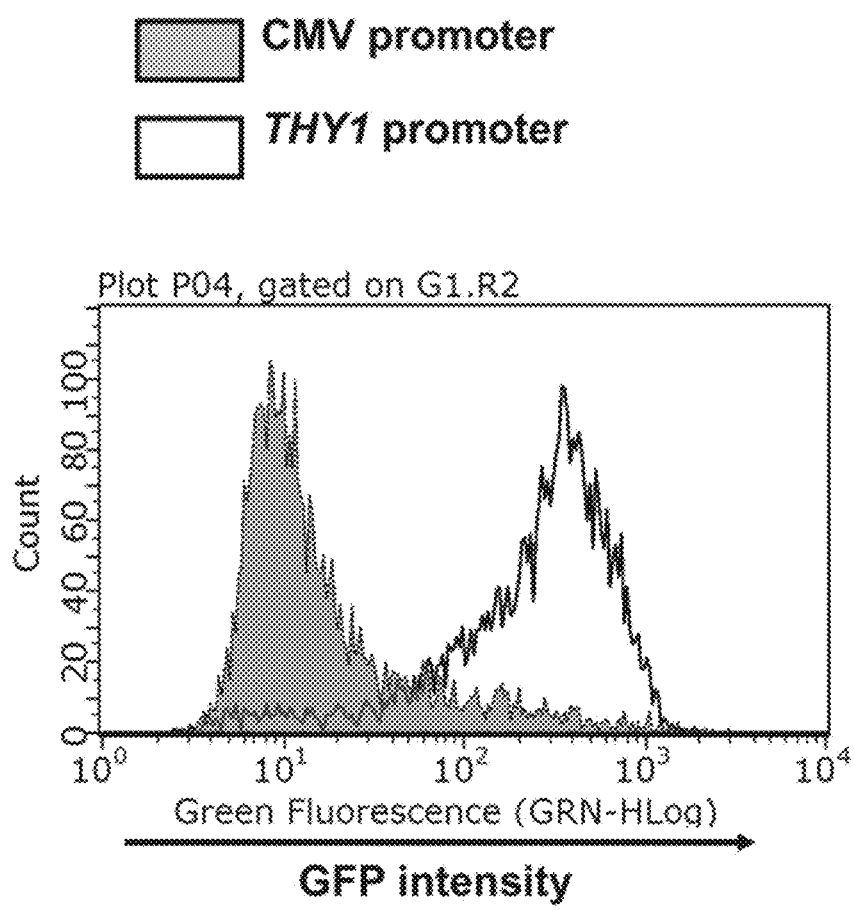
FIG. 11A is a graph in which the degree of expression of GFP in PC12 cells was analyzed.
Figure 11B:
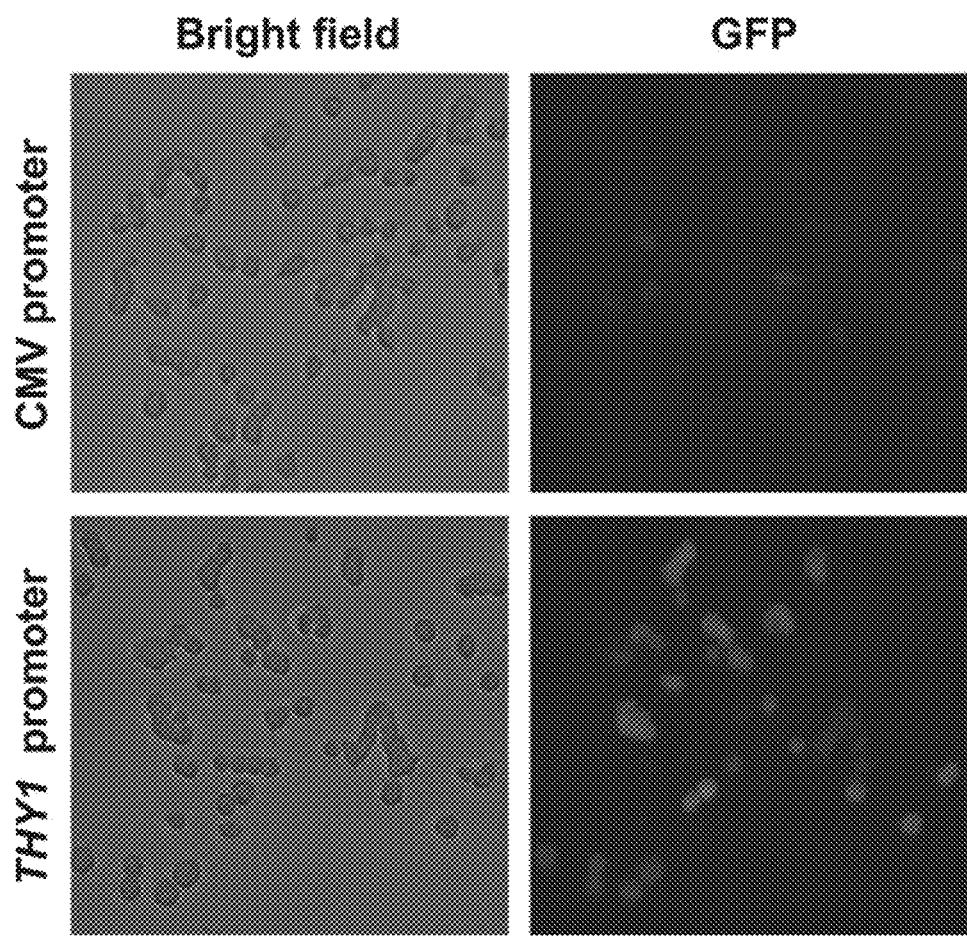
FIG. 11B is a photograph illustrating the degree of expression of GFP in PC12 cells.

FIG. 11A is a graph in which the degree of expression of GFP in PC12 cells was analyzed, and FIG. 11B is a photograph illustrating the degree of expression of GFP in PC12 cells.

Referring to FIG. 11A, the expression of GFP under the control of the Thy1 promoter is markedly higher than the expression of GFP under the control of the CMV promoter.

Example 7: Luciferase Reporter Analysis for Analysis of Important Sites in the Activity of the Thy1 Promoter In order to investigate the location of sequence inducing neuronal-specific expression in the sequence of the −4858 to −2279 Thy1 promoter, a region close to −4858 was excised to PCR-synthesize −3880/−2279, −3380/−2279, −2880/−2279 Thy1 promoter site. After cutting it with SacI/NheI restriction enzyme, it was cloned into pGL4.10[luc2].

Figure 12:
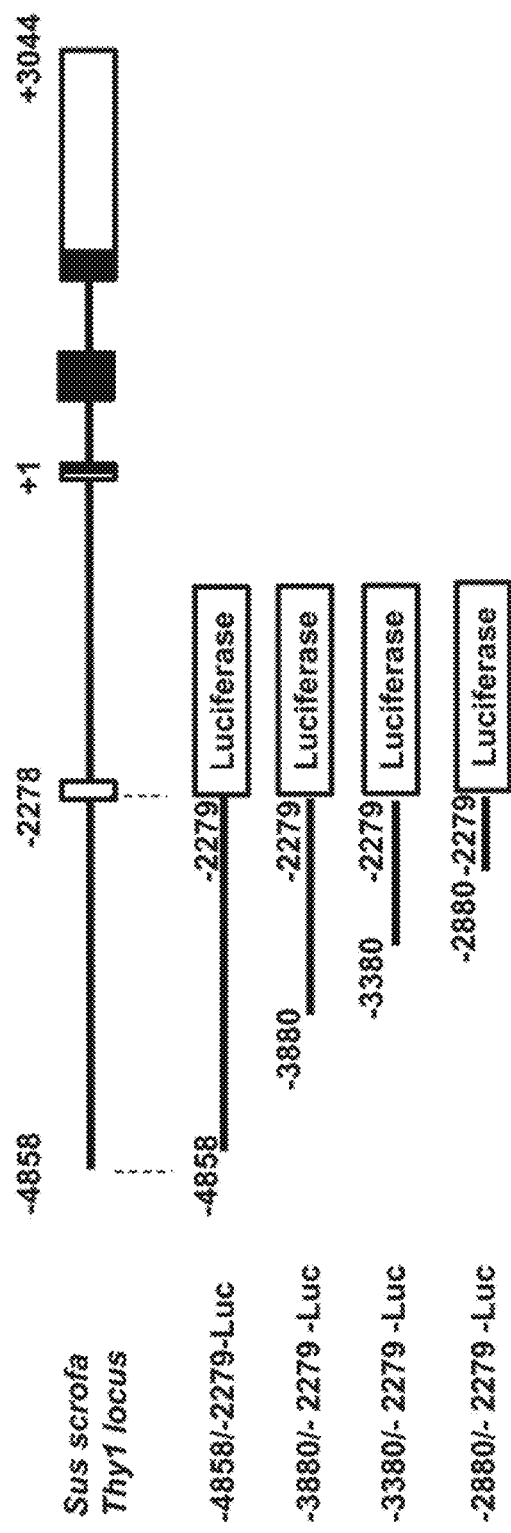
FIG. 12 illustrates the Thy1 promoter region of the luciferase reporter vector.

FIG. 12 illustrates the Thy1 promoter site of a luciferase reporter vector.

After luciferase reporter vector (500 ng) and pRL-TK (50 ng) were transfected with lipofectamin 2000 in 293T and PC12 cells, luciferase assay was performed.

Figure 13:
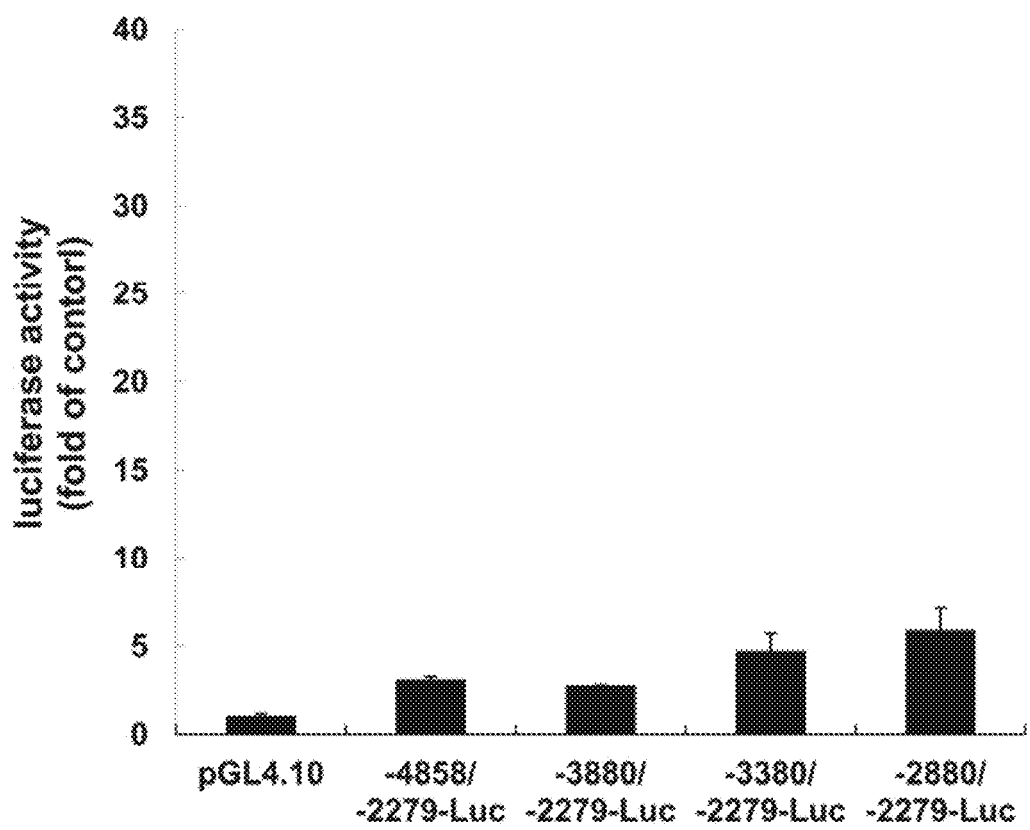
FIG. 13 is a graph illustrating the activity after transfection of each vector into 293T cells.
Figure 14:
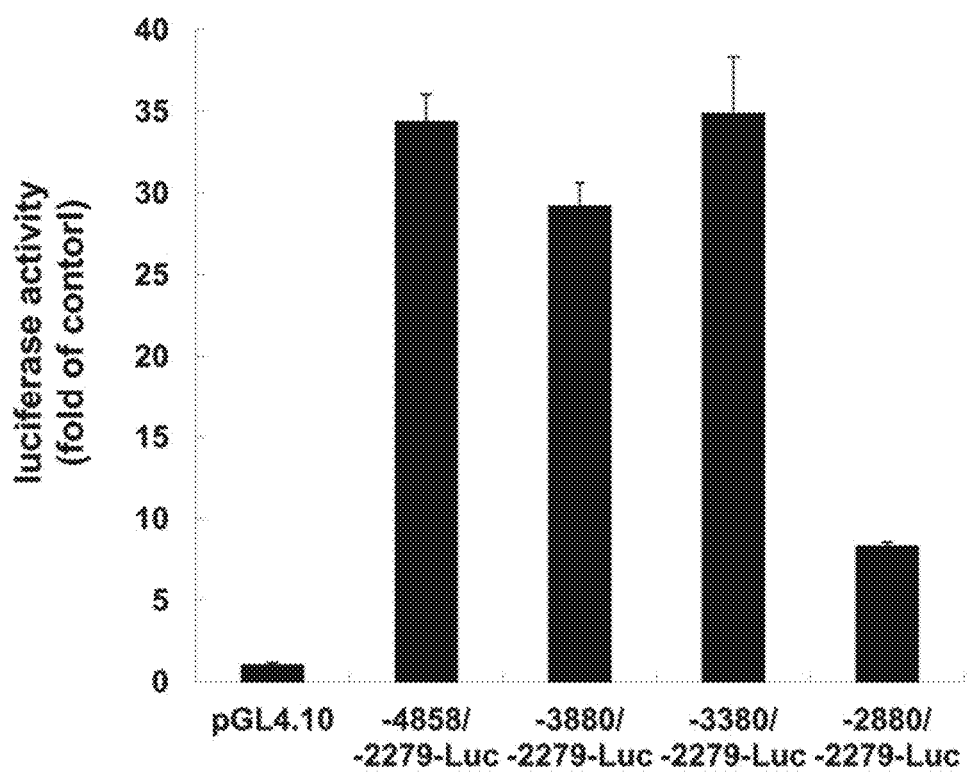
FIG. 14 is a graph illustrating the activity after transfection of each vector into PC12 cells.

FIG. 13 is a graph illustrating the activity after transfection of each vector into 293T cells, and FIG. 14 is a graph illustrating the activity after transfection of each vector into PC12 cells.

Referring to FIG. 13, it was analyzed that the activity of a promoter was low in 293T cells. On the contrary, referring to FIG. 14, the activity of the Thy1 promoter was very high in the case of −4858/−2279-Luc, −3880/−2279-Luc and −3380/−2279-Luc in the PC12 neuronal cell line; however, in the case of −2880/−2279-Luc, the activity of a promoter was remarkably decreased. That is, it indicates that the DNA sequence of about 500 bp from −3380 to −2880 of the Thy1 promoter inducing neuronal-specific expression is important.

Example 8: Completion of pTet Retrovirus Multi-Systronic Vector into which Alzheimer's Disease Gene is Introduced The retroviral vector pTet-CKOS was used to remove the TRE minimal CMV promoter and CKOS gene cluster present in this vector. It was modified to a vector having restriction enzyme sites such as SwaI, ClaI, PacI, and NotI so as to be advantageous for gene cloning.

In order to induce amino acid mutations of the precursor protein (APP) gene (NM_201414.2), the precenillin (PS-1) gene (NM_000021.3) and the Tau gene (NM_016834.4) of the Alzheimer's disease mutant gene β-amyloid, a site-directed mutagenesis kit (Stratagene) was used. In the case of APP. APP695 type gene expressed in brain cells was used and two double mutations were introduced at 595 and 596 in which a familial mutation of the gene of Alzheimer's disease was found. These mutations are known to produce more β-amyloid 42 forms. The amino acid mutations were named K595N and N596M, respectively. Two amino acid mutations were also introduced in the presenilin. Mutations of amino acids 146 and 286 were introduced and named as M146L and P286L, respectively. In the case of Tau, only one amino acid at the 243th position was mutated and named P243L.

The three genes were transcribed into a single mRNA and then linked to each other in a 2A sequence so that they were separated into independent peptides when translated into proteins, respectively.

Finally, a 1079 bp-sized Thy1 promoter was inserted into the retroviral vector using two of SwaI and ClaI restriction enzymes, followed by completion of a final recombinant expression vector, pTet-porcine TYH1 pro-APPsw-2A-TAU-2A-PS1-SV40 pA, in which three mutant genes were linked in a tandem. The complete recombinant expression vector was confirmed to have a total DNA sequence of 13,874 bp after base sequencing.

SEQ ID NO: 12 exhibits the base sequence (13.874 bp) of the above-mentioned complete recombinant expression vector.

Figure 15:
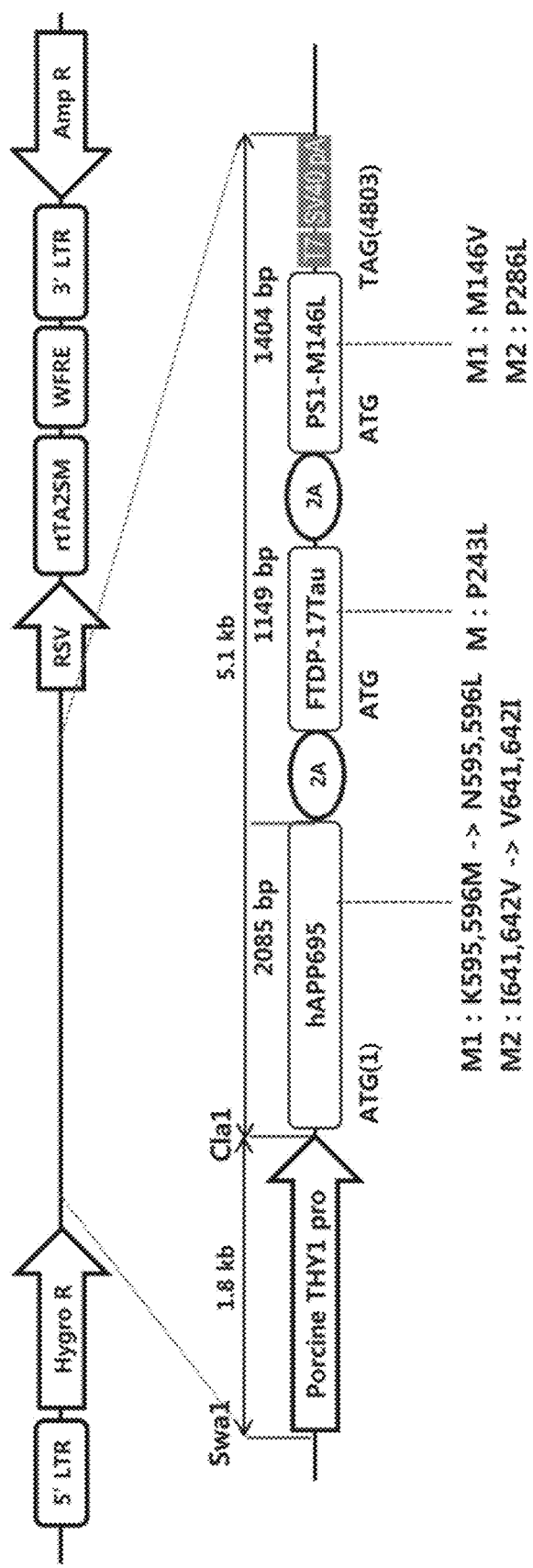
FIG. 15 is a schematic diagram illustrating a one-dimensional structure of a multi-systolic vector of pTet retrovirus prepared so that hAPP, hTau and PSEN1 genes are expressed using a Thy1 promoter.
Figure 16:
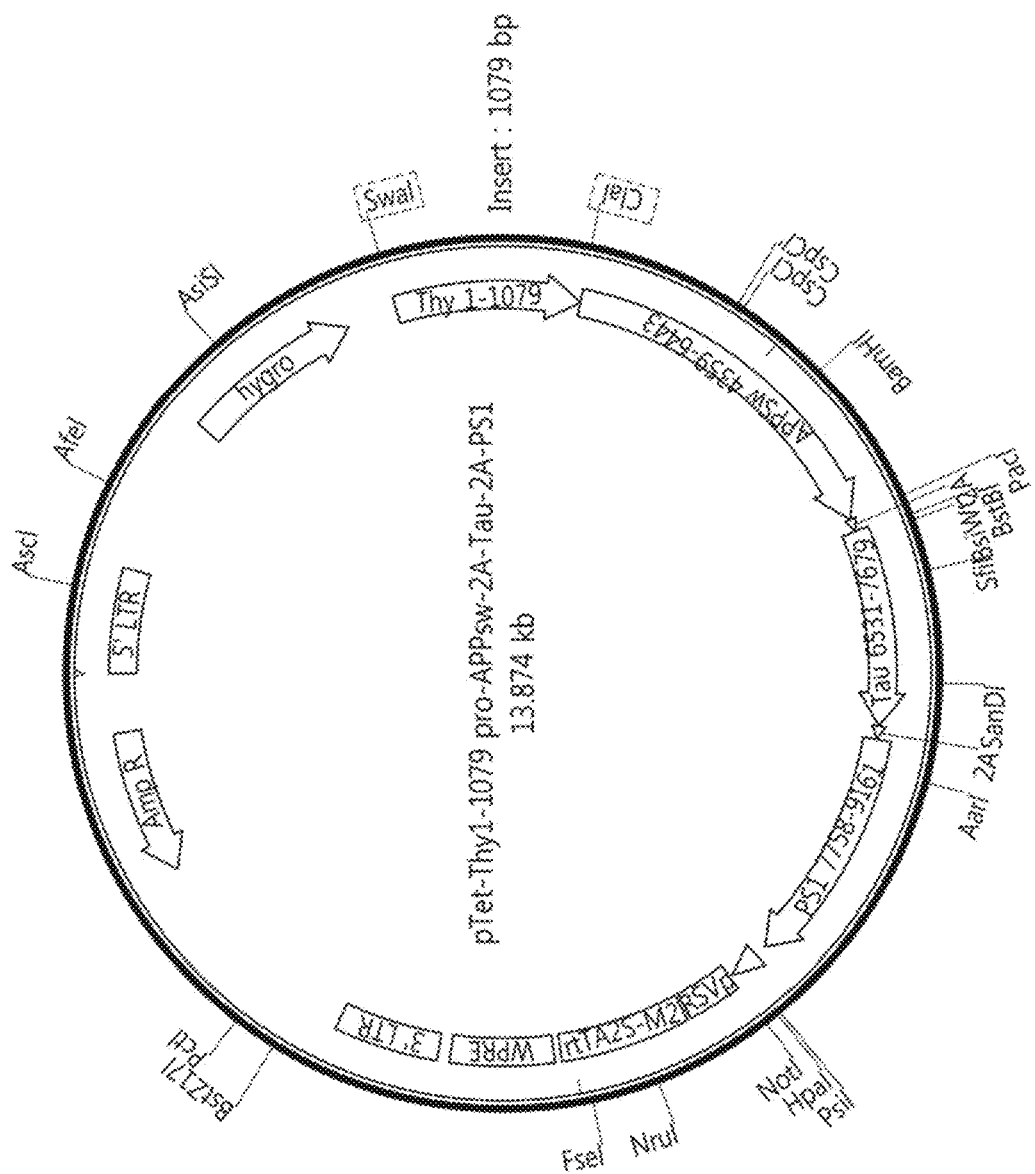
FIG. 16 is a schematic diagram illustrating a cyclic structure of a multi-systolic vector of pTet retrovirus prepared so that hAPP, hTau and PSEN1 gene are expressed using a Thy1 promoter.

FIG. 15 illustrates a one-dimensional structure of a multi-systolic vector of pTet retrovirus prepared to express hAPP, hTau and PSEN1 genes using a Thy1 promoter, and FIG. 16 illustrates a cyclic structure thereof.

While the examples as above have been described with reference to the limited examples and drawings, it will be understood by a person having ordinary skill in the pertinent technical field that various changes and modifications may be made. For example, suitable results may be achieved if the described techniques are performed in a different order than the described methods, and/or if the described constituents are linked or combined in other ways than the described methods, or are replaced or substituted by other constituents or their equivalents.

Therefore, other implementations, other embodiments, and other equivalents are also within the scope of the following claims.

-continued

| Segyebce list Free Text | |
|---|---|
| gaagccacaa ggatgcaaat caatcaaata aacctttgtt caaaaaaatt tatctcacct | 60 |
| gtgagtggga gagacaagtc accccagggc ttctggtgac ttcaaattga tagggagaaa | 120 |
| atggttgccc cagggatta aaagcttggt atctgctact cctttagagt tggcctgtct | 180 |
| cctccacttt cccacaattc caccatttcc ccctcccact gggctgggat gcagctgtgg | 240 |
| agtggctcag ctccaaggac tagggctcc acagcccagg tccggcggcc agccctccca | 300 |
| cttccagcct ggaagtggga tggggagtgg gatgagatga accggcaga ttgtagccac | 360 |
| agatgtggat gtgcagggtc cagcacaggg cttgggtgag gagggcggca ccccatccct | 420 |
| tgtctgaaga ccaagcagac agtactcagg acttgggagg gggttggggg aggaggagtg | 480 |
| catgaaactg agaagaacct | |

SEQ ID NO: 2
gaagccacaa ggatgcaaat

SEQ ID NO: 3
aggttcttct cagtttcatg

SEQ ID NO: 4

| tctagatggg gcaactggag atgatgggag aagaaagcct aagggactaa gaggaaagcc | 60 |
|---|---|
| acaatctgtc ggtaaatcct gccttgggta gaatcttcta aacctttccc gctttcagca | 120 |
| ctcttatcct gtcccacagg caaaggggag ttttaaatc tcctctccat caccatcttg | 180 |
| tgttccgccc tggttcctaa ttgtcttact tgagccattc actccatcca gccgagacct | 240 |
| tgttttagca gacacacaac cgcctagagt ctacacgccc ctccctttcc caaactaaag | 300 |
| tgcttaggga cccagaaaat aggccaggtc ctcgtaacct tatcgaaata gcacagctag | 360 |
| gccttccacc caacaacact cagagactgg gccatagggt aggaaacagc atccagagtc | 420 |
| ttgtccagac agagcccaga catcttctgt agttaagagc cctctgggta ttctcacgtc | 480 |
| ctgccccaaa aaaaggaacc aagcttatct ggggcggtg gggagaaggg ggtgtaagcc | 540 |
| aaagctaaag caactaaagc aactgtgttc tgataggaaa gatccctgga ctgagaacaa | 600 |
| gaaagctgtt ccgcaggaaa gaacacactg cgtggagtgt cagggaggag gccagccacct | 660 |
| ctggaatgcg gcaggaagat gaatgggaaa gatgaggtgg tggtggaggg cagcagccag | 720 |
| ggccttcaaa atcatcctcc agacaatgac aagcccggtc acctgatctg tgaagaggga | 780 |
| tggtctgcaa tctccaggcc ctcgagcctg tgcaagggc aggctcaggc agctctgctg | 840 |
| ctagactaag gacatcccag gtgggcacgg agagctgcat ttctcgtaaa gcgccctagg | 900 |
| agcttctgtt gttcaccaga accacgagcc cctggactgg accgtccaca aggctcgttc | 960 |
| cagttagaaa attccatcac tctaagagct gggaggcacc taacctccaa gggagggaga | 1020 |
| gggaagtgga tctcccactt gccagcccag ggatgacttc caacagtgcc attacagtaa | 1080 |
| tggaaactgc agtgaaggtg ccagggctga cttctgtgaa gaaagaggag gacaggagtt | 1140 |
| ccccctagtgg ctcatcagaa atgaatctga ctagcatcca tgaggatgca ggttcaatcc | 1200 |
| ctggcctcat tcagtggctt aaggatccag cgttgccgag agctgtgatg taggtcacag | 1260 |
| acgcggctca gatcccgtgt tgctgttgct gtggctgtgg cataggtcag aagcgacagc | 1320 |
| tctgatttga cccctaacct gggaacctcc atatcccgct agtgcggccc ttaaaagaca | 1380 |
| aaaagaagga aaagagaaga aaagacatag gcgaacagaa aggcagatga cagggtggca | 1440 |
| gggccagcct acacgatggc ccgaccagaa ttcacaaaga agccacaagg atgcaaatca | 1500 |
| atcaaataaa cctttgttca aaaaaattta tctcacctgt gagtgggaga gacaagtcac | 1560 |

-continued

| | |
|---|---|
| cccagggctt ctggtgactt caaattgata gggagaaaat ggttgcccca ggggattaaa | 1620 |
| agcttggtat ctgctactcc tttagagttg gcctgtctcc tccactttcc cacaattcca | 1680 |
| ccatttcccc ctcccactgg gctgggatgc agctgtggag tggctcagct ccaaggacta | 1740 |
| ggggctccac agcccaggtc cggcggccag ccctcccact tccagcctgg aagtgggatg | 1800 |
| gggagtggga tgagatgaac ccggcagatt gtagccacag atgtggatgt gcagggtcca | 1860 |
| gcacagggct tgggtgagga gggcggcacc ccatcccttg tctgaagacc aagcagacag | 1920 |
| tactcaggac ttgggagggg gttggggag gaggagtgca tgaaactgag aagaaccttc | 1980 |
| tagctgcctg cgccaggagg tacccgggag ctgaaggaga tggagtgccc cagagcagaa | 2040 |
| agcccctgca ggtctggatg ttctaggctg gatgaggggg cgaggcaggc ctggggacct | 2100 |
| gggaagacca ggcgcagtac ctgccttgct tctgaaaatg ctgctccaac gtggaaaaac | 2160 |
| actcccacca tctttctttg gagaaagcct gtaatattcc aacaccaaaa cctctcacta | 2220 |
| gaggttcccg tggagaiggg ttccagatga aagggaagg aggaggcatg ggcgctgcct | 2280 |
| aacctccatc ctccattcct taccccctctc ccaccggctt ctgaagccgg ggtcagaaga | 2340 |
| aagggttaaa gccttaaaag gggaccgatt ttgcggggct ctggggggtcg gctggcacac | 2400 |
| cctgagcggc cccgcccttc tctctagtgt ccagaaccct ccctgccctg cccaggccta | 2460 |
| acggccacag ggggagggcc ccccctttact gcagaccgcc actctcccac accaatatcg | 2520 |
| gaccgcctcc tcctccctct gccaccccttt ctcgctcccc actcagcctc tgattggcc | |

SEQ ID NO: 5
tctagatggg gcaactggag

SEQ ID NO: 6
ggccaatcag aggctgagtg

SEQ ID NO: 7

| | |
|---|---|
| tctagatggg gcaactggag atgatgggag aagaaagcct aagggactaa gaggaaagcc | 60 |
| acaatctgtc ggtaaatcct gccttgggta gaatcttcta aacctttccc gctttcagca | 120 |
| ctcttatcct gtcccacagg caaaggggag tttttaaatc tcctctccat caccatcttg | 180 |
| tgttccgccc tggttcctaa ttgtcttact tgagccattc actccatcca gccgagacct | 240 |
| tgttttagca gacacacaac tgcctagagt ctacacgccc ctccctttcc caaactaaag | 300 |
| tgcttaggga cccagaaaat aggccaggtc ctcgtaacct tatcgaaata gcacagctag | 360 |
| gccttccacc caacaacact cagagactgg gccataggt aggaaacagc atccagagtc | 420 |
| ttgtccagac agagcccaga catcttctgt agttaagagc cctctgggta ttctcacgtc | 480 |
| ctgccccaaa aaaaggaacc aagcttatct ggggcggtg gggagaaggg ggtgtaagcc | 540 |
| aaagctaaag caactaaagc aactgtgttc tgataggaaa gatccctgga ctgagaacaa | 600 |
| gaaagctgtt ccgcaggaaa gaacacactg cgtggagtgt cagggaggag gccagcacct | 660 |
| ctggaatgcg gcaggaagat gaatgggaaa gatgaggtgg tggtggaggg cagcagccag | 720 |
| ggccttcaaa atcaCcctcc agacaatgac aagcccggtc acctgatctg tgaagaggga | 780 |
| tggtctgcaa tctccaggcc ctcgagcctg tgcaaagggc aggctcaggc agctctgctg | 840 |
| ctagactaag gacatcccag gtgggcacgg agagctgcat ttctcgtaaa gcgccctagg | 900 |
| agcttctgtt gttcaccaga accacgagcc cctggactgg accgttcaca aggctcgttc | 960 |
| cagttagaaa attccatcac tctaagagct gggaggcacc taacctccaa gggagggaga | 1020 |
| gggaagtgga tctcccactt gccagcccag ggatgacttc caacagtgcc attacagtaa | 1080 |

-continued

| Sequence list Free Text |
|---|

```
tggaaactgc agtgaaggtg ccagggctga cttctgtgaa gaaagaggag gacaggagtt   1140
cccctagtgg ctcatcagaa atgaatctga ctagcatcca tgaggatgca ggttcaatcc   1200
ctggcctcat tcagtggctt aaggatccag cgttgccgag agctgtgatg taggtcacag   1260
acgcggctca gatcccgtgt tgctgttgct gtggctgtgg cataggtcag aagcgacagc   1320
tctgatttga cccctaacct gggaacctcc atatcccgct agtgcggccc ttaaaagaca   1380
aaaagaagga aaagagaaga aaagacatag gcgaacagaa aggcagatga cagggtggca   1440
gggccagcct acacgatggc ccgaccagaa ttcacaaaga agccacaagg atgcaaatca   1500
atcaaataaa cctttgttca aaaaaattta tctcacctgt gagtgggaga gacaagtcac   1560
cccagggctt ctggtgactt caaattgata gggagaaaat ggttgcccca ggggattaaa   1620
agcttggtat ctgctactcc tttagagttg gcctgtctcc tccactttcc cacaattcca   1680
ccatttcccc ctcccactgg gctgggatgc agctgtggag tggctcagct ccaaggacta   1740
ggggctccac agcccaggtc cggcggccag ccctcccact tccagcctgg aagtgggatg   1800
gggagtggga tgagatgaac ccggcagatt gtagccacag atgtggatgc gcagggtcca   1860
gcacagggct tgggtgagga gggcggcacc ccatcccttg tctgaagacc aagcagacag   1920
tactcaggac ttgggagggg gttggggag gaggagtgca tgaaactgag aagaaccttc   1980
tagctgcctg cgccaggagg tacccgggag ctgaaggaga tggagtgccc cagagcagaa   2040
agcccctgca ggtctggatg ttctaggctg gatgaggggg cgaggcaggc ctggggacct   2100
gggaagacca ggcgcagtac ctgccttgct tctgaaaatg ctgctccaac gtggaaaaac   2160
actcccacca tctttctttg gagaaagcct gtaatattcc aacaccaaaa cctctcacta   2220
gaggttcccg tggagatggg ttccagatga aagggaagg aggaggcatg ggcgctgcct   2280
aacctccatc ctccattcct taccccctctc ccaccggctt ctgaagccgg ggtcagaaga   2340
aagggttaaa gccttaaaag gggaccgatt ttgcggggct ctgggggtcg gctggcacac   2400
cctgagcggc cccgccttc tctctagtgt ccagaaccct ccctgccctg cccaggccta   2460
acggccacag ggggagggcc cccctttact gcagaccgcc actctcccac accaatatcg   2520
gaccgcctcc tcctccctct gccaccccttc tcgctcccc actcagcctc tgattggcc
```

SEQ ID NO: 8

```
aacctccatc ccccattcct taccccctctc ccaccggctt ctgaagccgg ggtcagaaga     60
aagggttaaa gccttaaaag gggaccgatt ttgcggggct ctgggggtcg gctggcacac    120
cctgagcggc cccgccttc tctctagtgt ccagaaccct ccctgccctg cccaggccta    180
acggccacag ggggagggcc cccctttact gcagaccgcc actctcccac accaatatcg    240
gaccgcctcc tcctccctct gccaccccttc tcgctcccc actcagcctc tgattggccg    300 agccccccggg tcctccccgc ccctcctctc ccacccttgg tgaaaactgc gggtgccggg    360
cagggtgcag caactggagg cggcggcgtg tccggagcag tctgcggcgg cgagggaccg    420
gaacccaggt gggaactgga gccagggcgg ggcccggagc gccctcggtg cccctgcaag    480
ctctccagac cccaagcttc agaaaaccat ccgagggcgc tcagggaagg agcagtgcag    540
ggcctgggga ggggtctgct tcccaggcag gggcgggagc cggacgccaa ggctgcaggc    600
cgggggccgc aacgcatctt tcgcccgctc ggaggacgtt tgcctggggc ggggcgctg    660 gaggagaact gggaggaagg gcgccaagga cagttttggg ttctgctcgc cacccacaca    720
tccccaagcc ccgcttgcaa agacagggggc ggggggcgac gaaactcggg ggagagaacc    780
```

-continued

| Segyebce list Free Text | |
|---|---|
| gaggacccca aactagaggg aatctctgcc ctccgacctc gcgacaggct gggtgcgggg | 840 |
| catccaagga acgggaaacc gcagtgccgc gggcggggac tgggaggaag gcaggcagac | 900 |
| gggggaggcg agaactggaa aaggatgaga gaggggaag ggggacttca attgggaatg | 960 |
| gaggagattg gaatggggag acggaataag ggtggggtta gtcgaacgcg tgctgagagg | 1020 |
| gagggaacgc aaagcttctg cgggttctga gctgcgggga cccaggaaac gaaaacagac | 1080 |
| tgcgcctccc ctaccagctg tctacccctc cctttggctc tccatcccct gccagcccca | 1140 |
| gccccgtttc ttcctttcta cccctccctc tcctggatcc cgagctcaca ctcctcctct | 1200 |
| gtaactcagc gtccgctaat caaaaccaga tgtcagtccc cctttcttcc ccagcagcac | 1260 |
| ctccgggtcc ctctcggcag gggtctggga aggagttgac tgcgtccgcg ggcgccgcag | 1320 |
| taccccagcc tcgcccctcc ctccccacct ctgggagctg ggctgaacgc ctgggaccct | 1380 |
| ggaagccgcg agtcgcgcgc cctgcgcacc cggccgaccc cctcctgtg gcctctccct | 1440 |
| ggagaactcc gctgcggaca ggctaggcta cctgctctgt gtctccctgc cagaatattg | 1500 |
| attcagccta ggctgcaaaa ataagacagg gcagagaacc taggcaggga ggctatggaa | 1560 |
| gccaaactgg aaaactgcaa gcccaagaat tcctcctgga gagctagaga attggaaagg | 1620 |
| tcttggttcc aaggcagaga acacatgcac gcatttgcaa taggacagca ctgccgtttt | 1680 |
| cctcacaccc ttcgctgtgg gccaagtaca atcctacctg ggccccaca catacctgac | 1740 |
| gtcatccctg gccacacagt catctaagag aaaggaaatt aatgtttgtg gatcacttac | 1800 |
| ttacagtgcc aaatgtttgt cattttctt aacctccatc acggcccgt gctatgtatc | 1860 |
| taaagcccag tttcgttcag tatctttcag gcatctgtta tctgccagaa aggtctggcc | 1920 |
| atcgggatt ttcttctgaa tacgaaatag gaagtctttg tttaacaggt agagcgtttt | 1980 |
| agttttgcag gatgtcaaga gttctggaaa ttggttgcac cacaatgtaa atgaacttaa | 2040 |
| cacttctgaa ctgtacactt aaaaatggtt taggagagga gttccctggt ggcctgggag | 2100 |
| ttaagaacta ggcattgtca ctgctgtggc tcaggtttga ccctggctgg ggaaattctg | 2160 |
| catgccacag gcacagcccc gccaaaaatg gttataataa taaatgttat gttctgcgaa | 2220 |
| ttttactaaa aaataggaag tccctatctt cctgaaggga agaggaagtg gtaatttcaa | 2280 |
| gacacttact caaagtcacc caactagcaa gcattcagca cagatacccca ccaccaaagg | 2340 |
| gtatgttctc catccctctt gctttctctg actgggaaga gccgagtgtc tgtcacattc | 2400 |
| actgagaggt gggaggggag agggctacag agaggggctt ggatgccccc catgccatt | 2460 |
| atggcatgtc tcccaggggc ccccaggcct ggcagcaaat gtgggcacac ctgccccgcc | 2520 |
| tcttggctga ttcccacc | |

SEQ ID NO: 9
| ggcctaactg gccggtacct gagctcgcta gcctcgagga tatcaagatc tggcctcggc | 60 |
| ggccaagctt ggcaatccgg tactgttggt aaagccacca tggaagatgc caaaaacatt | 120 |
| aagaagggcc cagcgccatt ctacccactc gaagacggga ccgccggcga gcagctgcac | 180 |
| aaagccatga gcgctacgc cctggtgccc ggcaccatcg cctttaccga cgcacatatc | 240 |
| gaggtggaca ttacctacgc cgagtacttc gagatgagcg ttcggctggc agaagctatg | 300 |
| aagcgctatg gctgaatac aaaccatcgg atcgtggtgt gcagcgagaa tagcttgcag | 360 |
| ttcttcatgc ccgtgttggg tgccctattc atcggtgtgg ctgtggcccc agctaacgac | 420 |
| atctacaacg agcgcgagct gctgaacagc atgggcatca gccagcccac cgtcgtattc | 480 |

| | |
|---|---|
| gtgagcaaga aagggctgca aaagatcctc aacgtgcaaa agaagctacc gatcatacaa | 540 |
| aagatcatca tcatggatag caagaccgac taccagggct tccaaagcat gtacaccttc | 600 |
| gtgacttccc atttgccacc cggcttcaac gagtacgact tcgtgcccga gagcttcgac | 660 |
| cgggacaaaa ccatcgccct gatcatgaac agtagtggca gtaccggatt gcccaagggc | 720 |
| gtagccctac cgcaccgcac cgcttgtgtc cgattcagtc atgcccgcga ccccatcttc | 780 |
| ggcaaccaga tcatccccga caccgctatc ctcagcgtgg tgccatttca ccacggcttc | 840 |
| ggcatgttca ccacgctggg ctacttgatc tgcggctttc gggtcgtgct catgtaccgc | 900 |
| ttcgaggagg agctattctt gcgcagcttg caagactata agattcaatc tgccctgctg | 960 |
| gtgcccacac tatttagctt cttcgctaag agcactctca tcgacaagta cgacctaagc | 1020 |
| aacttgcacg agatcgccag cggcggggcg ccgctcagca aggaggtagg tgaggccgtg | 1080 |
| gccaaacgct tccacctacc aggcatccgc cagggctacg gcctgacaga aacaaccagc | 1140 |
| gccattctga tcacccccga aggggacgac aagcctggcg cagtaggcaa ggtggtgccc | 1200 |
| ttcttcgagg ctaaggtggt ggacttggac accggtaaga cactgggtgt gaaccagcgc | 1260 |
| ggcgagctgt gcgtccgtgg ccccatgatc atgagcggct acgttaacaa ccccgaggct | 1320 |
| acaaacgctc tcatcgacaa ggacggctgg ctgcacagcg gcgacatcgc ctactgggac | 1380 |
| gaggacgagc acttcttcat cgtggaccgg ctgaagagcc tgatcaaata caagggctac | 1440 |
| caggtagccc cagccgaact ggagagcatc ctgctgcaac accccaacat cttcgacgcc | 1500 |
| ggggtcgccg gcctgcccga cgacgatgcc ggcgagctgc cgccgcagt cgtcgtgctg | 1560 |
| gaacacggta aaaccatgac cgagaaggag atcgtggact atgtggccag ccaggttaca | 1620 |
| accgccaaga agctgcgcgg tggtgttgtg ttcgtggacg aggtgcctaa aggactgacc | 1680 |
| ggcaagttgg acgcccgcaa gatccgcgag attctcatta aggccaagaa gggcggcaag | 1740 |
| atcgccgtgt aataattcta gagtcggggc ggccggccgc ttcgagcaga catgataaga | 1800 |
| tacattgatg agtttggaca aaccacaact agaatgcagt gaaaaaaatg ctttatttgt | 1860 |
| gaaatttgtg atgctattgc tttatttgta accattataa gctgcaataa acaagttaac | 1920 |
| aacaacaatt gcattcattt tatgtttcag gttcaggggg aggtgtggga ggttttttaa | 1980 |
| agcaagtaaa acctctacaa atgtggtaaa atcgataagg atccgtcgac cgatgccctt | 2040 |
| gagagccttc aacccagtca gctccttccg gtgggcgcgg ggcatgacta tcgtcgccgc | 2100 |
| acttatgact gtcttcttta tcatgcaact cgtaggacag gtgccggcag cgctcttccg | 2160 |
| cttcctcgct cactgactcg ctgcgctcgg tcgttcggct gcggcgagcg gtatcagctc | 2220 |
| actcaaaggc ggtaatacgg ttatccacag aatcagggga taacgcagga agaacatgt | 2280 |
| gagcaaaagg ccagcaaaag gccaggaacc gtaaaaaggc cgcgttgctg gcgttttttcc | 2340 |
| ataggctccg cccccctgac gagcatcaca aaaatcgacg ctcaagtcag aggtggcgaa | 2400 |
| acccgacagg actataaaga taccaggcgt ttccccctgg aagctccctc gtgcgctctc | 2460 |
| ctgttccgac cctgccgctt accggatacc tgtccgcctt tctcccttcg ggaagcgtgg | 2520 |
| cgctttctca tagctcacgc tgtaggtatc tcagttcggt gtaggtcgtt cgctccaagc | 2580 |
| tgggctgtgt gcacgaaccc cccgttcagc ccgaccgctg cgccttatcc ggtaactatc | 2640 |
| gtcttgagtc caacccggta agacacgact tatcgccact ggcagcagcc actggtaaca | 2700 |
| ggattagcag agcgaggtat gtaggcggtg ctacagagtt cttgaagtgg tggcctaact | 2760 |
| acggctacac tagaagaaca gtatttggta tctgcgctct gctgaagcca gttaccttcg | 2820 |

| | | | | |
|---|---|---|---|---|
| gaaaaagagt | tggtagctct | tgatccggca | aacaaaccac | cgctggtagc ggtggttttt | 2880 |
| ttgtttgcaa | gcagcagatt | acgcgcagaa | aaaaaggatc | tcaagaagat cctttgacct | 2940 |
| tttctacggg | gtctgacgct | cagtggaacg | aaaactcacg | ttaagggatt ttggtcatga | 3000 |
| gattatcaaa | aaggatcttc | acctagatcc | ttttaaatta | aaaatgaagt tttaaatcaa | 3060 |
| tctaaagtat | atatgagtaa | acttggtctg | acagcggccg | caaatgctaa accactgcag | 3120 |
| tggttaccag | tgcttgatca | gtgaggcacc | gatctcagcg | atctgcctat ttcgttcgtc | 3180 |
| catagtggcc | tgactccccg | tcgtgtagat | cactacgatt | cgtgagggct taccatcagg | 3240 |
| ccccagcgca | gcaatgatgc | cgcgagagcc | gcgttcaccg | gcccccgatt tgtcagcaat | 3300 |
| gaaccagcca | gcagggaggg | ccgagcgaag | aagtggtcct | gctactttgt ccgcctccat | 3360 |
| ccagtctatg | agctgctgtc | gtgatgctag | agtaagaagt | tcgccagtga gtagtttccg | 3420 |
| aagagttgtg | gccattgcta | ctggcatcgt | ggtatcacgc | tcgtcgttcg gtatggcttc | 3480 |
| gttcaactct | ggttcccagc | ggtcaagccg | ggtcacatga | tcacccatat tatgaagaaa | 3540 |
| tgcagtcagc | tcctcagggc | ctccgatcgt | tgtcagaagt | aagttggccg cggtgttgtc | 3600 |
| gctcatggta | atggcagcac | tacacaattc | tcttaccgtc | atgccatccg taagatgctt | 3660 |
| ttccgtgacc | ggcgagtact | caaccaagtc | gttttgtgag | tagtgtatac ggcgaccaag | 3720 |
| ctgctcttgc | ccggcgtcta | tacgggacaa | caccgcgcca | catagcagta ctttgaaagt | 3780 |
| gctcatcatc | gggaatcgtt | cttcggggcg | gaaagactca | aggatcttgc cgctattgag | 3840 |
| atccagttcg | atatagccca | ctcttgcacc | cagttgatct | tcagcatctt ttactttcac | 3900 |
| cagcgtttcg | gggtgtgcaa | aaacaggcaa | gcaaaatgcc | gcaaagaagg gaatgagtgc | 3960 |
| gacacgaaaa | tgttggatgc | tcatactcgt | ccttttttcaa | tattattgaa gcatttatca | 4020 |
| gggttactag | tacgtctctc | aaggataagt | aagtaatatt | aaggtacggg aggtattgga | 4080 |
| caggccgcaa | taaaatatct | ttattttcat | tacatctgtg | tgttggtttt ttgtgtgaat | 4140 |
| cgatagtact | aacatacgct | ctccatcaaa | acaaaacgaa | acaaaacaaa ctagcaaaat | 4200 |
| aggctgtccc | cagtgcaagt | gcaggtgcca | gaacatttct | ct | |

SEQ ID NO: 10

| | | | | |
|---|---|---|---|---|
| tagttattaa | tagtaatcaa | ttacggggtc | attagttcat | agcccatata tggagttccg | 60 |
| cgttacataa | cttacggtaa | atggcccgcc | tggctgaccg | cccaacgacc cccgcccatt | 120 |
| gacgtcaata | atgacgtatg | ttcccatagt | aacgccaata | gggactttcc attgacgtca | 180 |
| atgggtggag | tatttacggt | aaactgccca | cttggcagta | catcaagtgt atcatatgcc | 240 |
| aagtacgccc | cctattgacg | tcaatgacgg | taaatggccc | gcctggcatt atgcccagta | 300 |
| catgacctta | tgggactttc | ctacttggca | gtacatctac | gtattagtca tcgctattac | 360 |
| catggtgatg | cggttttggc | agtacatcaa | tgggcgtgga | tagcggtttg actcacgggg | 420 |
| atttccaagt | ctccacccca | ttgacgtcaa | tgggagtttg | ttttggcacc aaaatcaacg | 480 |
| ggactttcca | aaatgtcgta | acaactccgc | cccattgacg | caaatgggcg gtaggcgtgt | 540 |
| acggtgggag | gtctatataa | gcagagctgg | tttagtgaac | cgtcagatcc gctagcgcta | 600 |
| ccggactcag | atctcgagct | caagcttcga | attctgcagt | cgacggtacc gcgggcccgg | 660 |
| gatccaccgg | tcgccaccat | ggtgagcaag | ggcgaggagc | tgttcaccgg ggtggtgccc | 720 |
| atcctggtcg | agctggacgg | cgacgtaaac | ggccacaagt | tcagcgtgtc cggcgagggc | 780 |
| gagggcgatg | ccacctacgg | caagctgacc | ctgaagttca | tctgcaccac cggcaagctg | 840 |

-continued

| Segyebce list Free Text | |
|---|---|
| cccgtgccct ggcccaccct cgtgaccacc ctgacctacg gcgtgcagtg cttcagccgc | 900 |
| taccccgacc acatgaagca gcacgacttc ttcaagtccg ccatgcccga aggctacgtc | 960 |
| caggagcgca ccatcttctt caaggacgac ggcaactaca agacccgcgc cgaggtgaag | 1020 |
| ttcgagggcg acaccctggt gaaccgcatc gagctgaagg gcatcgactt caaggaggac | 1080 |
| ggcaacatcc tggggcacaa gctggagtac aactacaaca gccacaacgt ctatatcatg | 1140 |
| gccgacaagc agaagaacgg catcaaggtg aacttcaaga tccgccacaa catcgaggac | 1200 |
| ggcagcgtgc agctcgccga ccactaccag cagaacaccc ccaccggcga cggccccgtg | 1260 |
| ctgctgcccg acaaccacta cctgagcacc cagtccgccc tgagcaaaga ccccaacgag | 1320 |
| aagcgcgatc acatggtcct gctggagttc gtgaccgccg ccgggatcac tctcggcatg | 1380 |
| gacgagctgt acaagtaaag cggccgcgac tctagatcat aatcagccat accacatttg | 1440 |
| tagaggtttt acttgcttta aaaaacctcc cacacctccc cctgaacctg aaacataaaa | 1500 |
| tgaatgcaat tgttgttgtt aacttgttta ttgcagctta taatggttac aaataaagca | 1560 |
| atagcatcac aaactttcaca aataaagcat ttttttcact gcattctagt tgtggtttgt | 1620 |
| ccaaactcat caatgtatct taaggcgtaa attgtaagcg ttaatatttt gttaaaattc | 1680 |
| gcgttaaatt tttgttaaat cagctcattt tttaaccaat aggccgaaat cggcaaaatc | 1740 |
| cctsataaat caaaagaata gaccgagata gggttgagtg ttgttccagt ttggaacaag | 1800 |
| agtccactat taaagaacgt ggactccaac gtcaaagggc gaaaaaccgt ctatcagggc | 1860 |
| gatggcccac tacgtgaacc atcaccctaa tcaagttttt tggggtcgag gtgccgtaaa | 1920 |
| gcactaaatc ggaaccctaa agggagcccc cgatttagag cttgacgggg aaagccggcg | 1980 |
| aacgtggcga gaaaggaagg gaagaaagcg aaaggagcgg gcgctagggc gctggcaagt | 2040 |
| gtagcggtca cgctgcgcgt aaccaccaca cccgccgcgc ttaatgcgcc gctacagggc | 2100 |
| gcgtcaggtg cacttttcg gggaaatgtg cgcggaaccc ctatttgttt attttttctaa | 2160 |
| atacactcaa atatgtatcc gctcatgaga caataaccct gataaatgct tcaataatat | 2220 |
| tgaaaaagga agagtcctga gcggaaagaa accagctgtg gaatgtgtgt cagttagggt | 2280 |
| gtggaaagtc cccaggctcc ccagcaggca gaagtatgca aagcatgcat ctcaattagt | 2340 |
| cagcaaccag gtgtggaaag tccccaggct ccccagcagg cagaagtatg caaagcatgc | 2400 |
| atctcaatta gtcagcaacc atagtcccgc ccctaactcc gcccatcccg cccctaactc | 2460 |
| cgcccagttc cgcccattct ccgccccatg gctgactaat ttttttttatt tatgcagagg | 2520 |
| ccgaggccgc ctcggcctct gagctattcc agaagtagtg aggaggcttt tttggaggcc | 2580 |
| taggcttttg caaagatcga tcaagagaca ggatgaggat cgtttcgcat gattgaacaa | 2640 |
| gasggattgc acgcaggttc tccggccgct tgggtggaga ggctattcgg ctatgactgg | 2700 |
| gcacaacaga caatcggctg ctctgatgcc gccgtgttcc ggctgtcagc gcaggggcgc | 2760 |
| ccggttcttt ttgtcaagac cgacctgtcc ggtgccctga tgaactgca agacgaggca | 2820 |
| gcgcggctat cgtggctggc cacgacgggc gttccttgcg cagctgtgct cgacgttgtc | 2880 |
| actgaagcgg gaagggactg gctgctattg ggcgaagtgc cggggcagga tctcctgtca | 2940 |
| tctcaccttg ctcctgccga gaaagtatcc atcatggctg atgcaatgcg gcggctgcat | 3000 |
| acgcttgatc cggctacctg cccattcgac caccaagcga acatcgcat cgagcgagca | 3060 |
| cgtactcgga tggaagccgg tcttgtcgat caggatgatc tggacgaaga gcatcagggg | 3120 |

| | |
|---|---:|
| ctcgcgccag ccgaactgtt cgccaggctc aaggcgagca tgcccgacgg cgaggatctc | 3180 |
| gtcgtgaccc atggcgatgc ctgcttgccg aatatcatgg tggaaaatgg ccgcttttct | 3240 |
| ggattcatcg actgtggccg gctgggtgtg gcggaccgct atcaggacat agcgttggct | 3300 |
| acccgtgata ttgctgaaga gcttggcggc gaatgggctg accgcttccc cgtgctttac | 3360 |
| ggtatcgccg ctcccgattc gcagcgcatc gccttctatc gccttcttga cgagttcttc | 3420 |
| tgagcgggac tctggggttc gaaatgaccg accaagcgac gcccaacctg ccatcacgag | 3480 |
| atttcgattc caccgccgcc ttctatgaaa ggttgggctt cggaatcgtt ttccgggacg | 3540 |
| ccggctggat gatcctccag cgcggggatc tcatgctgga gttcttcgcc caccctaggg | 3600 |
| ggaggctaac tgaaacacgg aaggagacaa taccggaagg aacccgcgct atgacggcaa | 3660 |
| taaaagaca gaataaaacg cacggtgttg ggtcgtttgt tcataaacgc ggggttcggt | 3720 |
| cccagggctg gcactctgtc gatacccac cgagacccca ttggggccaa cacgcccgcg | 3780 |
| cttcctcctt ttccccaccc caccccccaa gttcgggtga aggcccaggg ctcgcagcca | 3840 |
| acgtcggggc ggcaggccct gccatagcct caggttactc atatatactt tagattgatt | 3900 |
| taaaacttca ctcttaatttt aaaaggatct aggtgaagat cccttctgat aatctcatga | 3960 |
| ccaaaatccc ctaacgtgag tcttcgctcc actgagcgtc agaccccgta gaaaagatca | 4020 |
| aaggatcttc ttgagatcct ttttttctgc gcgtaatctg ctgcctgcaa acaaaaaaac | 4080 |
| caccgctacc agcggtggct tgtttgccgg atcaagagct accaactctt cttccgaagg | 4140 |
| taactggcct cagcagagcg cagataccaa atactgtcct tctagtgtag ccgtagctag | 4200 |
| gccaccactt caagaactct gtagcaccgc ctacatacct cgctctgcta atcctgctac | 4260 |
| cagtggctgc tgccagtggc gataagtcgt gtcttaccgg gttggactca agacgatagt | 4320 |
| taccggataa ggcgcagcgg tcgggccgaa cggggggttc gtgcacacag cccagcctgg | 4380 |
| agcgaacgac ctacaccgaa ctgagatacc tacagcgtga gctatgagaa agcgccacgc | 4440 |
| ctcccgaagg gagaaaggcg gacaggtatc cggtaagcgg cagggtcgga acaggagagc | 4500 |
| gcacgaggga gcctccaggg ggaaacgcct ggtatcctta tagtcctgtc gggtttcgcc | 4560 |
| acctctgact tgagcgtcga ctcttgtgat gctcgtcagg ggggcggagc ctatggaaaa | 4620 |
| acgccagcaa cgcggccctt ctacggttcc tggccttctg ctggcctctt gctcacatgt | 4680 |
| tctctcctgc gctatcccct gactctgtgg ataaccgtat taccgccatg cat | |

SEQ ID NO: 11

| | |
|---|---:|
| tctagatggg gcaactggag atgatgggag aagaaagcct aagggactaa gaggaaagcc | 60 |
| acaatctgtc ggtaaatcct gccttgggta gaatcttcta aacctttccc gctttcagca | 120 |
| ctcttatcct gtcccacagg caaggggag ttttaaatc tcctctccat caccatcttg | 180 |
| tgttccgccc tggttcctaa ttgtcttact tgagccattc actccatcca gccgagacct | 240 |
| tgttttagca gacacacaac tgcctagagt ctacacgccc ctcccttccc caaactaaag | 300 |
| tgcttaggga cccagaaaat aggccaggtc ctcgtaacct tatcgaaata gcacagctag | 360 |
| gccttccacc caacaacact cagagactgg gccataggt aggaaacagc atccagagtc | 420 |
| ttgtccgac agagcccaga catcttctgt agttaagagc cctctgggta ttctcacgtc | 480 |
| ctgccccaaa aaaaggaacc aagcttatct gggggcggtg gggagaaggg ggtgtaagcc | 540 |
| aaagctaaag caactaaagc aactgtgttc tgataggaaa gatccctgga ctgagaacaa | 600 |
| gaaagctgtt ccgcaggaaa gaacacactg cgtggagtgt cagggaggag gccagcacct | 660 |

-continued

| Segyebce list Free Text |  |
|---|---|
| ctggaatgcg gcaggaagat gaatgggaaa gatgaggtgg tggtggaggg cagcagccag | 720 |
| ggccttcaaa atcatcctcc agacaatgac aagcccggtc acctgatctg tgaagaggga | 780 |
| tggtctgcaa tctccaggcc ctcgagcctg tgcaaagggc aggctcaggc agctctgctg | 840 |
| ctagactaag gacatcccag gtgggcacgg agagctgcat ttctcgtaaa gcgccctagg | 900 |
| agcttctgtt gttcaccaga accacgagcc cctggactgg accgttcaca aggctcgttc | 960 |
| cagttagaaa attccatcac tctaagagct gggaggcacc taacctccaa gggagggaga | 1020 |
| gggaagtgga tctcccactt gccagcccag ggatgacttc caacagtgcc attacagtaa | 1080 |
| tggaaactgc agtgaaggtg ccagggctga cttctgtgaa gaaagaggag gacaggagtt | 1140 |
| cccctagtgg ctcatcagaa atgaatctga ctagcatcca tgaggatgca ggttcaatcc | 1200 |
| ctggcctcat tcagtggctt aaggatccag cgttgccgag agctgtgatg taggtcacag | 1260 |
| acgcggctca gatcccgtgt tgctgttgct gtggctgtgg cataggtcag aagcgacagc | 1320 |
| tctgatttga cccctaacct gggaacctcc atatcccgct agtgcggccc ttaaaagaca | 1380 |
| aaaagaagga aaagagaaga aaagacatag gcgaacagaa aggcagatga cagggtggca | 1440 |
| gggccagcct acacgatggc ccgaccagaa ttcacaaaga agccacaagg atgcaaatca | 1500 |
| atcaaataaa cctttgttca aaaaaattta tctcacctgt gagtgggaga dacaagtcac | 1560 |
| cccagggctt ctggtgactt caaattgata gggagaaaat ggttgcccca ggggattaaa | 1620 |
| agcttggtat ctgctactcc tttagagttg gcctgtctcc tccactttcc cacaattcca | 1680 |
| ccatttcccc ctcccactgg gctgggatgc agctgtggag tggctcagct ccaaggacta | 1740 |
| ggggctccac agcccaggtc cggcggccag ccctcccact tccagcctgg aagtgggatg | 1800 |
| gggagtggga tgagatgaac ccggcagatt gtagccacag atgtggatgt gcagggtcca | 1860 |
| gcacagggct tgggtgagga gggcggcacc ccatcccttg tctgaagacc aagcagacag | 1920 |
| tactcaggac ttgggagggg gttggggag gaggagtgca tgaaactgag aagaaccttc | 1980 |
| tagccgcctg cgccaggagg tacccgggag ctgaaggaga tggagtgccc cagagcagaa | 2040 |
| agccctgca ggtctggatg ttctaggctg gatgaggggg cgaggcaggc ctggggacct | 2100 |
| gggaagacca ggcgcagtac ctgccttgct tctgaaaatg ctgctccaac gtggaaaaac | 2160 |
| actcccacca tctttctttg gagaaagcct gtaatattcc aacaccaaaa cctctcacta | 2220 |
| gaggttcccg tggagatggg ttccagatga aaagggaagg aggaggcatg ggcgctgcct | 2280 |
| aacctccatc ctccattcct taccctctc ccaccggctt ctgaagccgg ggtcagaaga | 2340 |
| aagggttaaa gccttaaaag gggaccgatt ttgcggggcc ctgggggtcg gctggcacac | 2400 |
| cctgagcggc cccgcccttc tctctagtgt ccagaaccct ccctgccctg cccaggccta | 2460 |
| acggccacag gggagggcc cccctttact gcagaccgcc actctcccac accaatatcg | 2520 |
| gaccgcctcc tcctccctct gccacccctt ctcgctcccc actcagcctc tgattggcc |  |

SEQ ID NO: 12

| tttgaaagac cccacccgta ggtggcaagc tagcttaagt aacgccactt tgcaaggcat | 60 |
|---|---|
| ggaaaaatac ataactgaga atagaaaagt tcagatcaag gtcaggaaca aagaaacagc | 120 |
| tgaataccaa acaggatatc tgtggtaagc ggttcctgcc ccggctcagg gccaagaaca | 180 |
| gatgagacag ctgagtgatg ggccaaacag gatatctgtg gtaagcagtt cctgccccgg | 240 |
| ctcggggcca agaacagatg gtccccagat gcggtccagc cctcagcagt ttctagtgaa | 300 |
| tcatcagatg tttccagggt gccccaagga cctgaaaatg accccgtacc ttatttgaac | 360 |

| Segyebce list Free Text | |
|---|---|
| taaccaatca gttcgcttct cgcttctgtt cgcgcgcttc cgctctccga gctcaataaa | 420 |
| agagcccaca acccctcact cggcgcgcca gtcttccgat agactgcgtc gcccgggtac | 480 |
| ccgtattccc aataaagcct cttgctgttt gcatccgaat cgtggtctcg ctgttccttg | 540 |
| ggagggtctc ctctgagtga ttgactaccc acgacggggg tctttcattt ggggctcgt | 600 |
| ccgggatttg gagacccctg cccagggacc accgacccac caccgggagg taagctggcc | 660 |
| agcaacttat ctgtgtctgt ccgattgtct agtgtctatg tttgatgtta tgcgcctgcg | 720 |
| tctgtactag ttagctaact agctctgtat ctggcggacc cgtggtggaa ctgacgagtt | 780 |
| ctgaacaccc ggccgcaacc ctgggagacg tcccagggac tttggggcc gttttgtgg | 840 |
| cccgacctga ggaagggagt cgatgtggaa tccaccccg tcaggatatg tggttctggt | 900 |
| aggagacgag aacctaaaac agttcccgcc tccgtctgaa ttttgcttt cggtttggaa | 960 |
| ccgaagccgc gcgtcttgtc tgctgcagcg ctgcagcatc gttctgtgtt gtctctgtct | 1020 |
| gactgtgttt ctgtatttgt ctgaaaatta gggccagact gttaccactc ccttaagttt | 1080 |
| gaccttaggt cactggaaag atgtcgagcg gatcgctcac aaccagtcgg tagatgtcaa | 1140 |
| gaagagacgt tgggttacct tctgctctgc agaatggcca acctttaacg tcggatggcc | 1200 |
| gcgagacggc acctttaacc gagacctcat cacccaggtt aagatcaagg tcttttcacc | 1260 |
| tggcccgcat ggacacccag accaggtccc ctacatcgtg acctgggaag ccttggcttt | 1320 |
| tgaccccct ccctgggtca agccctttgt acaccctaag cctccgcctc ctcttcctcc | 1380 |
| atccgccccg tctctcccccc ttgaacctcc tcgttcgacc ccgcctcgat cctcccttta | 1440 |
| tccagccctc actccttctc taggcgccgg aattccgatc tgatagcttg ccacaacccg | 1500 |
| taccaaagat ggatagatcc ggaaagcctg aactcaccgc gacgtctgtc gagaagtttc | 1560 |
| tgatcgaaaa gttcgacagc gtctccgacc tgatgcagct ctcggagggc gaagaatctc | 1620 |
| gtgctttcag cttcgatgta ggagggcgtg gatatgtcct gcgggtaaat agctgcgccg | 1680 |
| atggtttcta caaagatcgt tatgtttatc ggcactttgc atcggccgcg ctcccgattc | 1740 |
| cggaagtgct tgacattggg gaattcagcg agagcctgac ctattgcatc tcccgccgtg | 1800 |
| cacagggtgt cacgttgcaa gacctgcctg aaaccgaact gcccgctgtt ctgcagccgg | 1860 |
| tcgcggaggc catggatgcg atcgctgcgg ccgatcttag ccagacgagc gggttcggcc | 1920 |
| cattcggacc gcaaggaatc ggtcaataca ctacatggcg tgatttcata tgcgcgattg | 1980 |
| ctgatcccca tgtgtatcac tggcaaactg tgatggacga caccgtcagt gcgtccgtcg | 2040 |
| cgcaggctct cgatgagctg atgctttggg ccgaggactg ccccgaagtc cggcacctcg | 2100 |
| tgcacgcgga tttcggctcc aacaatgtcc tgacggacaa tggccgcata acagcggtca | 2160 |
| ttgactggag cgaggcgatg ttcggggatt cccaatacga ggtcgccaac atcttcttct | 2220 |
| ggaggccgtg gttggcttgt atggagcagc agacgcgcta cttcgagcgg aggcatccgg | 2280 |
| agcttgcagg atcgccgcgg ctccgggcgt atatgctccg cattggtctt gaccaactct | 2340 |
| atcagagctt ggttgacggc aatttcgatg atgcagcttg ggcgcagggt cgatgcgacg | 2400 |
| caatcgtccg atccggagcc gggactgtcg ggcgtacaca aatcgcccgc agaagcgcgg | 2460 |
| ccgtctggac cgatggctgt gtagaagtac tcgccgatag tggaaaccga cgccccagca | 2520 |
| ctcgtccgag ggcaaaggaa tagagtagat gccgaccgaa caagagctga tttcgagaac | 2580 |
| gcctcagcca gcaactcgcg cgagcctagc aaggcaaatg cgagagaacg gccttacgct | 2640 |
| tggtggcaca gttctcgtcc acagttcgct aagctcgctc ggctgggtcg cgggagggcc | 2700 |

| | | | | | |
|---|---|---|---|---|---|
| ggtcgcagtg | attcaggccc | ttctggattg | tgttggtccc | cagggcacga | ttgtcatgcc | 2760
| cacgcactcg | ggtgatctga | ctgatcccgc | agattggaga | tcgccgcccg | tgcctgccga | 2820
| ttgggtgcag | atctatttaa | atatcaaata | aacctttgtt | caaaaaaatt | tatctcacct | 2880
| gtgagtggga | gagacaagtc | accccagggc | ttctggtgac | ttcaaattga | tagggagaaa | 2940
| atggttgccc | cagggratta | aaagcttggt | atctgctact | cctttagagt | tggcctgtct | 3000
| cctccacttt | cccacaattc | caccatttcc | ccctcccact | gggctgggat | gcagctgtgg | 3060
| agtggctcag | ctccaaggac | tagggctcc | acagcccagg | tccggcggcc | agccctccca | 3120
| cttccagcct | ggaagtggga | tggggagtgg | gatgagatga | acccggcaga | ttgtagccac | 3180
| agatgtggat | gcgcagggtc | cagcacaggg | cttgggtgag | gagggcggca | ccccatccct | 3240
| tgtctgaaga | ccaagcagac | agtactcagg | acttgggagg | gggctggggg | aggaggagtg | 3300
| catgaaactg | agaagaacct | tctagctgcc | tgcgccagga | ggtacccggg | agctgaagga | 3360
| gatggagtgc | cccagagcag | aaagcccctg | caggtctgga | tgttctaggc | tggatgaggg | 3420
| ggcgaggcag | gcctggggac | ctgggaagac | caggcgcagt | acctgccttg | cttctgaaaa | 3480
| tgctgctcca | acgtggaaaa | acactcccac | catctttctt | tggagaaagc | ctgtaatatt | 3540
| ccaacaccaa | aacctctcac | tagaggttcc | cgtggagatg | ggttccagat | gaaaagggaa | 3600
| ggaggaggca | tgggcgctgc | ctaacctcca | tcctccattc | cttacccctc | tcccaccggc | 3660
| ttctgaagcc | ggggtcagaa | gaaagggtta | aagccttaaa | aggggaccga | ttttgcgggg | 3720
| ctctgggggt | cggctggcac | accctgagcg | gccccgccct | tctctctagt | gtccagaacc | 3780
| ctccctgccc | tgcccaggcc | taacggccac | aggggagg | cccccttta | ctgcagaccg | 3840
| ccactctccc | acaccaatat | cggaccgcct | cctcctccct | ctgccacccc | ttctcgctcc | 3900
| ccactcagcc | tctgattggc | catcgatatg | ctgcccggtt | tggcactgct | cctgctggcc | 3960
| gcctggacgg | ctcgggcgct | ggaggtaccc | actgatggta | atgctggcct | gctggctgaa | 4020
| ccccagattg | ccatgttctg | tggcagactg | aacatgcaca | tgaatgtcca | gaatgggaag | 4080
| tgggattcag | atccatcagg | gaccaaaacc | tgcattgata | ccaaggaagg | catcctgcag | 4140
| tattgccaag | aagtctaccc | tgaactgcag | atcaccaatg | cggtagaagc | caaccaacca | 4200
| gtgaccatcc | agaactggtg | caagcggggc | cgcaagcagt | gcaagaccca | tccccacttt | 4260
| gtgattccct | accgctgctt | agttggtgag | tttgtaagtg | atgcccttct | cgttcctgac | 4320
| aagtgcaaat | tcttacacca | ggagaggatg | gatgtttgcg | aaactcatct | tcactggcac | 4380
| accgtcgcca | aagagacatg | cagtgagaag | agtaccaact | tgcatgacta | cggcatgttg | 4440
| ctgccctgcg | gaattgacaa | gttccgaggg | gtagagtttg | tgtgttgccc | actggctgaa | 4500
| gaaagtgaca | atgtggattc | tgctgatgcg | gaggaggatg | actcggatgt | ctggtgggc | 4560
| ggagcagaca | cagactatgc | agatgggagt | gaagacaaag | tagtagaagt | agcagaggag | 4620
| gaagaagtgg | ctgaggtgga | agaagaagaa | gccgatgatg | acgaggacga | tgaggatggt | 4680
| gatgaggtag | aggaagaggc | tgaggaaccc | tacgaagaag | ccacagagag | aaccaccagc | 4740
| attgccacca | ccaccaccac | caccacagag | tccgtggaag | aggtggttcg | agttcctaca | 4800
| acagcagcca | gtaccctga | tgccgttgac | aagtatctcg | agacacctgg | ggatgagaat | 4860
| gaacatgccc | atttccagaa | agccaaagag | aggcttgagg | ccaagcaccg | agagagaatg | 4920
| tcccaggtca | tgagagaatg | ggaagaggca | gaacgtcaag | caaagaactt | gcctaaagct | 4980

-continued

| Segyebce list Free Text | |
|---|---|
| gataagaagg cagttatcca gcatttccag gagaaagtgg aatctttgga acaggaagca | 5040 |
| gccaacgaga gacagcagct ggtggagaca cacatggcca gagtggaagc catgctcaat | 5100 |
| gaccgccgcc gcctggccct ggagaactac atcaccgctc tgcaggctgt tcctcctcgg | 5160 |
| cctcgtcacg tgstcaatat gctaaagaag tatgtccgcg cagaacagaa ggacagacag | 5220 |
| cacaccctaa agcatttcga gcatgtgcgc atggtggatc ccaagaaagc cgctcagatc | 5280 |
| cggtcccagg ttatgacaca cctccgtgtg atttatgagc gcatgaatca gtctctctcc | 5340 |
| ctgctctaca acgtgcctgc agtggccgag gagattcagg atgaagttga tgagctgctt | 5400 |
| cagaaagagc aaaactattc agatgacgtc ttggccaaca tgattagtga accaaggatc | 5460 |
| agctacggaa acgatgctct catgccatct ttgaccgaaa cgaaaaccac cgtggagctc | 5520 |
| cttcccgtga atggagagtt cagcctggac gatctccagc cgtggcattc ttttggggct | 5580 |
| gactctgtgc cagccaacac agaaaacgaa gttgagcctg ttgatgcccg ccctgctgcc | 5640 |
| gaccgaggac tgaccactcg accaggttct gggttgacaa atatcaagac ggaggagatc | 5700 |
| tctgaagtga atctggatgc agaattccga catgactcag gatatgaagt tcatcatcaa | 5760 |
| aaattggtgt tctttgcaga agatgtgggt tcaaacaaag gtgcaatcat tggactcatg | 5820 |
| gtgggcggtg ttgtcatagc gacugtggtc atcatcacct tggtgatgct gaagaagaaa | 5880 |
| cagtacacat ccattcatca tggtgtggtg gaggttgacg ccgctgtcac cccagaggag | 5940 |
| cgccacctgt ccaatctgca gcagaacggc tacgaaaatc caacctacaa gttctttgag | 6000 |
| cagatgcaga acttaactaa ggcatgcgga agcggagcta ctaacttcag cctgctgaag | 6060 |
| caggctggag acgtggagga gaaccctgga cctagatcta tggctgagcc ccgccaggag | 6120 |
| ttcgaagtga tggaagatca cgctgggacg tacgggttgg gggacaggaa agatcagggg | 6180 |
| ggctacacca tgcaccaaga ccaagagggt gacacggacg ctggcctgaa agctgaagaa | 6240 |
| gcaggcattg gagacacccc cagcctggaa gacgaagctg ctggtcacgt gacccaagct | 6300 |
| cgcatggtca gtaaaagcaa agacgggact ggaagcgatg acaaaaaagc caggggggct | 6360 |
| gatggtaaaa tgaagatcgc cacaccgcgg ggagcagccc ctccaggcca gaagggccag | 6420 |
| gccaacgcca ccaggattcc agcaaaaacc ccgcccgctc caaagacacc acccagctct | 6480 |
| ggtgaacctc caaatcagg ggatcgcagc ggctacagca gccccggctc cccaggcact | 6540 |
| cccggcagcc gctcccgcac cccgtcccectt ccaaccccac ccacccggga gcccaagaag | 6600 |
| gtggcagtgg tccgtactcc acccaagtcg ccgtcttccg ccaagagccg cctgcagaca | 6660 |
| gcccccgtgc ccatgccaga cctgaagaat gtcaagtcca agatcggctc cactgagaac | 6720 |
| ctgaagcacc agccgggagg cgggaaggtg cagataatta ataagaagct ggatcttagc | 6780 |
| aacgtccagt ccaagtgtgg ctcaaaggat aaatatcaaac acgtcctggg aggcggcagt | 6840 |
| gtgcaaatag tctacaaacc agttgacctg agcaaggtga cctccaagtg tggctcatta | 6900 |
| ggcaacatcc atcataaacc aggaggtggc caggtggaag taaaatctga gaagcttgac | 6960 |
| ttcaaggaca gagtccagtc gaagattggg tccctggaca atatcaccca cgtccctggc | 7020 |
| ggaggaaata aaaagattga aacccacaag ctgaccttcc gcgagaacgc caaagccaag | 7080 |
| acagaccacg gggcggagat cgtgtacaag tcgccagtgg tgtctgggga cacgtctcca | 7140 |
| cggcatctca gcaatgtctc ctccaccggc agcatcgaca tggtagaccc gccccagctc | 7200 |
| gccacgctag ctgacgaggt gtctgcctcc ctggccaagc agggtttgga attcggaagc | 7260 |
| ggagctacta acttcagcct gctgaagcag gctggagacg tggaggagaa ccctggacct | 7320 |

| Segyebce list Free Text | |
|---|---|
| ctcgagatga cagagttacc tgcaccgttg tcctacttcc agaatgcaca gatgtctgag | 7380 |
| gacaaccacc tgagcaatac tgtacgtagc cagaatgaca atagagaacg gcaggagcac | 7440 |
| aacgacagac ggagccttgg ccaccctgag ccattatcta atggacgacc ccagggtaac | 7500 |
| tcccggcagg tggtggagca agatgaggaa gaagatgagg agctgacatt gaaatatggc | 7560 |
| gccaagcatg tgatcatgct ctttgtccct gtgactctct gcatggtggt ggtcgtggct | 7620 |
| accattaagt cagtcagctt ttatacccgg aaggatgggc agctaatcta taccccattc | 7680 |
| acagaagata ccgagactgt gggccagaga gccctgcact caattctgaa tgctgccatc | 7740 |
| atgatcagtg tcattgttgt cctgactatc ctcctggtgg ttctgtataa atacaggtgc | 7800 |
| tataaggtca tccatgcctg gcttattata tcatctctat tgttgctgtt cttttttttca | 7860 |
| ttcatttact tgggggaagt gtttaaaacc tataacgttg ctgtggacta cattactgtt | 7920 |
| gcactcctga tctggaattt tggtgtggtg ggaatgattt ccattcactg gaaaggtcca | 7980 |
| cttcgactcc agcaggcata tctcattatg attagtgccc tcatggccct ggtgtttatc | 8040 |
| aagtacctcc ctgaatggac tgcgtggctc atcttggctg tgatttcagt atatgattta | 8100 |
| gtggctgttt tgtgtccgaa aggtccactt cgtatgctgg ttgaaacagc tcaggagaga | 8160 |
| aatgaaacgc ttttttccagc tgtcatttac tcctcaacaa tggtgtggtt ggtgaatatg | 8220 |
| gcagaaggag acccggaagc tcaaaggaga gtatccaaaa attccaagta taatgcagaa | 8280 |
| agcacagaaa gggagtcaca agacactgtt gcagagaatg atgatggcgg gttcagtgag | 8340 |
| gaatgggaag cccagaggga cagtcatcta gggcctcatc gctctacacc tgagtcacga | 8400 |
| gctgctgtcc aggaactttc cagcagtatc ctcgctggtg aagacccaga ggaaagggga | 8460 |
| gtaaaacttg gattgggaga tttcatttttc tacagtgttc tggttggtaa agcctcagca | 8520 |
| acagccagtg gagactggaa cacaaccata gcctgtttcg tagccatatt aattggtttg | 8580 |
| tgccttacat tattactcct tgccattttc aagaaagcat tgccagctct tccaatctcc | 8640 |
| atcacctttg ggcttgtttt ctactttgcc acagattatc ttgtacagcc ttttatggac | 8700 |
| caattagcat tccatcaast ttatatctag cctgcaggtc tagataccta gcctccctat | 8760 |
| agtgagtcgt attacgtaga tccagacatg ataagataca ttgatgagtt tggacaaacc | 8820 |
| acaactagaa tgcagtgaaa aaaatgcttt atttgtgaaa tttgtgatgc tattgcttta | 8880 |
| tttgtaacca ctataagctg caataaacaa gttaacaaca acaattgcat tcattttatg | 8940 |
| tttcaggttc agggggaggt gtgggaggtt ttttaattcg cggccgcctc gagagatccc | 9000 |
| ctcaggatat agtagtttcg cttttgcata gggaggggga aatgtagtct tatgcaatac | 9060 |
| tcttgtagtc ttgcaacacg gtaacgatga gttagcaaca tgccttacaa ggagagaaaa | 9120 |
| agcaccgtgc atgccgattg gtggaagtaa ggtggtacga tcgtgcctta ttaggaaggc | 9180 |
| aacagacggg tctgacatgg attggacgaa ccactgaatt ccgcattgca gagatattgt | 9240 |
| atttaagtgc ctagctcgat acagcaaacg ccatttgacc attcaccaca ttggtgtgca | 9300 |
| cctccaagct tgttaattca ccatgtctag actggacaag agcaaagtca taaacgcgc | 9360 |
| tctggaatta ctcaatggag tcggtatcga aggcctgacg acaaggaaac tcgctcaaaa | 9420 |
| gctgggagtt gagcagccta ccctgtactg gcacgtgaag aacaagcggg ccctgctcga | 9480 |
| tgccctgcca atcgagatgc tggacaggca tcatacccac ttctgccccc tggaaggcga | 9540 |
| gtcatggcaa gactttctgc ggaacaacgc caagtcattc cgctgtgctc tcctctcaca | 9600 |

-continued

| Sequence list Free Text | |
|---|---|
| tcgcgacggg gctaaagtgc atctcggcac ccgcccaaca gagaaacagt acgaaaccct | 9660 |
| ggaaaatcag ctcgcgttcc tgtgtcagca aggcttctcc ctggagaacg cactgtacgc | 9720 |
| tctgtccgcc gtgggccact ttacactggg ctgcgtattg gaggaacagg agcatcaagt | 9780 |
| agcaaaagag gaaagagaga cacctaccac cgattctatg cccccacttc tgagacaagc | 9840 |
| aattgagctg ttcgaccggc agggagccga acctgccttc cttttcggcc tggaactaat | 9900 |
| catatgtggc ctggagaaac agctaaagtg cgaaagcggc gggccggccg acgcccttga | 9960 |
| cgattttgac ttagacatgc tcccagccga tgcccttgac gactttgacc ttgatatgct | 10020 |
| gcctgctgac gctcttgacg attttgacct tgacatgctc cccgggtaac taagtaagga | 10080 |
| tcaacatcga attcgatttc tgttcctgtt aatcaacctc tggattacaa aatttgtgaa | 10140 |
| agattgactg gtattcttaa ctatgttgct ccttttacgc tatgtggata cgctgcttta | 10200 |
| atgcctttgt atcatgctat tgcttcccgt atggctttca ttttctcctc cttgtataaa | 10260 |
| tcctggttgc tgtctcttta tgaggagttg tggcccgttg tcaggcaacg tggcgtggtg | 10320 |
| tgcactgtgt ttgctgacgc aacccccact ggttggggca ttgccaccac ctgtcagctc | 10380 |
| cttccggga ctttcgcttt ccccctccct attgccacgg cggaactcat cgccgcctgc | 10440 |
| cttgcccgct gctggacagg ggctcggctg ttgggcactg acaattccgt ggtgttgtcg | 10500 |
| gggaagctga cgtcctttcc atggctgctc gcctgtgttg ccacctggat tctgcgcggg | 10560 |
| acgtccttct gctacgtccc ttcggccctc aatccagcgg accttccttc ccgcggcctg | 10620 |
| ctgccggctc tgcggcctct tccgcgtctt cgccttcgcc ctcagacgag tcggatctcc | 10680 |
| ctttgggccg cctccccgcc tgtttcgcct cgggctcaat cactagtgaa ttcgataaaa | 10740 |
| taaaagattt tatttagtct ccagaaaaag gggggaatga agacccac ctgtaggttt | 10800 |
| ggcaagctag cttaagtaac gccattttgc aaggcatgga aaatacata actgagaata | 10860 |
| gagaagttca gatcaaggtc aggaacagat ggaacagctg aatatgggcc aaacaggata | 10920 |
| tctgtggtaa gcagttcctg ccccggctca gggccaagaa cagatggaac agctgaatat | 10980 |
| gggccaaaca ggatatctgt ggtaagcagt tcctgccccg gctcagggcc aagaacagat | 11040 |
| ggtccccaga tgcggtccag ccctcagcag tttctagaga accatcagat gtttccaggg | 11100 |
| tgccccaagg acctgaaatg accctgtgcc ttatttgaac taaccaatca gttcgcttct | 11160 |
| cgcttctgtt cgcgcgcctc tgctccccga gctcaataaa agagcccaca cccctcact | 11220 |
| cggggcgcca gtcctccgat tgactgagtc gcccgggtac ccgtgtatcc aataaaccct | 11280 |
| cttgcagttg catccgactt gtggtctcgc tgttccttgg gagggtctcc tctgagtgat | 11340 |
| tgactacccg tcagcggggg tctttcattt ggggggctcgt ccgggatcgg agacccctg | 11400 |
| cccagggacc accgacccac caccgggagg taagctggct gcctcgcgcg tttcggtgat | 11460 |
| gacggtgaaa acctctgaca catgcagctc ccggagacgg tcacagcttg tctgtaagcg | 11520 |
| gatgccggga gcagacaagc ccgtcagggc gcgtcagcgg gtgttggcgg gtgtcgggc | 11580 |
| gcagccatga cccagtcacg tagcgatagc ggagtgtata ctggcttaac tatgcggcat | 11640 |
| cagagcagat tgtactgaga gtgcaccata tgcggtgtga ataccgcac agatgcgtaa | 11700 |
| ggagaaaata ccgcatcagg cgctcttccg cttcctcgct cactgactcg ctgcgctcgg | 11760 |
| tcgttcggct gcggcgagcg gtatcagctc actcaaaggc ggtaatacgg ttatccacag | 11820 |
| aatcagggga taacgcagga aagaacatgt gagcaaaagg ccagcaaaag ccaggaacc | 11880 |
| gtaaaaaggc cgcgttgctg gcgtttttcc ataggctccg ccccctgac gagcatcaca | 11940 |

-continued

| Sequence list Free Text |
|---|
| aaaatcgacg ctcaagtcag aggtggcgaa acccgacagg actataaaga taccaggcgt 12000 |
| ttccccctgg aagcscccctc gtgcgctctc ctgttccgac cctgccgctt accggatacc 12060 |
| tgtccgcctt tctcccttcg ggaagcgtgg cgctttctca tagctcacgc tgtaggtatc 12120 |
| tcagttcggt gtaggtcgtt cgctccaagc tgggctgtgt gcacgaaccc cccgttcagc 12180 |
| ccgaccgctg cgccttatcc ggtaactatc gtcttgagtc caacccggta agacacgact 12240 |
| tatcgccact ggcagcagcc actggtaaca ggattagcag agcgaggtat gtaggcggtg 12300 |
| ctacagagtt cttgaagtgg tggcctaact acggctacac tagaaggaca gtatttggta 12360 |
| tctgcgctct gctgaagcca gttaccttcg gaaaaagagt tggtagctct tgatccggca 12420 |
| aacaaaccac cgctggtagc ggtggttttt tgtttgcaa gcagcagatt acgcgcagaa 12480 |
| aaaaggatc tcaagaagat cctttgatct tttctacggg gtctgacgct cagtggaacg 12540 |
| aaaactcacg ttaagggatt tggtcatga gattatcaaa aaggatcttc acctagatcc 12600 |
| ttttaaatta aaaatgaagt tttaaatcaa tctaaagtat atatgagtaa acttggtctg 12660 |
| acagttacca atgcttaatc agtgaggcac ctatctcagc gatctgtcta tttcgttcat 12720 |
| ccatagttgc ctgactcccc gtcgtgtaga taactacgat acgggagggc ttaccatctg 12780 |
| gccccagtgc tgcaatgata ccgcgagacc cacgctcacc ggctccagat ttatcagcaa 12840 |
| taaaccagcc agccggaagg gccgagcgca gaagtggtcc tgcaactta tccgcctcca 12900 |
| tccagtctat taattgttgc cgggaagcca gagtaagtag ttcgccagtt aatagtttgc 12960 |
| gcaacgttgt tgccattgct gcaggcatcg tggtgtcacg ctcgtcgttc ggtatggctt 13020 |
| cattcagctc cggttcccaa cgatcaaggc gagttacatg atcccccatg ttgtgcaaaa 13080 |
| aagcggttag ctccttcggt cctccgatcg ttgtcagaag taagttggcc gcagtgttat 13140 |
| cactcatggt tatggcagca ctgcataatt ctcttactgt catgccatcc gtaagatgct 13200 |
| tttctgtgac tggtgagtac tcaaccaagt cattctgaga atagtgtatg cggcgaccga 13260 |
| gttgctcttg cccggcgtca acacgggata ataccgcgcc acatagcaga actttaaaag 13320 |
| tgctcatcat tggaaaacgt tcttcgggc gaaaactctc aaggatctta ccgctgttga 13380 |
| gatccagttc gatgtaaccc actcgtgcac ccaactgatc ttcagcatct tttactttca 13440 |
| ccagcgtttc tgggtgagca aaaacaggaa ggcaaaatgc cgcaaaaaag gaataagggg 13500 |
| cgacacggaa atgttgaata ctcatactct tcctttttca atattattga agcatttatc 13560 |
| agggttattg tctcatgagc ggatacatat ttgaatgtat ttagaaaaat aaacaaatag 13620 |
| gggttccgcg cacatttccc cgaaaagtgc cacctgacgt ctaagaaacc attattatca 13680 |
| tgacattaac ctataaaaat aggcgtatca cgaggccctt tcgtcttcaa gaattcatac 13740 |
| cagatcaccg aaaactgtcc tccaaatgtg tccccctcac actcccaaat tcgcgggctt 13800 |
| ctgcctctta gaccactcta ccctattccc cacactcacc ggagccaaag ccgcggccct 13860 |
| tccgtttctt tgct |

What is claimed is:

1. A recombinant expression vector, comprising:
a Thy1 gene promoter having a base sequence of SEQ ID NO: 1 or SEQ ID NO: 4; and
a mutant gene selected from the group consisting of a mutant APP gene, a mutant Tau gene and a mutant PS1 gene, wherein said mutant APP gene, said mutant Tau gene and said mutant PS1 gene are found in patients with familial Alzheimer's disease.

2. A non-human mammalian embryo comprising the recombinant expression vector of claim 1.

* * * * *

SEQUENCE LISTING

<160> NUMBER OF SEQ ID NOS: 20

<210> SEQ ID NO 1
<211> LENGTH: 500

```
<212> TYPE: DNA
<213> ORGANISM: Porcine
<220> FEATURE:
<221> NAME/KEY: promoter
<222> LOCATION: (1)..(500)
<223> OTHER INFORMATION: Thy-1 promoter (-3380/-2880) sequences

<400> SEQUENCE: 1
gaagccacaa ggatgcaaat caatcaaata aacctttgtt caaaaaaatt tatctcacct      60
gtgagtggga gagacaagtc accccagggc ttctggtgac ttcaaattga tagggagaaa     120
atggttgccc caggggatta aaagcttggt atctgctact cctttagagt tggcctgtct     180
cctccacttt cccacaattc caccatttcc ccctcccact gggctgggat gcagctgtgg     240
agtggctcag ctccaaggac taggggctcc acagcccagg tccggcggcc agccctccca     300
cttccagcct ggaagtggga tggggagtgg gatgagatga acccggcaga ttgtagccac     360
agatgtggat gtgcagggtc cagcacaggg cttgggtgag gagggcggca ccccatccct     420
tgtctgaaga ccaagcagac agtactcagg acttgggagg gggttggggg aggaggagtg     480
catgaaactg agaagaacct                                                 500

<210> SEQ ID NO 2
<211> LENGTH: 20
<212> TYPE: DNA
<213> ORGANISM: Artificial Sequence
<220> FEATURE:
<223> OTHER INFORMATION: forward primer for amplifying Thy-1 promoter
      (500bp)

<400> SEQUENCE: 2
gaagccacaa ggatgcaaat                                                  20

<210> SEQ ID NO 3
<211> LENGTH: 20
<212> TYPE: DNA
<213> ORGANISM: Artificial Sequence
<220> FEATURE:
<223> OTHER INFORMATION: reverse primer for amplifying Thy-1 promoter
      (500bp)

<400> SEQUENCE: 3
aggttcttct cagtttcatg                                                  20

<210> SEQ ID NO 4
<211> LENGTH: 2579
<212> TYPE: DNA
<213> ORGANISM: Porcine
<220> FEATURE:
<221> NAME/KEY: promoter
<222> LOCATION: (1)..(2579)
<223> OTHER INFORMATION: Thy-1 promoter (-4858/-2279) sequences

<400> SEQUENCE: 4
tctagatggg gcaactggag atgatgggag aagaaagcct aagggactaa gaggaaagcc      60
acaatctgtc ggtaaatcct gccttgggta gaatcttcta aacctttccc gctttcagca     120
ctcttatcct gtcccacagg caaaggggag tttttaaatc tcctctccat caccatcttg     180
tgttccgccc tggttcctaa ttgtcttact tgagccattc actccatcca gccgagacct     240
tgttttagca gacacacaac tgcctagagt ctacacgccc ctcccttttcc caaactaaag    300 tgcttaggga cccagaaaat aggccaggtc ctcgtaacct tatcgaaata gcacagctag     360
gccttccacc caacaacact cagagactgg gccatagggt aggaaacagc atccagagtc     420
```

-continued

```
ttgtccagac agagcccaga catcttctgt agttaagagc cctctgggta ttctcacgtc      480
ctgccccaaa aaaaggaacc aagcttatct gggggcggtg gggagaaggg ggtgtaagcc      540
aaagctaaag caactaaagc aactgtgttc tgataggaaa gatccctgga ctgagaacaa      600
gaaagctgtt ccgcaggaaa gaacacactg cgtggagtgt cagggaggag gccagcacct      660
ctggaatgcg gcaggaagat gaatgggaaa gatgaggtgg tggtggaggg cagcagccag      720
ggccttcaaa atcatcctcc agacaatgac aagcccggtc acctgatctg tgaagaggga      780
tggtctgcaa tctccaggcc ctcgagcctg tgcaaagggc aggctcaggc agctctgctg      840
ctagactaag gacatcccag gtgggcacgg agagctgcat ttctcgtaaa gcgccctagg      900
agcttctgtt gttcaccaga accacgagcc cctggactgg accgttcaca aggctcgttc      960
cagttagaaa attccatcac tctaagagct gggaggcacc taacctccaa gggagggaga     1020
gggaagtgga tctcccactt gccagcccag ggatgacttc caacagtgcc attacagtaa     1080
tggaaactgc agtgaaggtg ccagggctga cttctgtgaa gaaagaggag gacaggagtt     1140
cccctagtgg ctcatcagaa atgaatctga ctagcatcca tgaggatgca ggttcaatcc     1200
ctggcctcat tcagtggctt aaggatccag cgttgccgag agctgtgatg taggtcacag     1260
acgcggctca gatcccgtgt tgctgttgct gtggctgtgg cataggtcag aagcgacagc     1320
tctgatttga cccctaacct gggaacctcc atatcccgct agtgcggccc ttaaaagaca     1380 aaagaagga aaagagaaga aaagacatag gcgaacagaa aggcagatga cagggtggca     1440
gggccagcct acacgatggc ccgaccagaa ttcacaaaga agccacaagg atgcaaatca     1500
atcaaataaa cctttgttca aaaaaattta tctcacctgt gagtgggaga acaagtcac     1560 cccagggctt ctggtgactt caaattgata gggagaaaat ggttgcccca ggggattaaa     1620
agcttggtat ctgctactcc tttagagttg gcctgtctcc tccactttcc cacaattcca     1680
ccatttcccc ctcccactgg gctgggatgc agctgtggag tggctcagct ccaaggacta     1740
ggggctccac agcccaggtc cggcggccag ccctcccact tccagcctgg aagtgggatg     1800
gggagtggga tgagatgaac ccggcagatt gtagccacag atgtggatgt gcagggtcca     1860
gcacagggct tgggtgagga gggcggcacc ccatcccttg tctgaagacc aagcagacag     1920
tactcaggac ttgggagggg gttggggag gaggagtgca tgaaactgag aagaaccttc     1980
tagctgcctg cgccaggagg tacccgggag ctgaaggaga tggagtgccc cagagcagaa     2040
agcccctgca ggtctggatg ttctaggctg gatgaggggg cgaggcaggc ctggggacct     2100
gggaagacca ggcgcagtac ctgccttgct tctgaaaatg ctgctccaac gtggaaaaac     2160
actcccacca tctttctttg gagaaagcct gtaatattcc aacaccaaaa cctctcacta     2220
gaggttcccg tggagatggg ttccagatga aaagggaagg aggaggcatg ggcgctgcct     2280
aacctccatc ctccattcct tacccctctc ccaccggctt ctgaagccgg ggtcagaaga     2340
aagggttaaa gccttaaaag gggaccgatt ttgcggggct ctggggggtcg gctgcacac     2400 cctgagcggc cccgcccttc tctctagtgt ccagaaccct ccctgccctg cccaggccta     2460
acggccacag ggggagggcc cccctttact gcagaccgcc actctcccac accaatatcg     2520
gaccgcctcc tcctcccctct gccacccctt ctcgctcccc actcagcctc tgattggcc     2579
```

<210> SEQ ID NO 5
<211> LENGTH: 20
<212> TYPE: DNA
<213> ORGANISM: Artificial Sequence
<220> FEATURE:
<223> OTHER INFORMATION: forward primer for amplifying Thy-1 promoter (2579bp)

<400> SEQUENCE: 5
tctagatggg gcaactggag                                              20

<210> SEQ ID NO 6
<211> LENGTH: 20
<212> TYPE: DNA
<213> ORGANISM: Artificial Sequence
<220> FEATURE:
<223> OTHER INFORMATION: reverse primer for amplifying Thy-1 promoter
      (2579bp)

<400> SEQUENCE: 6
ggccaatcag aggctgagtg                                              20

<210> SEQ ID NO 7
<211> LENGTH: 2579
<212> TYPE: DNA
<213> ORGANISM: Porcine
<220> FEATURE:
<221> NAME/KEY: promoter
<222> LOCATION: (1)..(2579)
<223> OTHER INFORMATION: Thy-1 promoter (-4858/-2279) sequences (2579
      bp)

<400> SEQUENCE: 7
tctagatggg gcaactggag atgatgggag aagaaagcct aagggactaa gaggaaagcc    60
acaatctgtc ggtaaatcct gccttgggta gaatcttcta aacctttccc gctttcagca   120
ctcttatcct gtcccacagg caaagggag ttttttaaatc tcctctccat caccatcttg   180
tgttccgccc tggttcctaa ttgtcttact tgagccattc actccatcca gccgagacct   240
tgttttagca gacacacaac tgcctagagt ctacacgccc ctcccttttcc caaactaaag   300 tgcttaggga cccagaaaat aggccaggtc ctcgtaacct tatcgaaata gcacagctag   360
gccttccacc caacaacact cagagactgg gccatagggt aggaaacagc atccagagtc   420
ttgtccagac agagcccaga catcttctgt agttaagagc cctctgggta ttctcacgtc   480
ctgccccaaa aaaggaacc aagcttatct ggggcggtg gggagaaggg ggtgtaagcc     540
aaagctaaag caactaaagc aactgtgttc tgataggaaa gatccctgga ctgagaacaa   600
gaaagctgtt ccgcaggaaa gaacacactg cgtggagtgt cagggaggag gccagcacct   660
ctggaatgcg gcaggaagat gaatgggaaa gatgaggtgg tggtggaggg cagcagccag   720
ggccttcaaa atcatcctcc agacaatgac aagcccggtc acctgatctg tgaagaggga   780
tggtctgcaa tctccaggcc ctcgagcctg tgcaaagggc aggctcaggc agctctgctg   840
ctagactaag gacatcccag gtgggcacgg agagctgcat ttctcgtaaa gcgccctagg   900
agcttctgtt gttcaccaga accacgagcc cctggactgg accgttcaca aggctcgttc   960
cagttagaaa attccatcac tctaagagct gggaggcacc taacctccaa gggagggaga  1020
gggaagtgga tctcccactt gccagcccag ggatgacttc aacagtgcc attacagtaa   1080 tggaaactgc agtgaaggtg ccagggctga cttctgtgaa gaaagaggag gacaggagtt   1140 ccctagtgg ctcatcagaa atgaatctga ctagcatcca tgaggatgca ggttcaatcc   1200
ctggcctcat tcagtggctt aaggatccag cgttgccgag agctgtgatg taggtcacag  1260
acgcggctca gatcccgtgt tgctgttgct gtggctgtgg cataggtcag aagcgacagc  1320
tctgatttga cccctaacct gggaacctcc atatcccgct agtgcggccc ttaaaagaca  1380
aaagaaggga aaagagaaga aaagacatag gcgaacagaa aggcagatga cagggtggca  1440

```
gggccagcct acacgatggc ccgaccagaa ttcacaaaga agccacaagg atgcaaatca    1500
atcaaataaa cctttgttca aaaaaattta tctcacctgt gagtgggaga gacaagtcac    1560
cccagggctt ctggtgactt caaattgata gggagaaaat ggttgcccca ggggattaaa    1620
agcttggtat ctgctactcc tttagagttg gcctgtctcc tccactttcc cacaattcca    1680
ccatttcccc ctcccactgg gctgggatgc agctgtggag tggctcagct ccaaggacta    1740
ggggctccac agcccaggtc cggcggccag ccctcccact tccagcctgg aagtgggatg    1800
gggagtggga tgagatgaac ccggcagatt gtagccacag atgtggatgt gcagggtcca    1860
gcacagggct tgggtgagga gggcggcacc ccatcccttg tctgaagacc aagcagacag    1920
tactcaggac ttgggagggg gttggggag gaggagtgca tgaaactgag aagaaccttc     1980
tagctgcctg cgccaggagg tacccggag ctgaaggaga tggagtgccc cagagcagaa     2040
agcccctgca ggtctggatg ttctaggctg gatgaggggg cgaggcaggc ctggggacct    2100
gggaagacca ggcgcagtac ctgccttgct tctgaaaatg ctgctccaac gtggaaaaac    2160
actcccacca tctttctttg gagaaagcct gtaatattcc aacaccaaaa cctctcacta    2220
gaggttcccg tggagatggg ttccagatga aaagggaagg aggaggcatg ggcgctgcct    2280
aacctccatc ctccattcct taccoctctc ccaccggctt ctgaagccgg ggtcagaaga    2340
aagggttaaa gccttaaaag gggaccgatt ttgcggggct ctggggggtcg gctggcacac   2400 cctgagcggc cccgcccttc tctctagtgt ccagaaccct ccctgccctg cccaggccta    2460
acggccacag ggggagggcc cccctttact gcagaccgcc actctcccac accaatatcg    2520
gaccgcctcc tcctccctct gccacccctt ctcgctcccc actcagcctc tgattggcc     2579

<210> SEQ ID NO 8
<211> LENGTH: 2538
<212> TYPE: DNA
<213> ORGANISM: Porcine
<220> FEATURE:
<221> NAME/KEY: promoter
<222> LOCATION: (1)..(2538)
<223> OTHER INFORMATION: Thy-1 promoter (-2578/-40) sequences (2538 bp)

<400> SEQUENCE: 8
aacctccatc ctccattcct taccoctctc ccaccggctt ctgaagccgg ggtcagaaga      60
aagggttaaa gccttaaaag gggaccgatt ttgcggggct ctggggggtcg gctggcacac    120 cctgagcggc cccgcccttc tctctagtgt ccagaaccct ccctgccctg cccaggccta    180
acggccacag ggggagggcc cccctttact gcagaccgcc actctcccac accaatatcg    240
gaccgcctcc tcctccctct gccacccctt ctcgctcccc actcagcctc tgattggccg    300 agccccccggg tcctccccgc ccctcctctc ccacccttgg tgaaaactgc gggtgccggg    360
cagggtgcag caactggagg cggcggcgtg tccggagcag tctgcggcgg cgagggaccg    420
gaacccaggt gggaactgga gccagggcgg ggcccgagc gccctcggtg cccctgcaag     480
ctctccagac cccaagcttc agaaaaccat ccgagggcgc tcaggaagg agcagtgcag    540 ggcctgggga ggggtctgct tcccaggcag gggcgggagc cggacgccaa ggctgcaggc    600 cggggggccgc aacgcatctt tcgcccgctc ggaggacgtt tgcctgggc gggggcgctg    660 gaggagaact gggaggaagg gcgccaagga cagttttggg ttctgctcgc cacccacaca    720
tccccaagcc ccgcttgcaa agacagggc ggggggcgac gaaactcggg ggagagaacc     780
gaggacccca aactagaggg aatctctgcc ctccgacctc gcgacaggct gggtgcgggg    840
```

-continued

| | |
|---|---|
| catccaagga acgggaaacc gcagtgccgc gggcggggac tgggaggaag gcaggcagac | 900 |
| ggggagggcg agaactggaa aaggatgaga gaggggaag gggacttca attgggaatg | 960 |
| gaggagattg gaatggggag acggaataag ggtggggtta gtcgaacgcg tgctgagagg | 1020 |
| gagggaacgc aaagcttctg cgggttctga gctgcgggga cccaggaaac gaaaacagac | 1080 |
| tgcgcctccc ctaccagctg tctacccctc cctttggctc tccatcccct gccagcccca | 1140 |
| gccccgtttc ttcctttcta ccccttcctc tcctggatcc cgagctcaca ctcctcctct | 1200 |
| gtaactcagc gtccgctaat caaaaccaga tgtcagtccc cctttcttcc ccagcagcac | 1260 |
| ctccgggtcc ctctcggcag gggtctggga aggagttgac tgcgtccgcg ggcgccgcag | 1320 |
| taccccagcc tcgcccctcc ctccccacct ctgggagctg gctgaacgc ctgggaccct | 1380 |
| ggaagccgcg agtcgcgcgc cctgcgcacc cggccgaccc ccctcctgtg gcctctccct | 1440 |
| ggagaactcc gctgcggaca ggctaggcta cctgctctgt gtctccttgc cagaatattg | 1500 |
| attcagccta ggctgcaaaa ataagacagg gcagagaacc taggcaggga ggctatggaa | 1560 |
| gccaaactgg aaaactgcaa gcccaagaat tcctcctgga gagctagaga attggaaagg | 1620 |
| tcttggttcc aaggcagaga acacatgcac gcatttgcaa taggacagca ctgccgtttt | 1680 |
| cctcacaccc ttcgctgtgg gccaagtaca atcctacctg ggcccccaca catacctgac | 1740 |
| gtcatccctg ccacacagt catctaagag aaaggaaatt aatgtttgtg gatcacttac | 1800 |
| ttacagtgcc aaatgtttgt cattttcttt aatctccatc acggcccgt gttatgtatc | 1860 |
| taaagcccag tttcgttcag tatctttcag gcatctgtta tctgccagaa aggtctggcc | 1920 |
| atcggggatt ttcttctgaa tacgaaatag gaagtctttg tttaacaggt agagcgtttt | 1980 |
| agttttgcag gatgtcaaga gttctggaaa ttggttgcac cacaatgtaa atgaacttaa | 2040 |
| cacttctgaa ctgtacactt aaaaatggtt taggagagga gttccctggt ggcctgggag | 2100 |
| ttaagaacta ggcattgtca ctgctgtggc tcaggtttga ccctggctgg ggaaattctg | 2160 |
| catgccacag gcacagcccc gccaaaaatg gttataataa taaatgttat gttctgcgaa | 2220 |
| ttttactaaa aaataggaag tccctatctt cctgaaggga agaggaagtg gtaatttcaa | 2280 |
| gacacttact caaagtcacc caactagtaa gcattcagca cagatacccca ccaccaaagg | 2340 |
| gtatgttctc catccctctt gctttctctg actgggaaga gccgagtgtc tgtcacattc | 2400 |
| actgagaggt gggaggggag agggctacag agaggggctt ggatgccccc catgccatt | 2460 |
| atggcatgtc tcccagggc ccccaggcct ggcagtaaat gtgggcacac ctgccccgcc | 2520 |
| tcttggctga ttcccacc | 2538 |

<210> SEQ ID NO 9
<211> LENGTH: 4242
<212> TYPE: DNA
<213> ORGANISM: Artificial Sequence
<220> FEATURE:
<223> OTHER INFORMATION: Sequence of pGL4.10[luc2] vector (4242 bp)

<400> SEQUENCE: 9

| | |
|---|---|
| ggcctaactg gccggtacct gagctcgcta gcctcgagga tatcaagatc tggcctcggc | 60 |
| ggccaagctt ggcaatccgg tactgttggt aaagccacca tggaagatgc caaaaacatt | 120 |
| aagaagggcc cagcgccatt ctaccccactc gaagacggga ccgccggcga gcagctgcac | 180 |
| aaagccatga gcgctacgc cctggtgccc ggcaccatcg cctttaccga cgcacatatc | 240 |
| gaggtggaca ttacctacgc cgagtacttc gagatgagcg ttcggctggc agaagctatg | 300 |
| aagcgctatg ggctgaatac aaaccatcgg atcgtggtgt gcagcgagaa tagcttgcag | 360 |

-continued

```
ttcttcatgc cgtgttggg tgccctgttc atcggtgtgg ctgtggcccc agctaacgac      420
atctacaacg agcgcgagct gctgaacagc atgggcatca gccagcccac cgtcgtattc      480
gtgagcaaga aagggctgca aaagatcctc aacgtgcaaa agaagctacc gatcatacaa      540
aagatcatca tcatggatag caagaccgac taccagggct ccaaagcat gtacaccttc       600 gtgacttccc atttgccacc cggcttcaac gagtacgact cgtgcccga gagcttcgac       660 cgggacaaaa ccatcgccct gatcatgaac agtagtggca gtaccggatt gcccaagggc      720
gtagccctac cgcaccgcac cgcttgtgtc cgattcagtc atgcccgcga ccccatcttc      780
ggcaaccaga tcatccccga caccgctatc ctcagcgtgg tgccatttca ccacggcttc      840
ggcatgttca ccacgctggg ctacttgatc tgcggctttc gggtcgtgct catgtaccgc      900
ttcgaggagg agctattctt gcgcagcttg caagactata agattcaatc tgccctgctg      960
gtgcccacac tatttagctt cttcgctaag agcactctca tcgacaagta cgacctaagc     1020
aacttgcacg agatcgccag cggcggggcg ccgctcagca aggaggtagg tgaggccgtg     1080
gccaaacgct tccacctacc aggcatccgc cagggctacg gcctgacaga acaaccagc      1140 gccattctga tcaccccga aggggacgac aagcctggcg cagtaggcaa ggtggtgccc      1200
ttcttcgagg ctaaggtggt ggacttggac accggtaaga cactgggtgt gaaccagcgc     1260
ggcgagctgt gcgtccgtgg ccccatgatc atgagcggct acgttaacaa ccccgaggct     1320
acaaacgctc tcatcgacaa ggacggctgg ctgcacagcg gcgacatcgc ctactgggac     1380
gaggacgagc acttcttcat cgtggaccgg ctgaagagcc tgatcaaata caagggctac     1440
caggtagccc cagccgaact ggagagcatc ctgctgcaac accccaacat cttcgacgcc     1500
ggggtcgccg gcctgccga cgacgatgcc ggcgagctgc cgccgcagt cgtcgtgctg       1560 gaacacggta aaaccatgac cgagaaggag atcgtggact atgtggccag ccaggttaca     1620
accgccaaga gctgcgcgg tggtgttgtg ttcgtggacg aggtgcctaa aggactgacc      1680
ggcaagttgg acgcccgcaa gatccgcgag attctcatta aggccaagaa gggcggcaag     1740
atcgccgtgt aataattcta gagtcgggc ggccggccgc ttcgagcaga catgataaga     1800
tacattgatg agtttggaca aaccacaact agaatgcagt gaaaaaaatg ctttatttgt     1860
gaaatttgtg atgctattgc tttatttgta accattataa gctgcaataa acaagttaac     1920
aacaacaatt gcattcattt tatgtttcag gttcaggggg aggtgtggga ggtttttaa      1980 agcaagtaaa acctctacaa atgtggtaaa atcgataagg atccgtcgac cgatgccctt     2040
gagagccttc aacccagtca gctccttccg gtgggcgcgg ggcatgacta tcgtcgccgc     2100
acttatgact gtcttcttta tcatgcaact cgtaggacag gtgccggcag cgctcttccg     2160
cttcctcgct cactgactcg ctgcgctcgg tcgttcggct gcggcgagcg gtatcagctc     2220
actcaaaggc ggtaatacgg ttatccacag aatcagggga taacgcagga agaacatgt      2280 gagcaaaagg ccagcaaaag gccaggaacc gtaaaaaggc cgcgttgctg gcgttttcc      2340 ataggctccg ccccctgac gagcatcaca aaaatcgacg ctcaagtcag aggtggcgaa      2400
acccgacagg actataaaga taccaggcgt ttccccctgg aagctccctc gtgcgctctc     2460
ctgttccgac cctgccgctt accggatacc tgtccgcctt ctcccttcg ggaagcgtgg      2520 cgctttctca tagctcacgc tgtaggtatc tcagttcggt gtaggtcgtt cgctccaagc     2580
tgggctgtgt gcacgaaccc cccgttcagc ccgaccgctg cgccttatcc ggtaactatc     2640
gtcttgagtc aacccggta agacacgact tatcgccact ggcagcagcc actggtaaca     2700
```

| | | | | |
|---|---|---|---|---|
| ggattagcag | agcgaggtat | gtaggcggtg | ctacagagtt | cttgaagtgg tggcctaact | 2760 |
| acggctacac | tagaagaaca | gtatttggta | tctgcgctct | gctgaagcca gttaccttcg | 2820 |
| gaaaaagagt | tggtagctct | tgatccggca | aacaaaccac | cgctggtagc ggtggttttt | 2880 |
| ttgtttgcaa | gcagcagatt | acgcgcagaa | aaaaaggatc | tcaagaagat cctttgatct | 2940 |
| tttctacggg | gtctgacgct | cagtggaacg | aaaactcacg | ttaagggatt ttggtcatga | 3000 |
| gattatcaaa | aaggatcttc | acctagatcc | ttttaaatta | aaaatgaagt tttaaatcaa | 3060 |
| tctaaagtat | atatgagtaa | acttggtctg | acagcggccg | caaatgctaa accactgcag | 3120 |
| tggttaccag | tgcttgatca | gtgaggcacc | gatctcagcg | atctgcctat ttcgttcgtc | 3180 |
| catagtggcc | tgactccccg | tcgtgtagat | cactacgatt | cgtgagggct taccatcagg | 3240 |
| ccccagcgca | gcaatgatgc | cgcgagagcg | gcgttcaccg | gcccccgatt tgtcagcaat | 3300 |
| gaaccagcca | gcagggaggg | ccgagcgaag | aagtggtcct | gctactttgt ccgcctccat | 3360 |
| ccagtctatg | agctgctgtc | gtgatgctag | agtaagaagt | tcgccagtga gtagtttccg | 3420 |
| aagagttgtg | gccattgcta | ctggcatcgt | ggtatcacgc | tcgtcgttcg gtatggcttc | 3480 |
| gttcaactct | ggttcccagc | ggtcaagccg | ggtcacatga | tcacccatat tatgaagaaa | 3540 |
| tgcagtcagc | tccttagggc | ctccgatcgt | tgtcagaagt | aagttggccg cggtgttgtc | 3600 |
| gctcatggta | atggcagcac | tacacaattc | tcttaccgtc | atgccatccg taagatgctt | 3660 |
| ttccgtgacc | ggcgagtact | caaccaagtc | gttttgtgag | tagtgtatac ggcgaccaag | 3720 |
| ctgctcttgc | ccggcgtcta | tacgggacaa | caccgcgcca | catagcagta ctttgaaagt | 3780 |
| gctcatcatc | gggaatcgtt | cttcggggcg | gaaagactca | aggatcttgc cgctattgag | 3840 |
| atccagttcg | atatagccca | ctcttgcacc | cagttgatct | tcagcatctt ttactttcac | 3900 |
| cagcgtttcg | gggtgtgcaa | aaacaggcaa | gcaaatgcc | gcaaagaagg gaatgagtgc | 3960 |
| gacacgaaaa | tgttggatgc | tcatactcgt | cctttttcaa | tattattgaa gcatttatca | 4020 |
| gggttactag | tacgtctctc | aaggataagt | aagtaatatt | aaggtacggg aggtattgga | 4080 |
| caggccgcaa | taaaatatct | ttatttcat | tacatctgtg | tgttggtttt ttgtgtgaat | 4140 |
| cgatagtact | aacatacgct | ctccatcaaa | acaaaacgaa | acaaaacaaa ctagcaaaat | 4200 |
| aggctgtccc | cagtgcaagt | gcaggtgcca | gaacatttct | ct | 4242 |

<210> SEQ ID NO 10
<211> LENGTH: 4733
<212> TYPE: DNA
<213> ORGANISM: Artificial Sequence
<220> FEATURE:
<223> OTHER INFORMATION: Sequence of pEGFP-N1 vector (4733 bp)

<400> SEQUENCE: 10

| | | | | |
|---|---|---|---|---|
| tagttattaa | tagtaatcaa | ttacggggtc | attagttcat | agcccatata tggagttccg | 60 |
| cgttacataa | cttacggtaa | atggcccgcc | tggctgaccg | cccaacgacc cccgcccatt | 120 |
| gacgtcaata | atgacgtatg | ttcccatagt | aacgccaata | gggactttcc attgacgtca | 180 |
| atgggtggag | tatttacggt | aaactgccca | cttggcagta | catcaagtgt atcatatgcc | 240 |
| aagtacgccc | cctattgacg | tcaatgacgg | taaatggccc | gcctggcatt atgcccagta | 300 |
| catgacctta | tgggactttc | ctacttggca | gtacatctac | gtattagtca tcgctattac | 360 |
| catggtgatg | cggttttggc | agtacatcaa | tgggcgtgga | tagcggtttg actcacgggg | 420 |
| atttccaagt | ctccacccca | ttgacgtcaa | tgggagtttg | ttttggcacc aaaatcaacg | 480 |
| ggactttcca | aaatgtcgta | acaactccgc | cccattgacg | caaatgggcg gtaggcgtgt | 540 |

```
acggtgggag gtctatataa gcagagctgg tttagtgaac cgtcagatcc gctagcgcta      600
ccggactcag atctcgagct caagcttcga attctgcagt cgacggtacc gcgggcccgg      660
gatccaccgg tcgccaccat ggtgagcaag ggcgaggagc tgttcaccgg ggtggtgccc      720
atcctggtcg agctggacgg cgacgtaaac ggccacaagt tcagcgtgtc cggcgagggc      780
gagggcgatg ccacctacgg caagctgacc ctgaagttca tctgcaccac cggcaagctg      840
cccgtgccct ggcccaccct cgtgaccacc ctgacctacg gcgtgcagtg cttcagccgc      900
taccccgacc acatgaagca gcacgacttc ttcaagtccg ccatgcccga aggctacgtc      960
caggagcgca ccatcttctt caaggacgac ggcaactaca agacccgcgc cgaggtgaag     1020
ttcgagggcg acaccctggt gaaccgcatc gagctgaagg gcatcgactt caaggaggac     1080
ggcaacatcc tggggcacaa gctggagtac aactacaaca gccacaacgt ctatatcatg     1140
gccgacaagc agaagaacgg catcaaggtg aacttcaaga tccgccacaa catcgaggac     1200
ggcagcgtgc agctcgccga ccactaccag cagaacaccc ccatcggcga cggccccgtg     1260
ctgctgcccg acaaccacta cctgagcacc cagtccgccc tgagcaaaga ccccaacgag     1320
aagcgcgatc acatggtcct gctggagttc gtgaccgccg ccgggatcac tctcggcatg     1380
gacgagctgt acaagtaaag cggccgcgac tctagatcat aatcagccat accacatttg     1440
tagaggtttt acttgcttta aaaaacctcc cacacctccc cctgaacctg aaacataaaa     1500
tgaatgcaat tgttgttgtt aacttgttta ttgcagctta atggttac aaataaagca      1560
atagcatcac aaatttcaca aataaagcat ttttttcact gcattctagt tgtggtttgt     1620
ccaaactcat caatgtatct taaggcgtaa attgtaagcg ttaatatttt gttaaaattc     1680
gcgttaaatt tttgttaaat cagctcattt tttaaccaat aggccgaaat cggcaaaatc     1740
ccttataaat caaaagaata gaccgagata gggttgagtg ttgttccagt ttggaacaag     1800
agtccactat taagaacgt ggactccaac gtcaaagggc gaaaaaccgt ctatcagggc      1860
gatggcccac tacgtgaacc atcaccctaa tcaagttttt tggggtcgag gtgccgtaaa     1920
gcactaaatc ggaaccctaa agggagcccc cgatttagag cttgacgggg aaagccggcg     1980
aacgtggcga gaaaggaagg gaagaaagcg aaaggagcgg cgctagggc gctggcaagt      2040
gtagcggtca cgctgcgcgt aaccaccaca cccgccgcgc ttaatgcgcc gctacagggc     2100
gcgtcaggtg gcacttttcg gggaaatgtg cgcggaaccc ctatttgttt attttctaa      2160
atacattcaa atatgtatcc gctcatgaga caataaccct gataaatgct tcaataatat     2220
tgaaaaagga agagtcctga gcggaaaga accagctgtg aatgtgtgt cagttagggt       2280
gtggaaagtc cccaggctcc ccagcaggca gaagtatgca aagcatgcat ctcaattagt     2340
cagcaaccag gtgtggaaag tccccaggct cccagcagg cagaagtatg caaagcatgc      2400
atctcaatta gtcagcaacc atagtcccgc ccctaactcc gcccatcccg cccctaactc     2460
cgcccagttc cgcccattct ccgccccatg gctgactaat ttttttatt tatgcagagg     2520
ccgaggccgc ctcggcctct gagctattcc agaagtagtg aggaggcttt tttggaggcc     2580
taggcttttg caaagatcga tcaagagaca ggatgaggat cgtttcgcat gattgaacaa     2640
gatggattgc acgcaggttc tccggccgct tgggtggaga ggctattcgg ctatgactgg     2700
gcacaacaga caatcggctg ctctgatgcc gccgtgttcc ggctgtcagc gcaggggcgc     2760
ccggttcttt ttgtcaagac cgacctgtcc ggtgccctga atgaactgca agacgaggca     2820
gcgcggctat cgtggctggc cacgacgggc gttccttgcg cagctgtgct cgacgttgtc     2880
```

```
actgaagcgg gaagggactg gctgctattg ggcgaagtgc cggggcagga tctcctgtca    2940
tctcaccttg ctcctgccga gaaagtatcc atcatggctg atgcaatgcg gcggctgcat    3000
acgcttgatc cggctacctg cccattcgac caccaagcga acatcgcat cgagcgagca    3060
cgtactcgga tggaagccgg tcttgtcgat caggatgatc tggacgaaga gcatcagggg    3120
ctcgcgccag ccgaactgtt cgccaggctc aaggcgagca tgcccgacgg cgaggatctc    3180
gtcgtgaccc atggcgatgc ctgcttgccg aatatcatgg tggaaaatgg ccgcttttct    3240
ggattcatcg actgtggccg ctgggtgtg gcggaccgct atcaggacat agcgttggct    3300
acccgtgata ttgctgaaga gcttggcggc gaatgggctg accgcttcct cgtgctttac    3360
ggtatcgccg ctcccgattc gcagcgcatc gccttctatc gccttcttga cgagttcttc    3420
tgagcgggac tctggggttc gaaatgaccg accaagcgac gcccaacctg ccatcacgag    3480
atttcgattc caccgccgcc ttctatgaaa ggttgggctt cggaatcgtt ttccgggacg    3540
ccggctggat gatcctccag cgcgggatc tcatgctgga gttcttcgcc caccctaggg    3600
ggaggctaac tgaaacacgg aaggagacaa taccggaagg aacccgcgct atgacggcaa    3660
taaaagaca gaataaaacg cacggtgttg ggtcgtttgt tcataaacgc ggggttcggt    3720
cccagggctg gcactctgtc gatacccac cgagaccca ttggggccaa tacgcccgcg    3780
tttcttcctt tccccaccc caccccccaa gttcgggtga aggcccaggg ctcgcagcca    3840
acgtcggggc ggcaggccct gccatagcct caggttactc atatatactt tagattgatt    3900
taaaacttca ttttaatt aaaggatct aggtgaagat cctttttgat aatctcatga    3960
ccaaaatccc ttaacgtgag ttttcgttcc actgagcgtc agaccccgta gaaaagatca    4020
aaggatcttc ttgagatcct ttttttctgc gcgtaatctg ctgcttgcaa acaaaaaaac    4080
caccgctacc agcggtggtt tgtttgccgg atcaagagct accaactctt tttccgaagg    4140
taactggctt cagcagagcg cagataccaa atactgtcct tctagtgtag ccgtagttag    4200
gccaccactt caagaactct gtagcaccgc ctacatacct cgctctgcta atcctgttac    4260
cagtggctgc tgccagtggc gataagtcgt gtcttaccgg gttggactca agacgatagt    4320
taccggataa ggcgcagcgg tcgggctgaa cggggggttc gtgcacacag cccagcttgg    4380
agcgaacgac ctacaccgaa ctgagatacc tacagcgtga gctatgagaa agcgccacgc    4440
ttcccgaagg gagaaaggcg gacaggtatc cggtaagcgg cagggtcgga acaggagagc    4500
gcacgaggga gcttccaggg ggaaacgcct ggtatcttta tagtcctgtc gggtttcgcc    4560
acctctgact tgagcgtcga ttttttgtgat gctcgtcagg ggggcggagc ctatggaaaa    4620
acgccagcaa cgcggccttt ttacggttcc tggccttttg ctggccttt gctcacatgt    4680
tctttcctgc gttatcccct gattctgtgg ataaccgtat taccgccatg cat          4733
```

<210> SEQ ID NO 11
<211> LENGTH: 2579
<212> TYPE: DNA
<213> ORGANISM: Artificial Sequence
<220> FEATURE:
<223> OTHER INFORMATION: Sequence of pDsRed2-N1 vector (4689 bp)

<400> SEQUENCE: 11

```
tctagatggg gcaactggag atgatgggag aagaaagcct aagggactaa gaggaaagcc      60
acaatctgtc ggtaaatcct gccttgggta gaatcttcta aacctttccc gctttcagca     120
ctcttatcct gtcccacagg caaggggag ttttaaatc tcctctccat caccatcttg     180
tgttccgccc tggttcctaa ttgtcttact tgagccattc actccatcca gccgagacct     240
```

| | |
|---|---|
| tgttttagca gacacacaac tgcctagagt ctacacgccc ctcccttttcc caaactaaag | 300 |
| tgcttaggga cccagaaaat aggccaggtc ctcgtaacct tatcgaaata gcacagctag | 360 |
| gccttccacc caacaacact cagagactgg gccatagggt aggaaacagc atccagagtc | 420 |
| ttgtccagac agagcccaga catcttctgt agttaagagc cctctgggta ttctcacgtc | 480 |
| ctgccccaaa aaaggaacc aagcttatct gggggcggtg gggagaaggg ggtgtaagcc | 540 |
| aaagctaaag caactaaagc aactgtgttc tgataggaaa gatccctgga ctgagaacaa | 600 |
| gaaagctgtt ccgcaggaaa gaacacactg cgtggagtgt cagggaggag gccagcacct | 660 |
| ctggaatgcg gcaggaagat gaatgggaaa gatgaggtgg tggtggaggg cagcagccag | 720 |
| ggccttcaaa atcatcctcc agacaatgac aagcccggtc acctgatctg tgaagaggga | 780 |
| tggtctgcaa tctccaggcc ctcgagcctg tgcaaagggc aggctcaggc agctctgctg | 840 |
| ctagactaag gacatcccag gtgggcacgg agagctgcat ttctcgtaaa gcgccctagg | 900 |
| agcttctgtt gttcaccaga accacgagcc cctggactgg accgttcaca aggctcgttc | 960 |
| cagttagaaa attccatcac tctaagagct gggaggcacc taacctccaa gggagggaga | 1020 |
| gggaagtgga tctcccactt gccagcccag ggatgacttc caacagtgcc attacagtaa | 1080 |
| tggaaactgc agtgaaggtg ccagggctga cttctgtgaa gaaagaggag gacaggagtt | 1140 |
| cccctagtgg ctcatcagaa atgaatctga ctagcatcca tgaggatgca ggttcaatcc | 1200 |
| ctggcctcat tcagtggctt aaggatccag cgttgccgag agctgtgatg taggtcacag | 1260 |
| acgcggctca gatcccgtgt tgctgttgct gtggctgtgg cataggtcag aagcgacagc | 1320 |
| tctgatttga cccctaacct gggaacctcc atatcccgct agtgcggccc ttaaaagaca | 1380 |
| aaaagaagga aaagagaaga aaagacatag gcgaacagaa aggcagatga cagggtggca | 1440 |
| gggccagcct acacgatggc ccgaccagaa ttcacaaaga agccacaagg atgcaaatca | 1500 |
| atcaaataaa cctttgttca aaaaaattta tctcacctgt gagtgggaga acaagtcac | 1560 |
| cccagggctt ctggtgactt caaattgata gggagaaaat ggttgcccca ggggattaaa | 1620 |
| agcttggtat ctgctactcc tttagagttg gcctgtctcc tccactttcc cacaattcca | 1680 |
| ccatttcccc ctcccactgg gctgggatgc agctgtggag tggctcagct ccaaggacta | 1740 |
| ggggctccac agcccaggtc cggcggccag ccctcccact tccagcctgg aagtgggatg | 1800 |
| gggagtggga tgagatgaac ccggcagatt gtagccacag atgtggatgt gcagggtcca | 1860 |
| gcacagggct tgggtgagga gggcggcacc ccatcccttg tctgaagacc aagcagacag | 1920 |
| tactcaggac ttgggagggg gttggggggag gaggagtgca tgaaactgag aagaaccttc | 1980 |
| tagctgcctg cgccaggagg tacccgggag ctgaaggaga tggagtgccc cagagcagaa | 2040 |
| agcccctgca ggtctggatg ttctaggctg gatgaggggg cgaggcaggc ctggggacct | 2100 |
| gggaagacca ggcgcagtac ctgccttgct tctgaaaatg ctgctccaac gtggaaaaac | 2160 |
| actcccacca tctttctttg gagaaagcct gtaatattcc aacaccaaaa cctctcacta | 2220 |
| gaggttcccg tggagatggg ttccagatga aagggaagg aggaggcatg ggcgctgcct | 2280 |
| aacctccatc ctccattcct taccccctctc ccaccggctt ctgaagccgg ggtcagaaga | 2340 |
| aagggttaaa gccttaaaag gggaccgatt ttgcggggct ctggggggtcg gctggcacac | 2400 |
| cctgagcggc ccgcccttc tctctagtgt ccagaaccct ccctgccctg cccaggccta | 2460 |
| acggccacag ggggagggcc ccccttact gcagaccgcc actctcccac accaatatcg | 2520 |
| gaccgcctcc tcctccctct gccaccccctt ctcgctcccc actcagcctc tgattggcc | 2579 |

<210> SEQ ID NO 12
<211> LENGTH: 13874
<212> TYPE: DNA
<213> ORGANISM: Artificial Sequence
<220> FEATURE:
<223> OTHER INFORMATION: multicistronic vector of pTet retrovirus

<400> SEQUENCE: 12

| | | | | | |
|---|---|---|---|---|---|
| tttgaaagac | cccacccgta | ggtggcaagc | tagcttaagt | aacgccactt | tgcaaggcat | 60 |
| ggaaaaatac | ataactgaga | atagaaaagt | tcagatcaag | gtcaggaaca | agaaacagc | 120 |
| tgaataccaa | acaggatatc | tgtggtaagc | ggttcctgcc | ccggctcagg | gccaagaaca | 180 |
| gatgagacag | ctgagtgatg | ggccaaacag | gatatctgtg | gtaagcagtt | cctgccccgg | 240 |
| ctcggggcca | agaacagatg | gtccccagat | gcggtccagc | cctcagcagt | ttctagtgaa | 300 |
| tcatcagatg | tttccagggt | gccccaagga | cctgaaaatg | accctgtacc | ttatttgaac | 360 |
| taaccaatca | gttcgcttct | cgcttctgtt | cgcgcgcttc | cgctctccga | gctcaataaa | 420 |
| agagcccaca | acccctcact | cggcgcgcca | gtcttccgat | agactgcgtc | gcccgggtac | 480 |
| ccgtattccc | aataaagcct | cttgctgttt | gcatccgaat | cgtggtctcg | ctgttccttg | 540 |
| ggagggtctc | ctctgagtga | ttgactaccc | acgacggggg | tctttcattt | gggggctcgt | 600 |
| ccgggatttg | gagaccccctg | cccagggacc | accgacccac | caccgggagg | taagctggcc | 660 |
| agcaacttat | ctgtgtctgt | ccgattgtct | agtgtctatg | tttgatgtta | tgcgcctgcg | 720 |
| tctgtactag | ttagctaact | agctctgtat | ctggcggacc | cgtggtggaa | ctgacgagtt | 780 |
| ctgaacaccc | ggccgcaacc | ctgggagacg | tcccaggac | tttgggggcc | gtttttgtgg | 840 |
| cccgacctga | ggaagggagt | cgatgtggaa | tccgaccccg | tcaggatatg | tggttctggt | 900 |
| aggagacgag | aacctaaaac | agttcccgcc | tccgtctgaa | ttttgctttc | ggtttggaa | 960 |
| ccgaagccgc | gcgtcttgtc | tgctgcagcg | ctgcagcatc | gttctgtgtt | gtctctgtct | 1020 |
| gactgtgttt | ctgtatttgt | ctgaaaatta | gggccagact | gttaccactc | ccttaagttt | 1080 |
| gaccttaggt | cactggaaag | atgtcgagcg | gatcgctcac | aaccagtcgg | tagatgtcaa | 1140 |
| gaagagacgt | tgggttacct | tctgctctgc | agaatggcca | acctttaacg | tcggatggcc | 1200 |
| gcgagacggc | acctttaacc | gagacctcat | cacccaggtt | aagatcaagg | tcttttcacc | 1260 |
| tggcccgcat | ggacacccag | accaggtccc | ctacatcgtg | acctgggaag | ccttggcttt | 1320 |
| tgaccccccct | ccctgggtca | gcccctttgt | acaccctaag | cctccgcctc | ctcttcctcc | 1380 |
| atccgccccg | tctctccccc | ttgaacctcc | tcgttcgacc | ccgcctcgat | cctcccttta | 1440 |
| tccagccctc | actccttctc | taggcgccgg | aattccgatc | tgatagcttg | ccacaacccg | 1500 |
| taccaaagat | ggatagatcc | ggaaagcctg | aactcaccgc | gacgtctgtc | gagaagtttc | 1560 |
| tgatcgaaaa | gttcgacagc | gtctccgacc | tgatgcagct | ctcggagggc | gaagaatctc | 1620 |
| gtgctttcag | cttcgatgta | ggagggcgtg | gatatgtcct | gcgggtaaat | agctgcgccg | 1680 |
| atggtttcta | caaagatcgt | tatgtttatc | ggcactttgc | atcggccgcg | ctcccgattc | 1740 |
| cggaagtgct | tgacattggg | gaattcagcg | agagcctgac | ctattgcatc | tcccgccgtg | 1800 |
| cacagggtgt | cacgttgcaa | gacctgcctg | aaaccgaact | gcccgctgtt | ctgcagccgg | 1860 |
| tcgcggaggc | catggatgcg | atcgctgcgg | ccgatcttag | ccagacgagc | gggttcggcc | 1920 |
| cattcggacc | gcaaggaatc | ggtcaataca | ctacatggcg | tgatttcata | tgcgcgattg | 1980 |
| ctgatcccca | tgtgtatcac | tggcaaactg | tgatggacga | caccgtcagt | gcgtccgtcg | 2040 |
| cgcaggctct | cgatgagctg | atgctttggg | ccgaggactg | ccccgaagtc | cggcacctcg | 2100 |

```
tgcacgcgga tttcggctcc aacaatgtcc tgacggacaa tggccgcata acagcggtca    2160
ttgactggag cgaggcgatg ttcggggatt cccaatacga ggtcgccaac atcttcttct    2220
ggaggccgtg gttggcttgt atggagcagc agacgcgcta cttcgagcgg aggcatccgg    2280
agcttgcagg atcgccgcgg ctccgggcgt atatgctccg cattggtctt gaccaactct    2340
atcagagctt ggttgacggc aatttcgatg atgcagcttg ggcgcagggt cgatgcgacg    2400
caatcgtccg atccggagcc gggactgtcg ggcgtacaca aatcgcccgc agaagcgcgg    2460
ccgtctggac cgatggctgt gtagaagtac tcgccgatag tggaaaccga cgccccagca    2520
ctcgtccgag ggcaaaggaa tagagtagat gccgaccgaa caagagctga tttcgagaac    2580
gcctcagcca gcaactcgcg cgagcctagc aaggcaaatg cgagagaacg gccttacgct    2640
tggtggcaca gttctcgtcc acagttcgct aagctcgctc ggctgggtcg cgggagggcc    2700
ggtcgcagtg attcaggccc ttctggattg tgttggtccc cagggcacga ttgtcatgcc    2760
cacgcactcg ggtgatctga ctgatcccgc agattggaga tcgccgcccg tgcctgccga    2820
ttgggtgcag atctatttaa atatcaaata aacctttgtt caaaaaaatt tatctcacct    2880
gtgagtggga gagacaagtc accccagggc ttctggtgac ttcaaattga tagggagaaa    2940
atggttgccc caggggatta aaagcttggt atctgctact cctttagagt tggcctgtct    3000
cctccacttt cccacaattc caccatttcc ccctcccact gggctgggat gcagctgtgg    3060
agtggctcag ctccaaggac tagggctcc acagcccagg tccggcggcc agccctccca    3120
cttccagcct ggaagtggga tggggagtgg gatgagatga accggcagat tgtagccac    3180 agatgtggat gtgcagggtc cagcacaggg cttgggtgag gagggcggca ccccatccct    3240
tgtctgaaga ccaagcagac agtactcagg acttgggagg gggttggggg aggaggagtg    3300
catgaaactg agaagaacct tctagctgcc tgcgccagga ggtacccggg agctgaagga    3360
gatggagtgc cccagagcag aaagcccctg caggtctgga tgttctaggc tggatgaggg    3420
ggcgaggcag gcctggggac ctgggaagac caggcgcagt acctgccttg cttctgaaaa    3480
tgctgctcca acgtgaaaaa acactcccac catctttctt tggagaaagc ctgtaatatt    3540
ccaacaccaa aacctctcac tagaggttcc cgtggagatg ggttccagat gaaagggaa    3600 ggaggaggca tgggcgctgc ctaacctcca tcctccattc cttacccctc tcccaccggc    3660
ttctgaagcc ggggtcagaa gaaagggtta agccttaaa aggggaccga ttttgcgggg    3720
ctctgggggt cggctggcac accctgagcg gccccgccct tctctctagt gtccagaacc    3780 ctccctgcc tgcccaggcc taacggccac agggggaggg ccccccttta ctgcagaccg    3840
ccactctccc acaccaatat cggaccgcct cctcctccct ctgccacccc ttctcgctcc    3900
ccactcagcc tctgattggc catcgatatg ctgcccggtt tggcactgct cctgctggcc    3960
gcctggacgg ctcgggcgct ggaggtaccc actgatggta atgctggcct gctggctgaa    4020
ccccagattg ccatgttctg tggcagactg aacatgcaca tgaatgtcca gaatgggaag    4080
tgggattcag atccatcagg gaccaaaacc tgcattgata ccaaggaagg catcctgcag    4140
tattgccaag aagtctaccc tgaactgcag atcaccaatg tggtagaagc caaccaacca    4200
gtgaccatcc agaactggtg caagcgggc cgcaagcagt gcaagaccca tccccacttt    4260
gtgattccct accgctgctt agttggtgag tttgtaagtg atgcccttct cgttcctgac    4320
aagtgcaaat tcttacacca ggagaggatg gatgtttgcg aaactcatct tcactggcac    4380
accgtcgcca aagagacatg cagtgagaag agtaccaact tgcatgacta cggcatgttg    4440
```

```
ctgccctgcg gaattgacaa gttccgaggg gtagagtttg tgtgttgccc actggctgaa    4500
gaaagtgaca atgtggattc tgctgatgcg gaggaggatg actcggatgt ctggtggggc    4560
ggagcagaca cagactatgc agatgggagt gaagacaaag tagtagaagt agcagaggag    4620
gaagaagtgg ctgaggtgga agaagaagaa gccgatgatg acgaggacga tgaggatggt    4680
gatgaggtag aggaagaggc tgaggaaccc tacgaagaag ccacagagag aaccaccagc    4740
attgccacca ccaccaccac caccacagag tctgtggaag aggtggttcg agttcctaca    4800
acagcagcca gtacccctga tgccgttgac aagtatctcg agacacctgg ggatgagaat    4860
gaacatgccc atttccagaa agccaaagag aggcttgagg ccaagcaccg agagagaatg    4920
tcccaggtca tgagagaatg ggaagaggca gaacgtcaag caaagaactt gcctaaagct    4980
gataagaagg cagttatcca gcatttccag gagaaagtgg aatctttgga acaggaagca    5040
gccaacgaga gacagcagct ggtggagaca cacatggcca gagtggaagc catgctcaat    5100
gaccgccgcc gcctggccct ggagaactac atcaccgctc tgcaggctgt tcctcctcgg    5160
cctcgtcacg tgttcaatat gctaaagaag tatgtccgcg cagaacagaa ggacagacag    5220 cacacccctaa agcatttcga gcatgtgcgc atggtggatc ccaagaaagc cgctcagatc    5280
cggtcccagg ttatgacaca cctccgtgtg atttatgagc gcatgaatca gtctctctcc    5340
ctgctctaca cgtgcctgc agtggccgag gagattcagg atgaagttga tgagctgctt    5400
cagaaagagc aaaactattc agatgacgtc ttggccaaca tgattagtga accaaggatc    5460
agttacggaa acgatgctct catgccatct ttgaccgaaa cgaaaaccac cgtggagctc    5520
cttcccgtga atggagagtt cagcctggac gatctccagc cgtggcattc tttgggct    5580 gactctgtgc cagccaacac agaaaacgaa gttgagcctg ttgatgcccg ccctgctgcc    5640
gaccgaggac tgaccactcg accaggttct gggttgacaa atatcaagac ggaggagatc    5700
tctgaagtga atctggatgc agaattccga catgactcag gatatgaagt tcatcatcaa    5760
aaattggtgt tctttgcaga agatgtgggt tcaaacaaag gtgcaatcat tggactcatg    5820
gtgggcggtg ttgtcatagc gacagtggtc atcatcacct tggtgatgct gaagaagaaa    5880
cagtacacat ccattcatca tggtgtggtg gaggttgacg ccgctgtcac cccagaggag    5940
cgccacctgt ccaatctgca gcagaacggc tacgaaaatc caacctacaa gttctttgag    6000
cagatgcaga acttaattaa ggcatgcgga agcggagcta ctaacttcag cctgctgaag    6060
caggctggag acgtggagga gaaccctgga cctagatcta tggctgagcc ccgccaggag    6120
ttcgaagtga tggaagatca cgctgggacg tacgggttgg gggacaggaa agatcagggg    6180
ggctacacca tgcaccaaga ccaagagggt gacacggacg ctggcctgaa agctgaagaa    6240
gcaggcattg agacaccccc cagcctggaa gacgaagctg ctggtcacgt gacccaagct    6300
cgcatggtca gtaaaagcaa agacgggact ggaagcgatg acaaaaaagc caaggggggct    6360 gatggtaaaa cgaagatcgc cacaccgcgg ggagcagccc ctccaggcca agggccag    6420 gccaacgcca ccaggattcc agcaaaaacc ccgcccgctc aaagacacc acccagctct    6480 ggtgaacctc caaaatcagg ggatcgcagc ggctacagca gccccggctc cccaggcact    6540
cccggcagcc gctcccgcac cccgtccctt ccaaccccac ccaccggga gccaagaag    6600 gtggcagtgg tccgtactcc acccaagtcg ccgtcttccg ccaagagccg cctgcagaca    6660
gcccccgtgc ccatgccaga cctgaagaat gtcaagtcca agatcggctc cactgagaac    6720
ctgaagcacc agccgggagg cgggaaggtg cagataatta ataagaagct ggatcttagc    6780
aacgtccagt ccaagtgtgg ctcaaaggat aatatcaaac acgtcctggg aggcggcagt    6840
```

```
gtgcaaatag tctacaaacc agttgacctg agcaaggtga cctccaagtg tggctcatta    6900
ggcaacatcc atcataaacc aggaggtggc caggtggaag taaaatctga gaagcttgac    6960
ttcaaggaca gagtccagtc gaagattggg tccctggaca atatcaccca cgtccctggc    7020
ggaggaaata aaaagattga aacccacaag ctgaccttcc gcgagaacgc caaagccaag    7080
acagaccacg gggcggagat cgtgtacaag tcgccagtgg tgtctgggga cacgtctcca    7140
cggcatctca gcaatgtctc ctccaccggc agcatcgaca tggtagactc gccccagctc    7200
gccacgctag ctgacgaggt gtctgcctcc ctggccaagc agggtttgga attcggaagc    7260
ggagctacta acttcagcct gctgaagcag gctggagacg tggaggagaa ccctggacct    7320
ctcgagatga cagagttacc tgcaccgttg tcctacttcc agaatgcaca gatgtctgag    7380
gacaaccacc tgagcaatac tgtacgtagc cagaatgaca atagagaacg gcaggagcac    7440
aacgacagac ggagccttgg ccaccctgag ccattatcta atggacgacc ccagggtaac    7500
tcccggcagg tggtggagca agatgaggaa gaagatgagg agctgacatt gaaatatggc    7560
gccaagcatg tgatcatgct cttttgtccct gtgactctct gcatggtggt ggtcgtggct    7620
accattaagt cagtcagctt ttatacccgg aaggatgggc agctaatcta tacccattc    7680 acagaagata ccgagactgt gggccagaga gccctgcact caattctgaa tgctgccatc    7740
atgatcagtg tcattgttgt cctgactatc ctcctggtgg ttctgtataa atacaggtgc    7800
tataaggtca tccatgcctg gcttattata tcatctctat tgttgctgtt ctttttttca    7860
ttcatttact tgggggaagt gtttaaaacc tataacgttg ctgtggacta cattactgtt    7920
gcactcctga tctggaattt tggtgtggtg ggaatgattt ccattcactg gaaaggtcca    7980
cttcgactcc agcaggcata tctcattatg attagtgccc tcatggccct ggtgtttatc    8040
aagtacctcc ctgaatggac tgcgtggctc atcttggctg tgatttcagt atatgattta    8100
gtggctgttt tgtgtccgaa aggtccactt cgtatgctgg ttgaaacagc tcaggagaga    8160
aatgaaacgc ttttccagc tgtcatttac tcctcaacaa tggtgtggtt ggtgaatatg    8220
gcagaaggag acccggaagc tcaaggagaa gtatccaaaa attccaagta taatgcagaa    8280
agcacagaaa gggagtcaca agacactgtt gcagagaatg atgatggcgg ttcagtgag    8340 gaatgggaag cccagaggga cagtcatcta gggcctcatc gctctacacc tgagtcacga    8400
gctgctgtcc aggaactttc cagcagtatc ctcgctggtg aagacccaga ggaaggggga    8460
gtaaaacttg gattgggaga tttcattttc tacagtgttc tggttggtaa agcctcagca    8520
acagccagtg gagactggaa cacaaccata gcctgtttcg tagccatatt aattggtttg    8580
tgccttacat tattactcct tgccatttc aagaaagcat tgccagctct tccaatctcc    8640
atcacctttg gcttgttttt ctactttgcc acagattatc ttgtacagcc ttttatggac    8700
caattagcat tccatcaatt ttatatctag cctgcaggtc tagatagcta gcctccctat    8760
agtgagtcgt attacgtaga tccagacatg ataagataca ttgatgagtt tggacaaacc    8820
acaactagaa tgcagtgaaa aaaatgcttt atttgtgaaa tttgtgatgc tattgcttta    8880
tttgtaacca ttataagctg caataaacaa gttaacaaca acaattgcat tcattttatg    8940
tttcaggttc aggggggagt gtgggaggtt ttttaattcg cggccgcctc gagagatccc    9000
ctcaggatat agtagtttcg cttttgcata gggaggggga aatgtagtct tatgcaatac    9060
tcttgtagtc ttgcaacatg gtaacgatga gttagcaaca tgccttacaa ggagagaaaa    9120
agcaccgtgc atgccgattg gtggaagtaa ggtggtacga tcgtgcctta ttaggaaggc    9180
```

-continued

```
aacagacggg tctgacatgg attggacgaa ccactgaatt ccgcattgca gagatattgt    9240
atttaagtgc ctagctcgat acagcaaacg ccatttgacc attcaccaca ttggtgtgca    9300
cctccaagct tgttaattca ccatgtctag actggacaag agcaaagtca taaacggcgc    9360
tctggaatta ctcaatggag tcggtatcga aggcctgacg acaaggaaac tcgctcaaaa    9420
gctgggagtt gagcagccta ccctgtactg gcacgtgaag aacaagcggg ccctgctcga    9480
tgccctgcca atcgagatgc tggacaggca tcatacccac ttctgccccc tggaaggcga    9540
gtcatggcaa gactttctgc ggaacaacgc caagtcattc cgctgtgctc tcctctcaca    9600
tcgcgacggg gctaaagtgc atctcggcac ccgcccaaca gagaaacagt acgaaaccct    9660
ggaaaatcag ctcgcgttcc tgtgtcagca aggcttctcc ctggagaacg cactgtacgc    9720
tctgtccgcc gtgggccact ttacactggg ctgcgtattg gaggaacagg agcatcaagt    9780
agcaaaagag gaaagagaga cacctaccac cgattctatg cccccacttc tgagacaagc    9840
aattgagctg ttcgaccggc agggagccga acctgccttc cttttcggcc tggaactaat    9900
catatgtggc ctgagaaaac agctaaagtg cgaaagcggc gggccggccg acgcccttga    9960
cgattttgac ttagacatgc tcccagccga tgcccttgac gactttgacc ttgatatgct   10020
gcctgctgac gctcttgacg attttgacct tgacatgctc cccgggtaac taagtaagga   10080
tcaacatcga attcgatttc tgttcctgtt aatcaacctc tggattacaa aatttgtgaa   10140
agattgactg gtattcttaa ctatgttgct cctttttacgc tatgtggata cgctgcttta   10200
atgcctttgt atcatgctat tgcttcccgt atggctttca ttttctcctc cttgtataaa   10260
tcctggttgc tgtctcttta tgaggagttg tggcccgttg tcaggcaacg tggcgtggtg   10320
tgcactgtgt ttgctgacgc aaccccact ggttggggca ttgccaccac ctgtcagctc   10380 cttttccggga ctttcgcttt cccctccct attgccacgg cggaactcat cgccgcctgc   10440
cttgcccgct gctggacagg ggctcggctg ttgggcactg acaattccgt ggtgttgtcg   10500
gggaagctga cgtcctttcc atggctgctc gcctgtgttg ccacctggat tctgcgcggg   10560
acgtccttct gctacgtccc ttcggccctc aatccagcgg accttccttc ccgcggcctg   10620
ctgccggctc tgcggcctct tccgcgtctt cgccttcgcc ctcagacgag tcggatctcc   10680
ctttgggccg cctccccgcc tgtttcgcct cgggctcaat cactagtgaa ttcgataaaa   10740
taaaagattt tatttagtct ccagaaaaag gggggaatga agacccac ctgtaggttt     10800 ggcaagctag cttaagtaac gccattttgc aaggcatgga aaaatacata actgagaata   10860
gagaagttca gatcaaggtc aggaacagat ggaacagctg aatatgggcc aaacaggata   10920
tctgtggtaa gcagttcctg ccccggctca gggccaagaa cagatggaac agctgaatat   10980
gggccaaaca ggatatctgt ggtaagcagt tcctgccccg gctcagggcc aagaacagat   11040 ggtcccaga tgcggtccag ccctcagcag tttctagaga accatcagat gtttccaggg   11100
tgccccaagg acctgaaatg accctgtgcc ttatttgaac taaccaatca gttcgcttct   11160
cgcttctgtt cgcgcgcttc tgctcccccga gctcaataaa agagcccaca cccctcact   11220 cggggcgcca gtcctccgat tgactgagtc gcccgggtac ccgtgtatcc aataaaccct   11280
cttgcagttg catccgactt gtggtctcgc tgttccttgg gagggtctcc tctgagtgat   11340
tgactacccg tcagcggggg tctttcattt gggggctcgt ccgggatcgg gagacccctg   11400
cccagggacc accgacccac caccgggagg taagctggct gcctcgcgcg tttcggtgat   11460
gacggtgaaa acctctgaca catgcagctc ccggagacgg tcacagcttg tctgtaagcg   11520
gatgccggga gcagacaagc ccgtcagggc gcgtcagcgg gtgttggcgg gtgtcggggc   11580
```

```
gcagccatga cccagtcacg tagcgatagc ggagtgtata ctggcttaac tatgcggcat   11640
cagagcagat tgtactgaga gtgcaccata tgcggtgtga ataccgcac  agatgcgtaa   11700 ggagaaaata ccgcatcagg cgctcttccg cttcctcgct cactgactcg ctgcgctcgg   11760
tcgttcggct gcggcgagcg gtatcagctc actcaaaggc ggtaatacgg ttatccacag   11820
aatcagggga taacgcagga agaacatgt  gagcaaaagg ccagcaaaag gccaggaacc   11880
gtaaaaaggc cgcgttgctg gcgttttcc  ataggctccg ccccctgac  gagcatcaca   11940 aaaatcgacg ctcaagtcag aggtggcgaa acccgacagg actataaaga taccaggcgt   12000
ttccccctgg aagctccctc gtgcgctctc ctgttccgac cctgccgctt accggatacc   12060
tgtccgcctt tctcccttcg ggaagcgtgg cgctttctca tagctcacgc tgtaggtatc   12120
tcagttcggt gtaggtcgtt cgctccaagc tgggctgtgt gcacgaaccc cccgttcagc   12180
ccgaccgctg cgccttatcc ggtaactatc gtcttgagtc caacccggta agacacgact   12240
tatcgccact ggcagcagcc actggtaaca ggattagcag agcgaggtat gtaggcggtg   12300
ctacagagtt cttgaagtgg tggcctaact acggctacac tagaaggaca gtatttggta   12360
tctgcgctct gctgaagcca gttaccttcg gaaaaagagt tggtagctct tgatccggca   12420
aacaaaccac cgctggtagc ggtggttttt ttgtttgcaa gcagcagatt acgcgcagaa   12480
aaaaaggatc tcaagaagat cctttgatct tttctacggg gtctgacgct cagtggaacg   12540
aaaactcacg ttaagggatt ttggtcatga gattatcaaa aaggatcttc acctagatcc   12600
ttttaaatta aaaatgaagt tttaaatcaa tctaaagtat atatgagtaa acttggtctg   12660
acagttacca atgcttaatc agtgaggcac ctatctcagc gatctgtcta tttcgttcat   12720
ccatagttgc ctgactcccc gtcgtgtaga taactacgat acgggagggc ttaccatctg   12780
gccccagtgc tgcaatgata ccgcgagacc cacgctcacc ggctccagat ttatcagcaa   12840
taaaccagcc agccggaagg gccgagcgca gaagtggtcc tgcaacttta tccgcctcca   12900
tccagtctat taattgttgc cgggaagcta gagtaagtag ttcgccagtt aatagtttgc   12960
gcaacgttgt tgccattgct gcaggcatcg tggtgtcacg ctcgtcgttt ggtatggctt   13020
cattcagctc cggttcccaa cgatcaaggc gagttacatg atccccatg  ttgtgcaaaa   13080 aagcggttag ctccttcggt cctccgatcg ttgtcagaag taagttggcc gcagtgttat   13140
cactcatggt tatggcagca ctgcataatt ctcttactgt catgccatcc gtaagatgct   13200
tttctgtgac tggtgagtac tcaaccaagt cattctgaga atagtgtatg cggcgaccga   13260
gttgctcttg cccggcgtca cacgggata  ataccgcgcc acatagcaga actttaaaag   13320
tgctcatcat tggaaaacgt tcttcggggc gaaaactctc aaggatctta ccgctgttga   13380
gatccagttc gatgtaaccc actcgtgcac ccaactgatc ttcagcatct tttactttca   13440
ccagcgtttc tgggtgagca aaaacaggaa ggcaaaatgc cgcaaaaaag gaataagggc   13500 gacacggaa  atgttgaata ctcatactct tcctttttca atattattga agcatttatc   13560
agggttattg tctcatgagc ggatacatat ttgaatgtat ttagaaaaat aaacaaatag   13620
gggttccgcg cacatttccc cgaaaagtgc cacctgacgt ctaagaaacc attattatca   13680
tgacattaac ctataaaaat aggcgtatca cgaggccctt tcgtcttcaa gaattcatac   13740
cagatcaccg aaaactgtcc tccaaatgtg tccccctcac actcccaaat tcgcgggctt   13800
ctgcctctta gaccactcta ccctattccc cacactcacc ggagccaaag ccgcggccct   13860
tccgtttctt tgct                                                    13874
```

<210> SEQ ID NO 13
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 13
attaattcta gatggggcaa ctggag                                   26

<210> SEQ ID NO 14
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 14
gctagcggcc aatcagaggc tgag                                     24

<210> SEQ ID NO 15
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 15
gagctctcta gatggggcaa ctggag                                   26

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
gctagcggcc aatcagaggc tgag                                     24

<210> SEQ ID NO 17
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 17
ggtaccaacc tccatcctcc attcct                                   26

<210> SEQ ID NO 18
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 18
ctcgagggtg ggaatcagcc aagag                                    25

<210> SEQ ID NO 19
<211> LENGTH: 2085
<212> TYPE: DNA
<213> ORGANISM: Artificial Sequence
<220> FEATURE:
<223> OTHER INFORMATION: APP cDNA

<400> SEQUENCE: 19

```
atgctgcccg gtttggcact gctcctgctg gccgcctgga cggctcgggc gctggaggta      60
cccactgatg gtaatgctgg cctgctggct gaaccccaga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac ccatccccac tttgtgattc cctaccgctg cttagttggt     360
gagtttgtaa gtgatgccct tctcgttcct gacaagtgca aattcttaca ccaggagagg     420
atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg ggcggagcag acacagacta tgcagatggg     660
agtgaagaca agtagtagaa gtagcagag gaggaagaag tggctgaggt ggaagaagaa     720
gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagttcct acaacagcag ccagtacccc tgatgccgtt     900
gacaagtatc tcgagacacc tggggatgag aatgaacatg cccatttcca aaagccaaa      960
gagaggcttg aggccaagca ccgagagaga atgtcccagg tcatgagaga atgggaagag    1020
gcagaacgtc aagcaaagaa cttgcctaaa gctgataaga aggcagttat ccagcatttc    1080
caggagaaag tggaatcttt ggaacaggaa gcagccaacg agagacagca gctggtggag    1140
acacacatgg ccagagtgga agccatgctc aatgaccgcc gccgcctggc cctggagaac    1200
tacatcaccg ctctgcaggc tgttcctcct cggcctcgtc acgtgttcaa tatgctaaag    1260
aagtatgtcc gcgcagaaca aaggacaga cagcacaccc taaagcattt cgagcatgtg    1320
cgcatggtgg atcccaagaa agccgctcag atccggtccc aggttatgac acacctccgt    1380
gtgatttatg agcgcatgaa tcagtctctc tccctgctct acaacgtgcc tgcagtggcc    1440
gaggagattc aggatgaagt tgatgagctg cttcagaaag agcaaaacta ttcagatgac    1500
gtcttggcca catgattag tgaaccaagg atcagttacg gaaacgatgc tctcatgcca    1560
tcttttgaccg aaacgaaaac caccgtggag ctccttcccg tgaatggaga gttcagcctg    1620
gacgatctcc agccgtggca ttcttttggg gctgactctg tgccagccaa cacagaaaac    1680
gaagttgagc ctgttgatgc ccgccctgct gccgaccgag gactgaccac tcgaccaggt    1740
tctgggttga caaatatcaa gacggaggag atctctgaag tgaatctgga tgcagaattc    1800
cgacatgact caggatatga agttcatcat caaaaattgg tgttctttgc agaagatgtg    1860
ggttcaaaca aaggtgcaat cattggactc atggtgggcg tgttgtcat agcgacagtg    1920
gtcatcatca ccttggtgat gctgaagaag aaacagtaca catccattca tcatggtgtg    1980
gtggaggttg acgccgctgt cacccccagag gagcgccacc tgtccaatct gcagcagaac    2040
ggctacgaaa atccaaccta caagttcttt gagcagatgc agaac                   2085
```

<210> SEQ ID NO 20
<211> LENGTH: 1404
<212> TYPE: DNA
<213> ORGANISM: Artificial Sequence
<220> FEATURE:

<223> OTHER INFORMATION: PS1 cDNA

<400> SEQUENCE: 20

```
atgacagagt tacctgcacc gttgtcctac ttccagaatg cacagatgtc tgaggacaac    60
cacctgagca atactgtacg tagccagaat gacaatagag aacggcagga gcacaacgac   120
agacggagcc ttggccaccc tgagccatta tctaatggac gaccccaggg taactcccgg   180
caggtggtgg agcaagatga ggaagaagat gaggagctga cattgaaata tggcgccaag   240
catgtgatca tgctctttgt ccctgtgact ctctgcatgg tggtggtcgt ggctaccatt   300
aagtcagtca gcttttatac ccggaaggat gggcagctaa tctataccc attcacagaa    360
gataccgaga ctgtgggcca gagagccctg cactcaattc tgaatgctgc catcatgatc   420
agtgtcattg ttgtcctgac tatcctcctg gtggttctgt ataaatacag gtgctataag   480
gtcatccatg cctggcttat tatatcatct ctattgttgc tgttctttt ttcattcatt    540
tacttggggg aagtgtttaa aacctataac gttgctgtgg actacattac tgttgcactc   600
ctgatctgga attttggtgt ggtgggaatg atttccattc actggaaagg tccacttcga   660
ctccagcagg catatctcat tatgattagt gccctcatgg ccctggtgtt tatcaagtac   720
ctccctgaat ggactgcgtg gctcatcttg gctgtgattt cagtatatga tttagtggct   780
gttttgtgtc cgaaaggtcc acttcgtatg ctggttgaaa cagctcagga gagaaatgaa   840
acgctttttc cagctgtcat ttactcctca acaatggtgt ggttggtgaa tatggcagaa   900
ggagacccgg aagctcaaag gagagtatcc aaaaattcca agtataatgc agaaagcaca   960
gaaagggagt cacaagacac tgttgcagag aatgatgatg gcgggttcag tgaggaatgg  1020
gaagcccaga gggacagtca tctagggcct catcgctcta cacctgagtc acgagctgct  1080
gtccaggaac tttccagcag tatcctcgct ggtgaagacc cagaggaaag gggagtaaaa  1140
cttggattgg gagatttcat tttctacagt gttctggttg gtaaagcctc agcaacagcc  1200
agtggagact ggaacacaac catagcctgt ttcgtagcca tattaattgg tttgtgcctt  1260
acattattac tccttgccat tttcaagaaa gcattgccag ctcttccaat ctccatcacc  1320
tttgggcttg ttttctactt tgccacagat tatcttgtac agcctttat ggaccaatta   1380
gcattccatc aattttatat ctag                                         1404
```

UNITED STATES PATENT AND TRADEMARK OFFICE
CERTIFICATE OF CORRECTION

PATENT NO.          : 11,118,191 B2                                  Page 1 of 1
APPLICATION NO.     : 15/735185
DATED               : September 14, 2021
INVENTOR(S)         : Se Pill Park et al.

It is certified that error appears in the above-identified patent and that said Letters Patent is hereby corrected as shown below:

On the Title Page

Item [73], Line 3:
"Jejn-si" should be changed to -- Jeju-si --

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*